United States Patent [19]

Quertermous et al.

[11] Patent Number: 5,609,869

[45] Date of Patent: Mar. 11, 1997

[54] HYBRID IMMUNOGLOBULIN-THROMBOLYTIC ENZYME MOLECULES WHICH SPECIFICALLY BIND A THROMBUS, AND METHODS OF THEIR PRODUCTION AND USE

[75] Inventors: Thomas Quertermous, Nashville, Tenn.; Marschall S. Runge, Atlanta, Ga.; Edgar Haber, Salisbury, N.H.

[73] Assignee: The General Hospital Corporation, Boston, Mass.

[21] Appl. No.: 453,779

[22] Filed: May 30, 1995

Related U.S. Application Data

[60] Division of Ser. No. 96,173, Jul. 26, 1993, which is a continuation-in-part of Ser. No. 2,861, Jan. 15, 1993, and Ser. No. 589,435, Sep. 27, 1990, which is a continuation-in-part of Ser. No. 435,485, Jul. 7, 1989, abandoned, said Ser. No. 2,861, is a continuation of Ser. No. 234,051, Aug. 19, 1988, abandoned.

[51] Int. Cl.$^6$ .................................................. A61K 39/395
[52] U.S. Cl. ............................. 424/133.1; 424/134.1; 424/136.1; 424/139.1; 424/178.1; 424/192.1; 435/69.3; 435/252.3; 435/172.2; 435/172.3; 530/387.3; 530/388.25; 530/389.3; 536/23.4; 536/23.53
[58] Field of Search ..................... 435/69.3, 252.3, 435/172.2, 172.3, 7.1, 7.9, 7.6, 69.7; 536/23.4, 23.53; 530/350, 387.1, 387.3, 388.25, 389.3; 424/133.1, 134.1, 136.1, 178.1, 192.1, 139.1

[56] References Cited

U.S. PATENT DOCUMENTS

| | | | |
|---|---|---|---|
| 4,273,873 | 6/1981 | Sugitachi et al. | 435/180 |
| 4,368,149 | 1/1983 | Masucho et al. | 260/112 B |
| 4,414,148 | 11/1983 | Jansen et al. | 260/112 B |
| 4,470,925 | 9/1984 | Auditore-Hargreaves | 260/112 B |
| 4,474,893 | 10/1984 | Reading | 436/547 |
| 4,545,988 | 11/1985 | Nakayama et al. | 424/94 |
| 4,600,580 | 7/1986 | Smith | 424/94 |
| 4,671,958 | 6/1987 | Rodwell et al. | 424/85 |
| 4,673,573 | 6/1987 | Ferres et al. | 424/94.63 |
| 4,722,903 | 2/1988 | Kudryk et al. | 435/7 |
| 4,758,524 | 7/1988 | Bundesen et al. | 436/548 |
| 4,783,330 | 11/1988 | Furie et al. | 424/1.1 |
| 4,833,085 | 5/1989 | Schaumann et al. | 435/240.27 |
| 4,916,070 | 4/1990 | Matsueda et al. | 435/172.2 |
| 4,927,916 | 5/1990 | Matsueda et al. | 530/387 |
| 5,055,289 | 10/1991 | Fincke et al. | 424/85.4 |
| 5,116,613 | 5/1992 | Haber et al. | 424/85.5 |
| 5,256,413 | 10/1993 | Haber et al. | 424/85.5 |
| 5,275,812 | 1/1994 | Gold et al. | 424/85.8 |

FOREIGN PATENT DOCUMENTS

| | | |
|---|---|---|
| 25387 | 9/1984 | Australia . |
| 8434872 | 3/1985 | Australia . |
| 37521/85 | 7/1985 | Australia . |
| 12504/83 | 7/1987 | Australia . |
| 0088994 | 9/1983 | European Pat. Off. . |
| 0122487 | 10/1984 | European Pat. Off. . |
| 0120694 | 10/1984 | European Pat. Off. . |
| 0125023 | 11/1984 | European Pat. Off. . |
| 0146050 | 6/1985 | European Pat. Off. . |
| 0171496 | 2/1986 | European Pat. Off. . |
| 0173494 | 3/1986 | European Pat. Off. . |
| 0187658 | 7/1986 | European Pat. Off. . |
| 0241907 | 10/1987 | European Pat. Off. . |
| 0249007 | 12/1987 | European Pat. Off. . |
| 0271227 | 6/1988 | European Pat. Off. . |
| 0275606 | 7/1988 | European Pat. Off. . |
| 0336693 | 10/1989 | European Pat. Off. . |
| 0347078 | 12/1989 | European Pat. Off. . |
| 0355068 | 2/1990 | European Pat. Off. . |
| 0478366 | 4/1992 | European Pat. Off. . |
| 0068763 | 1/1983 | WIPO . |
| WO83/03971 | 11/1983 | WIPO . |
| WO85/00974 | 3/1985 | WIPO . |
| WO86/01411 | 3/1986 | WIPO . |
| WO86/01533 | 3/1986 | WIPO . |
| WO87/05934 | 10/1987 | WIPO . |
| WO87/06240 | 10/1987 | WIPO . |
| WO87/06263 | 10/1987 | WIPO . |
| WO88/03559 | 5/1988 | WIPO . |
| WO89/09817 | 10/1989 | WIPO . |
| WO90/02338 | 3/1990 | WIPO . |
| WO93/07174 | 4/1993 | WIPO . |

OTHER PUBLICATIONS

Angles-Cano, E. R., "Tissue Plasminogen Activator Determination with a Fibrin-Supported Film," 7–*Enzymes* 104:307, Abstract No. 104:144639d (1986).

Bode et al., "Characterization of an Antibody-Urokinase Conjugate," *J. Biol. Chem.* 262(22):10819–10823 (1987).

Bode et al., "Enhanced Thrombolysis in Plasma and In Vivo by Single-Chain Urokinase-Type Plasminogen Activator (scuPA) Conjugated To An Antifibrin Antibody," *Trans. Assoc. Am. Phys.* 102:7–12 (1989).

Bode et al., "Future Directions in Plasminogen Activator Therapy," *Clin. Cardiol.* 13:375–381 (1990).

Bode et al., "Improving on Nature: Antibody-Targeted Enzymes" in:The Year in Immunology, (Cruse and Lewis, eds.), S. Karger, Basel, Switzerland, vol. 6:185–196 (1990).

Bode et al., "Platelet-Targeted Fibrinolysis Enhances Clot Lysis and Inhibits Platelet Aggregation," *Circulation* 84(2):805–813 (1991).

(List continued on next page.)

*Primary Examiner*—Christine M. Nucker
*Assistant Examiner*—Laurie Scheiner
*Attorney, Agent, or Firm*—Sterne, Kessler, Goldstein & Fox, P.L.L.C.

[57] ABSTRACT

Hybrid immunoglobulin-enzyme molecules are provided which are composed of antibodies, or derivatives or fragments thereof, which specifically bind an arterial or venous thrombus that are operably linked to the enzymatically active portions of thrombolytic enzymes such as plasminogen activators. In a preferred embodiment the hybrid molecules specifically bind to fibrin and have fibrinolytic activity. The hybrid molecules of the present invention may be produced by any means, including chemical conjugation, or by means of recombinant DNA, genetic engineering and/or hybridoma technology. Methods for making and using the molecules in diagnosis and therapy are also disclosed.

5 Claims, 33 Drawing Sheets

OTHER PUBLICATIONS

Bode et al., "Targeting of Single-Chain Urokinase Plasminogen Activator By Conjugation To An Antiplatelet Antibody Results in Enhanced Clot Lysis," *Transactions of the Assoc. of American Physicians* 104:29–31 (1991).

Bode et al., "Purifying Antibody–Plasminogen Activator Conjugates," *Bioconjugate Chemistry* 3(4):269–272 (1992).

Bode et al., "Antifibrin–Urokinase Complex" in: Facts and Hopes in Thrombolysis and Acute Myocardial Infarction, (Effert et al. eds.), Steinkopff Verlag, Darmstadt, pp. 35–41 (1986).

Bode et al., "Conjugation to Antifibrin Fab' Enhances Fibrinolytic Potency of Single-Chain Urokinase Plasminogen Activator," *Circulation* 81:1974–1980 (1990).

Bode et al., "Characterization of an Antibody–Urokinase Conjugate," *Journal of Biological Chemistry* 272(22):10819–10823 (1987).

Bode et al., "Antibody–Directed Urokinase: A Specific Fibrinolytic Agent," *Science* 229:765–767 (1985).

Bode et al., "Thrombolysis by a Fibrin-Specific Antibody Fab'–Urokinase Conjugate," *J. Mol. Cell. Cardiol.* 19:335–341 (1987).

Bode et al., "Conjugation to an Antifibrin Antibody Enhances the Fibrinolytic Potency of Single-Chain Urokinase (scuPA)," *Clinical Research* 36(3):203A (1988).

Bode et al., "Antibody–Directed Fibrinolysis," *Journal of Biological Chemistry* 264(2):944–948 (1989).

Bosnjakovic et al., "Radiolabelled Anti-Human Fibrin Antibody: A New Thrombus-Detecting Agent", *The Lancet* pp. 452–454 (Feb. 26, 19770.

Boss et al., "Assembly of functional antibodies from immunoglobul in heavy and light chains synthesized in E. coli", *Nucl. Acid Res.* 12(9):3791–3806 (1984).

Boulianne et al., "Production of Functional Chimeric Mouse/Human Antibody," *Nature* 312:643–646 (1984).

Branscomb et al., "Bispecific Antibodies that Bind Both Tissue Plasminogen Activator (t-PA) and Fibrin," *Clinical Research* 35(3):264A (1987).

Branscomb et al., "Bispecific Monoclonal Antibodies Produced by Somatic Cell Fusion Increase the Potency of Tissue Plasminogen Activator," *Thrombosis and Hemostasis* 64(2):260–266 (1990).

Brennan et al., "Preparation of Bispecific Antibodies by Chemical Recombination of Monoclonal Immunoglobulin $G_1$ Fragments," *Science* 229:81–83 (1985).

Charpie et al., "Enhancement of Fibrinolysis by Single Chain Urokinase (scuPA) with a Bifunctional Antibody Having Both Fibrin and scuPA Specificities," *Clinical Research* 36(3):436A (1988).

Charpie et al., "A Bispecific Antibody Enhances the Fibrinolytic Potency of Single-Chain Urokinase," *Biochemistry* 29(27):6374–6378 (1990).

Charpie et al., "A Sequence-Dependent Monoclonal Antibody Specific for Single-Chain Urokinase," *Biochemical and Biophysical Research Communications* 152(2):910–915 (1988).

Collen et al., "Thrombolytic and Pharmacokinetic Properties of Conjugates of Urokinase-type Plasminogen Activator with a Monoclonal Antibody Specific for Crosslinked Fibrin," *Fibrinolysis* 3:197–202 (1989).

Collen et al., "Activation of Plasminogen by Pro-Urokinase," *J. Biol. Chem.* 261(3):1259–1266 (1986).

Deans et al., "Expression of an Immoglobul in Heavy Chain Gene Transfected into Lymphocytes," *Proc. Natl. Acad. Sci. USA* 81:1292–1296 (1984).

Declerck et al., "Fibrinolytic Response and Fibrin Fragment D-Dimer Levels in Patients with Deep Vein Thrombosis," *Thrombosis and Hemostasis* 58(4):1024–1029 (1987).

Dewerchin et al., "Effect of Chemical Conjugation of Recombinant Single-Chain urokinase-Type Plasminogen Activator with Monoclonal Antiplatelet Antibodies on Platelet Aggregation and on Plasma Clot Lysis In Vitro and In Vivo," *Blood* 78(4):1005–1018 (1991).

Dewerchin et al., "Biochemical Properties of Conjugates of Urokinase-Type Plasminogen Activator with a Monoclonal Antibody Specific for Cross-Linked Fibrin," *Eur. J. Biochem.* 185:141–149 (1989).

Derwerchin et al., "Enhancement of the Thrombolytic Potency of Plasminogen Activators by Conjugation with Clot-Specific Monoclonal Antibodies," *Bioconjugate Chemistry* 2(5):293–300 (1991).

Dewerchin et al., "Thrombolytic and Pharmacokinetic Properties of a Recombinant Chimeric Plasminogen Activator Consisting of a Fibrin Fragment D-Dimer Specific Humanized Monoclonal Antibody and a Truncated Single-Chain Urokinase," *Thrombosis and Hemostasis* 68(2):170–179 (1992).

Dillman et al., "Monoclonal Antibodies for Treating Cancer," *Annals of Internal Medicine* 111(7):592–603 (1989).

Doolittle, R. F., Fibrinogen and Fibrin, The Plasma Proteins: Structure, Function and Genetic Control (Putnam, F. W., ed.) Academic Press, 3rd Edition, N.Y., N.Y., 2: 109–156 (1975).

Dorai et al., "The Effect of Dihydrofolate Reductase-Mediated Gene Amplification on the Expression of Transfected Imunoglobulin Genes," *Journal of Immunology* 139(12):4232–4241 (1987).

Duberstein, R., "Scientists Develop New Technique for Producing Bispecific Monoclonals," *Genet. Eng. News* 6(1):22–23 (1986).

Fisher et al., "Isolation and Characterization of the Human Tissue-Type Plasminogen Activator Structural Gene Including Its 5' Flanking Region," *Journal of Biological Chemistry* 260(20):11223–11230 (1985).

Grossman et al., "Imaging of Fresh and Aged Venous Thrombi in the Dog with I-131 Monoclonal Antibody Specific for the $NH_2$-Terminal Region of Fibrin", *J. Nucl. Med.* 26(5):p. 21, Abstract No. 76 (1985).

Guenzler et al., "Chemical, Enzymological and Pharmacological Equivalence of Urokinase Isolated from Genetically Transformed Bacteria and Human Urine," *Chemical Abstracts* 103:40, Abstract No. 401b (1985).

Günzler et al., "Chemical, Enzymological and Pharmacological Equivalence of Urokinases Isolated from Genetically Transformed Bacteria and Human Urine," *Arzneim. –Forsch./Drug Res.l 35(I), Nr.* 3:652–662 (1985).

Gurewich et al., "Effective and Fibrin-specific Clot Lysis by a Zymogen Precursor Form of Urokinase (Pro-urokinase), A study in Vitro and in Two Annimal Species", *J. Clin. Invest.* 73:1731–1739 (1984).

Haber et al., "Recombinant Production of Chimeric Fibrin Antibody–Fibrinolytic Enzyme Molecules for Use as Thrombolytic agents," *Chem. Abstracts* 110:109428, Abstract No. 110:109425h (1988).

Haber, E., "In Vivo Diagnostic and Therapeutic Uses of Monoclonal Antibodies in Cardiology," *Ann. Rev. Med.* 37:249–261 (1986).

Haber, E., "Antibody–Targeted Fibrinolysis" in: Biotechnology in Clinical Medicine, (Albertini et al. eds.) Raven Press, Ltd., NY ,NY, pp. 77–82 (1987).

Haber, E., "Can Plasminogen Activators be Improved?", Editorial Comment, *Circulation* 82(5): 1874–1876 (1990).

Haber, E., "Antibody–targeted Plasminogen Activators" in: Thrombolysis: Basic Contributions and Clinical Progress, Mosby–Year Book, St. Louis, MO, pp. 71–79 (1991).

Haber, E. "Engineered Antibodies as Pharmacological Tools," *Immunological Reviews* 130:189–212 (1992).

Haber et al., "New Directions in the Use of Radioactive Antibodies and Plasma Proteins for *In Vivo* Diagnosis of Cardiovascular Diseases" in: Clinical Laboratory Assays: New Technology and Future Directions (Nakamura et al. eds.), Masson Pub., NY, NY, pp. 205–222 (1983).

Haber, E., Antibody Targeting as a Strategy in Thrombolysis, in Monoclonal antibodies in Cardiovascular Diseases (Khaw et al., eds.) Lea & Febiger, Philadelphia, pp. 187–197 (1994).

Haber et al., "Antibody–Targeted Thrombolytic Agents," *Japanese Circulation Journal* 54:345–353 (1990).

Haber et al., "Monoclonal Antibodies to Fibrin: Their Use for Imaging Clots, and in Antibody–Targeted Thrombolysis" in: Immunology and Molecular Biology of Cardiovascular Diseases, (Spry et al. eds.), MTP Press, Lancaster U.K., pp. 97–101 (1986).

Haber et al., "Antibody–Targeted Fibrinolysis" in: Advances in Gene Technology: Protein Engineering and Production, Proceedings of the 1988 Miami Bio/Technology Winter Symposium, Vol. 8 pp. 218–219 (1988).

Haber et al., "Antibody–Targeted Plasminogen Activators," in: Clinical Applications of Monoclonal Antibodies (Hubbard et al. eds.), Plenum Press, NY, NY, pp. 207–213 (1988).

Haber et al., "Antibody Targeting as a Thrombolytic Strategy," *Ann. N.Y. Acad. Sci.* 667:365–381 (1994).

Haber et al., "Innovative Approaches to Plasminogen Activator Therapy," *Science* 243:51–56 (1989).

Haber, E., "Antibodies As *In–Vivo* Diagnostic and Therapeutic Agents" in: Affinity Chromatography and Biological Recognition, San Diego: Academic Press, Inc., pp. 317–330 (1983).

Haber, E., "Monoclonal Antibodies: Their Potential as *In Vivo* Diagnostic and Therapeutic Agents," in: Monoclonal Antibodies and New Trends in Immunoassays, (Bizollon, Ch. A., ed.) Amsterdam: Elsevier Science Publishers B.V., pp. 81–90 (1984).

Haber, E., "Antibodies As Models for Rational Drug Design," *Biochemical Pharmacology* 32(13):1967–1977 (1983).

Harris, T. J. R., "Second–General Plasminogen Activators," *Protein Engineering* 1(6):449–458 (1987).

Hashimoto et al., "Thrombus Imaging with an I–123–Labeled F(ab')$_2$ Fragment of an Anti–Human Fibrin Monoclonal Antibody in a Rabbit Model," *Radiology* 127:223–226 (1989).

Hayzer et al., "Conjugation of Plasminogen Activators and Fibrin–Specific Antibodies To Improve Thrombolytic Therapeutic Agents," *Bioconjugate Chemistry* 2(5):301–308 (1991).

Hird et al., "Immunogherapy with Monoclonal Antibodies," *Genes and Therapy*:183–189 (1990).

Holvoet et al., "Binding Properties of Monoclonal Antibodies against Human Fragment D–Dimer of Cross–Linked Fibrin to Human Plasma Clots in an *In Vivo* Model in Rabbits," *Thrombosis and Hemostasis* 6(2):307–313 (1989).

Holvoet et al., "Characterization of a Chimeric Plasminogen Activator Consisting of a Single–chain Fv Fragment Derived from a Fibrin Fragment D–Dimer–specific Antibody and a Truncated Single–chain Urokinase," *The Journal of Biological Chemistry* 266(29):19717–19724 (1991).

Holvoet et al., "Thrombus Imaging with Murine Monoclonal Antibodies Against Fibrin Fragment D–Dimer in a Rabbit Jugular Vein Thrombosis Model," *Fibrinogen* (1):23, Abstract No. 92 (1987).

Holvoet et al., "Pharmacokinetics and Thrombolytic Properties of Chimeric Plasminogen Activators Consisting of a Single–chain Fv Fragment of a Fibrin–Specific Antibody Fused to Single–Chain Urokinase," *Blood* 81(3):696–703 (1993).

Hui et al., "Monoclonal Antibodies of Predetermined Specificity for Fibrin: A Rational Approach to Monoclonal Antibody Production," *Hybridoma* 5(3):215–222 (1986).

Hui et al., "Immunodetection of Human Fibrin Using Monoclonal Antibody–64C5 in an Extracorporeal Chicken Model," *Thrombosis and Hemostasis* 54(2):524–527 (1985).

Hui et al., "Monoclonal Antibodies to a Synthetic Fibrin–Like Peptide Bind to Human Fibrin but not Fibrinogen," *Science* 222:1129–1132 (1983).

Ito et al., "Fibrinogen–Specific Antibody as Carriers for Fibrinolytic Agents," *Fed. Proc.* 44:1846, Abstract No. 8382 (1985).

Kabnick et al., "Determinants that Contribute to Cytoplasmic Stability of Human c–fos and β–Globin mRNAs are Located at Several Sites in Each mRNA," *Molecular and Cellular Biology* 8(8):3244–3250 (1988).

Kato et al., "A Specified Immunoassay System for Hybrid Type Antigens," *Biochem. Methods* 94:325, Abstract No. 94:61048j (1981).

Khaw et al., "In–111 Labeled Monoclonal Anti–(Fibrin–Specific) Antibody: Detection of Pulmonary Emboli," *Fed. Proc.* 26(5):p. 21, Abstract No. 75 (1985).

Knight et al., "Comparison of In–111–Labeled Platelets and Iodinated Fibrinogen for the Detection of Deep Vein Thrombosis", *J. Nucl. Med.* 19(8):891–894 (1978).

Köhler et al., "Continuous Cultures of Fused Cells Secreting Antibody of Predefined Specificity," *Nature* 256:495–497 (1975).

Kudryk et al., "A Monoclonal Antibody with Ability to Distinguish Between NH$_2$–Terminal Fragments Derived from Fibrinogen and Fibrin," *Molecular Immunology* 20(11):1191–1200 (1983).

Kudryk et al., "Specificity of a Monoclonal Antibody for the NH$_2$–Terminal Region of Fibrin," *Molecular Immunology* 21(1):89–94 (1984).

Kurokawa et al., "Enchanced Fibrinolysis by a Bispecific Monoclonal Antibody Reactive to Fibrin and Tissue Plasminogen Activator," *Bio/Technology* 7:11263–1167 (1989).

Laffel et al., "Thrombolytic Therapy, A New Strategy for the Treatment of Acute Myocardial Infarction (First of Two Parts)," *New Engl. J. Med.* 311(11):710–717 (1984).

Laffel et al., "Thrombolytic Therapy, A new Strategy for the Treatment of Acute Myocardial Infarction (Second of Two Parts)", *New Engl. J. Med.* 311(12):770–776 (1984).

Lawn et al., "The Nucleotide Sequences of the Human β–Globin Gene," *Cell* 21:647–651 (1980).

Liau et al., "Evaluation of Monoclonal Antifibrin Antibodies by Their Binding to Human Blood Clots," *Thrombosis and Hemostasis* 57(1):49–54 (1987).

Lijnen et al., "Biochemical and Thrombolytic Properties of a Low Molecular Weight Form (Comprising Leu$^{144}$ through Leu$^{411}$) of Recombinant Single–Chain Urokinase–Type Plasminogen Activator," *Journal of Biological Chemistry* 263(12):5594–5598 (1988).

Love et al., "High–Level Expression of Antibody–Plasminogen Activator Fusion Proteins in Hybridoma Cells," *Thrombosis Research* 69:221–229 (1993).

Love et al., "Recombinant Antibodies Possessing Novel Effector Functions," *Methods in Enzymology* 178:515–527 (1989).

Lu et al., "Heteroantibody Duplexes Target Cells for Lysis by Cytotoxic T Lymphocytes," *Proc. Natl. Acad. Sci. USA* 82:8648–8652 (1985).

Lubin et al., "Strategies for the Design of Novel Thrombolytic and Antithrombolytic Agents," *TCM* 2(3):84–89 (1992).

Lubin et al., "The Tissue Plasminogen Activator Finger Domain Confers Fibrin–Dependent Enhancement of Catalytic Activity to Single–Chain Urokinase–Type Plasminogen Activator," *Journal of Biological Chemistry* 268(8):5550–5556 (1993).

Matsueda et al., "Synthetic Fibrin–Like Peptides Used as Antigens Yield Fibrin–Specific Antibodies," in: Peptides: Structure and Function, Proceedings of the Eighth American Peptide Symposium, Pierce Chemical Co., (Hruby et al. eds.) pp. 873–876 (1983).

Matsueda et al., "Monoclonal Antibodies Specific for Human Fibrin Monomer," *Fed. Proc.* 43(7):1992, Abstract 1375 (1983).

Matsueda et al., "Fibrin–Specific Monoclonal Antibodies Are Elicited by Immunization With A Synthetic Fibrin–Like Peptide," in: Fibrinogen –Structural Variants and Interactions, Walter de Gruyter & Co., Berlin, Germany, pp. 43–50, (1985).

Milstein et al., "Hybrid Hybridomas and Their Use in Immunohistochemistry," *Nature* 305:537–540 (1983).

Morrison, S. L., "Transfer and Expression of Immunoglobulin Genes," *Ann. Rev. Immunol.* 2:239–256 (1984).

Morrison et al., "Chimeric Human Antibody Molecules: Mouse Antigen–Binding Domains with Human Constant Region Domains," *Proc. Natl. Acad. Sci. USA* 81:6851–6855 (1984).

Morrison, S. L., "Tranfectomas Provide Novel Chimeric Antibodies," *Science* 229:1202–1207 (1985).

Morrison et al., "Genetically Engineered Antibody Molecules," *Advances in Immunology* 44:65–92 (1989).

Munro, A., "Uses of Chimeric Antibodies," *Nature* 312:597 (1984).

Nelles et al., "Characterization of Recombinant Human Single Chain Urokinase–Type Plasminogen Activator Mutants Produced by Site–Specific Mutagenesis of Lysine 158," *Journal of Biological Chemistry* 262(12):5682–5689 (1987).

Nelles et al., "Characterization of a Fusion Protein Consisting of Amino Acids 1 to 263 of Tissue–Type Plasminogen Activator and Amino Acids 144 to 411 to Urokinase–Type Plasminogen Activator," *Journal of Biological Chemistry* 262(22):10855–10862 (1987).

Neuberger, M. S., "Experssion and regulation of immunoglobulin heavy chain gene transfected into Lymphoid cells", *EMBO J.* 2(8):1373–1378 (1983).

Neuberger et al., "a Hapten–Specific Chimeric IgE Antibody with Human Physiological Effector Function," *Nature* 314:268–270 (1985).

Neuberger et al., "Recombinant Antibodies Possessing Novel Effector Functions," *Nature* 312:604–608 (1984).

Ochi et al., "Transfer of a Cloned Immunoglobulin Light–Chain Gene to Mutant Hybridoma Cells Restores Specific Antibody Production," *Nature* 302:340–342 (1983).

Ochi et al., "Functional immunoglobulin M production after transfection of a cloned immunoglobulin heavy and light chain genes into Lymphoid cells," *Proc. Natl. Acad. Sci. USA* 80:6351–6355 (1983).

Oi et al., "Immunoglobul in Gene Expression in Transformed Lymphoid Cells," *Proc. Natl. Acad. Sci. USA* 80:825–829 (1983).

Oi et al., "Chimeric Antibodies," *Bio Techniques* 4(3):214–221 (1986).

Pacella et al., "Induction of Fibrin–Specific Antibodies by Immunization With Synthetic Peptides That Correspond to Amino Termini of Thrombin Cleavage Sites," *Molecular Immunology* 20(5):521–527 (1983).

Philpott et al., "Selective Binding and Cytotoxicity of Rat Basophilic Leukemia Cells (RBL–1) with Immunoglobul in E–Biotin and Avidin–Glucose Oxidase Conjugates," *Journal of Immunology* 125(3):1201–1209 (1980).

Quertermous et al., "Human T Cell γ Chain Joining Regions and T Cell Development," *Journal of Immunology* 138(8):2687–2690 (1987).

Reed et al., "Acceleration of Plasma Clot Lysis by An Antibody to $\alpha_2$–Antiplasmin," *Trans. Assoc. Am. Physicians (U.S.)* 101:250–256 (1988).

Reed et al., "Synergistic fibrinolysis Combined effects of plasminogen activators and an antibody that inhibits $\alpha_2$–antiplasmin," *Proc. Natl. Acad. Sci. USA* 87:1114–1118 (1990).

Reed et al., "Inhibition of Clot–Bound $\alpha_2$–Antiplasmin Enhances in Vivo Thrombolysis," *Circulation* 82(1):164–168 (1990).

Reich et al., "Detection of venous thrombosis in the human by means of radioiodinated antifibrin–fibrinogen antibody", *Surgery* 60(6):1211–1215 (1966).

Rosebrough et al., "Radioimmunoimaging of Venous Thrombi Using Iodine–131 Monoclonal Antibody," *Radiology* 156:515–517 (1985).

Rosebrough et al., "Thrombus Imaging in the Dog with I–131 Monoclonal Antibody Specific for the NH$_2$–terminal Region of Fibrin", *Radiology* 153(Spec. Edit.), Abstract 858 (1984).

Runge et al., "A Recombinant Chimeric Plasminogen Activator with High Affinity for Fibrin has Increased Thrombolytic Potency In Vitro and In Vivo," *Proc. Natl. Acad. Sci. USA* 88:10337–10341 (1991).

Runge et al., "A Recombinant Molecule with Antifibrin Antibody and Single–Chain Urokinase Activities has Increased Fibrinolytic Potency," *Circ. Suppl. II* 78:II–509 (1988).

Runge et al., "Antibody Enhanced Thrombolysis: (1) Capture of Endogenous Tissue Plasminogen Activator (tPA) by a Heteroantibody Duplex and (2) Direct Targeting by an Antifibrin–tPA Conjugate In Vivo," *Clinical Research* 35(3):643A (1987).

Runge et al., "Increasing Selectivity of Plasminogen Activators with Antibodies," *Clinical Research* 36:501–506 (1988).

Runge et al., "Tissue–Type Plasminogen Activator–Antifibrin Monoclonal Antibody Conjugate Enhances Clot Lysis in Plasma," *Circulation* 74 (Supp. II): Abstract No. 984 (1986).

Runge et al., "Thrombosis and Thrombolysis in Cardiovascular Diseases: An Overview," The Heart and Cardiovascular System, Second Ed., (Fozzard et al. eds.), Raven Press, Ltd., NY, NY (1992).

Runge et al., "Hybrid Molecules: Insights into Plasminogen Activator Function," Mol. Biol. Med. 8:245–255 (1991).

Runge, M. S., "The Future of Thrombolytic Therapy," Heart Disease and Stroke, p. 39–42 (1992).

Runge et al., "Antibody–Enhanced Thrombolysis: Targeting of Tissue Plasminogen Activator In Vivo," Proc. Natl. Acad. Sci. USA 84:7659–7662 (1987).

Runge et al., "Antibody–Enhanced Thrombolysis: Capture of Tissue Plasminogen Activator by a Bispecific Antibody and Direct Targeting by an Antifibrin–Tissue Plasminogen Activator Conjugate In Vivo," Trans. Assoc. Am. Phys. 100:250–255 (1987).

Runge et al., "Conjugation to an Antifibrin Monoclonal Antibody Enhances the Fibrinolytic Potency of Tissue Plasminogen Activator In Vitro," Biochemistry 27:1153–1157 (1988).

Runge, M. S., "New Horizons in the Treatment of Coronary Artery Thrombosis," American Journal of Medical Sciences 301(1):21–27 (1991).

Runge et al., "Plasminogen Activators," Circulation 79(2):217–224 (1989).

Runge et al., "Tissue Type Plasminogen Activator Conjugated to an Antifibrin Monoclonal Antibody is a 10–Fold More Efficient Fibrinolytic Agent than Tissue Type Plasminogen Activator Alone," Clinical Research 34(2):469A (1986).

Runge, M. S., "Prevention of Thrombosis and Rethrombosis," Editorial Comment, Circulation 83(2):655–657 (1990).

Runge et al., "The Antibody Combining Site as a Tool in Thrombolysis," Molecular Biology of the Cardiovascular System, pp. 165–171 (1990).

Runge et al., "Antibody–Directed Fibrinolysis: A Bispecific (Fab')$_2$ That Binds to Fibrin and Tissue Plasminogen Activator," Bioconjugate Chimistry 1(14):274–277 (1990).

Salerno et al., "Monoclonal Antibodies to Human Urokinase Identify the Single–Chain Pro–Urokinase Precursor," Proc. Natl. Acad. Sci. USA 81:110–114 (1984).

Scheefers–Borchel et al., "Discrimination between fibrin and fibrinogen by a monoclonal antibody against a synthetic peptide", Proc. Natl. Acad. Sci. USA 82:7091–7095 (1985).

Schnee et al., "Construction and Expression of a Recombinant Antibody–Directed Thrombolytic Molecule," Clinical Research 35(3):575A (1987).

Schnee et al., "Construction and Expression of a Recombinant Antibody–Targeted Plasminogen Activator," Chemical Abstracts 107:158, Abstract No. 212913c (1987).

Schnee et al., "Construction and Expression of a Recombinant Antibody–Targeted Plasminogen Activator," Proc. Natl. Acad. Sci. USA 84:6904–6908 (1987).

Sevilla et al., "Plasminogen Activator–Anti–Human Fibrinogen Conjugate", Fed. Proc. 44(4):1073, Abstrate 3872 (1982).

Sharon et al. "Expression of a $V_H C_k$ Chimaeric Protein in Mouse Myeloma Cells," Nature 309:364–367 (1984).

Smith et al., "Fibrinolysis with acyl–enzymes:a new approach to thrombolytic theraphy", Nature 290:505–508 (1981).

Sobel et al., "Characterization of a CrossLink–Containing Fragment Derived from the α Polymer of Human Fibrin and its Application in Immunologic Studies Using Monoclonel Antibodies", Thromb. Haemostasis 46(1):240, Abstract 0758 (1981).

Soria et al., "Monoclonal Antibodies That React Preferentially with Fibrinogen Degradation Products or with Cross–Linked Fibrin Split Products," Annals N.Y. Acad. Sci. 408:665–666 (1983).

Spar et al., "Detection of Preformed Venous Thrombi in Dogs by Means of $I^{131}$–Labeled Antibodies to Dog Fibrinogen", Circulation Research XVII:322–329 (1965).

Stump et al., "Purification and Characterization of a Novel Low Molecular Weight Form of Single–Chain Urokinase–Type Plasminogen Activator," Journal of Biological Chemistry 261(36):17120–17126 (1986).

Stump et al., "Comparative Thrombolytic Properties of Single–Chain Forms of Urokinase–Type Plasminogen Activator", Blood 69(2):592–596 (1987).

Takeda et al., "Construction of Chimaeric Processed Immunoglobulin Genes Containing Mouse Variable and Human Constant Region Sequences," Nature 314:452–454 (1985).

Tan et al., "A Human–Mouse Chimeric Immunoglobulin Gene with a Human Variable Region is Expressed in Mouse Myeloma Cells," Journal of Immunology 135(5):3564–3567 (1985).

Tucker et al., "Sequence of the Cloned Gene for the Constant Region of Murine γ2b Immunoglobulin Heavy Chain," Science 206:1303–1306 (1979).

van Zonneveld et al., "Structure and Function of Human Tissue–Type Plasminogen Activator (t–PA)," Journal of Cellular Biochemistry 32:169–178 (1986).

Verde et al., "Identification and Primary Sequence of an Unspliced Human Urokinase Poly(A)$^+$RNA," Proc. Natl. Acad. Sci. USA 81:4727–4731 (1984).

Waldmann, T. A., "Monoclonal Antibodies in Diagnosis and Therapy," Science 252:1657–1662 (1991).

Williams et al., "Production of Antibody–Tagged Enzymes by Myeloma Cells: Application to DNA Polymerase I Klenow Fragment," Gene 43:319–324 (1986).

Wood et al., "The synthesis and in vivo assembly of functional antibodies in yeast," Nature 314:446–449 (1985).

HYBRID IMMUNOGLOBULIN-THROMBOLYTIC ENZYME MOLECULES WHICH SPECIFICALLY BIND A THROMBUS, AND METHODS OF THEIR PRODUCTION AND USE

U.S. GOVERNMENT IN THIS INVENTION

This invention was made, in part, with U.S. government support under National Institutes of Health grants HL-19259, HL-41619, HL-31950, HL-02414, HL-44307, HL-31469 and RR-00165. The U.S. government has certain rights in this invention.

CROSS-REFERENCE TO RELATED APPLICATIONS

This application is a division of application Ser. No. 08/096,173, filed Jul. 26, 1993, which is a Continuation-In-Part of U.S. patent application Ser. Nos. 08/002,861 filed Jan. 15, 1993 and 07/589,435, filed Sep. 27, 1990. U.S. application Ser. No. 08/002,861 is a continuation of U.S. application Ser. No. 07/234,051 (now abandoned) which was filed on Aug. 19, 1988 and which was a Continuation-in-Part of PCT Application No. US87/02968, filed Nov. 12, 1987 (inactive). U.S. application Ser. No. 07/589,435 is a Continuation-in-Part of U.S. application Ser. No. 07/435,485, filed Jul. 7, 1989 (abandoned) which is the U.S. national phase application of PCT Application No. US87/02968, filed Nov. 12, 1987. PCT Application No. US 87/02968 was a Continuation-in-Part of U.S. application Ser. No. 06/929,581, filed Nov. 12, 1986 (abandoned). This application is also related to commonly owned U.S. Pat. Nos. 4,916,070 and 4,927,916.

The disclosures of each of the above-referenced applications are herein incorporated in their entireties by reference.

FIELD OF THE INVENTION

This invention relates to hybrid immunoglobulin-thrombolytic enzyme molecules having an antigen binding site which specifically binds a thrombus that is linked to a second molecule comprising the enzymatically active portion of a thrombolytic enzyme. This invention is also directed to the methods of producing these novel hybrid immunoglobulin-enzyme molecules. This invention further relates to methods of using these hybrid immunoglobulin-enzyme molecules in immunodiagnostic and immunotherapeutic processes.

BACKGROUND OF THE INVENTION

When blood escapes from the vasculature, an intricate cascade of enzymatic reactions converts fibrinogen to fibrin, the structural protein in clotted blood. Blood clots, also called thrombi, may also be inappropriately formed within blood vessels in certain pathological conditions. Fibrinogen itself is the least soluble of the plasma proteins. With a 340,000 kDa MW, it possesses a two-fold symmetry arising from three pairs of non-identical polypeptide chains called A-alpha, B-beta and gamma. At the site of thrombosis, the coagulation cascade is activated to generate thrombin, which enzymatically cleaves polar peptides (Fibrinopeptide A from A-alpha and Fibrinopeptide B from B-beta), and results in fibrin monomer formation. Fibrin monomers, being much less soluble, spontaneously polymerize into a gel network. After polymerization, the fibrin clot is stabilized by Factor XIIIa, which introduces covalent interchain $\epsilon$-($\gamma$-glutamyl)lysine bonds. Fibrinogen and fibrin are identical in greater than 98% of their structure and differ only in two newly exposed amino termini, those of the fibrin alpha and beta chains. The amino acid sequence of these fibrin amino termini is known (Doolittle, R. F., "Fibrinogen and Fibrin," in Putnam, F. W., ed., *The Plasma Proteins: Structure, Function, and Genetic Control*, 3d ed., Vol. 2, New York: Academic Press, 1975, pp. 109–156).

Most myocardial infarctions are caused by a coronary thrombosis (DeWood et al., *N. Eng. J. Med.* 303:897 (1983)). The coronary thrombus can be lysed by thrombolytic agents thus restoring blood flow to the affected portion of the heart. These thrombolytic agents may be thrombolytic enzymes such as a plasminogen activator (PA). The PAs activate the conversion of plasminogen to the fibrinolytic enzyme plasmin. Plasmin has an affinity for fibrin and will lyse the fibrin present in the thrombus. This treatment with PAs is not without side effects. Plasmin acts non-selectively and therefore not only lyses the fibrin in the thrombus, but also attacks fibrinogen and clotting factors often resulting in severe bleeding diathesis.

Streptokinase, urokinase, prourokinase, and tissue-type PA (tPA) are PAs used for lysing thrombi. These PAs are indicated for the treatment for acute cardiovascular disease such as infarct, stroke, pulmonary embolism, deep vein thrombi, peripheral arterial occlusion, and other venous thrombi.

Streptokinase and urokinase constitute the first generation of PAs. Both streptokinase and urokinase, however, have severe limitations. Due to a low affinity for fibrin, both PAs will activate circulating and fibrin-bound plasminogen indiscriminately. The plasmin formed in circulating blood is neutralized before it can be used in thrombolysis. Residual plasmin will degrade several clotting factor proteins, for example, fibrinogen, factor V, and factor VIII, causing hemorrhagic potential.

Streptokinase, a bacterial protein, was the first identified PA. It forms a 1:1 stoichiometric complex with plasminogen and thereby converts it to its active form, plasmin. When administered within 4 hours of coronary occlusion, streptokinase has been shown to reduce mortality after myocardial infarction in a number of randomized trials (Simoons et al., *J. Am. Coll. Cardiol.* 7:717 (1986); and Hartman et al., *Am. Heart J.* 111:1030 (1986)). However, the use of this agent is invariably accompanied by a marked depletion of fibrinogen caused by the generation of excess plasmin. Further, streptokinase is strongly antigenic and patients with high antibody titers against it respond inefficiently to treatment and cannot remain on continuous treatment.

Urokinase is a two-chain, trypsin-like serine protease that activates plasminogen by limited proteolysis of the single, specific Arg-560-Val peptide bond (Violand et al., *J. Biol. Chem.* 251:3906–3912 (1976)). Results obtained with urokinase have been similar to those obtained for streptokinase in smaller-scale clinical trials (Mathey et al., *Am. J. Cardiol.* 55:878 (1985)).

Second generation PAs include tPA and single chain urokinase-like PA (scuPA). Unlike streptokinase and urokinase, tPA and scuPA exhibit fibrin-selective plasminogen activation. The selectivity of tPA derives from the presence of a fibrin binding site on the molecule. tPA binds fibrin with a kDa of 0.16 µM; when bound, its $K_m$ for plasminogen activation decreases from 83 µM to 0.18 µM and its $k_{cat}$ increases from 0.07 to 0.28 sec$^1$, resulting in an increase in catalytic efficiency of approximately 1000 fold. Although scuPA probably does not bind directly to fibrin, it activates fibrin-bound plasminogen much more readily than plasma plasminogen. Its fibrin selectivity is comparable to that of tPA (Collen et al., *Thromb. Haemost.* 52:27 (1984)).

tPA and scuPA are also considered native PAs because endothelial and other cells secrete them into the circulation. Initial studies of tPA and scuPA were conducted on proteins purified from cultured cell lines including the Bowes melanoma cell line for tPA, and transformed human kidney cells for scuPA. Both agents have subsequently been produced by recombinant DNA methods (Pennica et al., *Nature* 301:214 (1983); Holmes et al., *Biotechnology* 3:923 (1985)).

scuPA is cleaved by plasmin between amino acids Lys 158 and Ile 159. The resulting high molecular weight (HMW) two-chain urokinase has the catalytic activity of scuPA but does not have the fibrin selectivity and resistance to plasminogen activator-inhibitor I of its single-chain precursor. Low molecular weight (LMW) two-chain urokinase is the first generation form. The full length, HMW form of scuPA is the native PA and is the form that has been studied clinically as a second generation PA.

The light chain (amino terminal) of scuPA contains, in addition to an epidermal growth factor-like domain, a single kringle region that shows considerable homology with the kringles of tPA, despite the fact that scuPA does not appear to bind fibrin. Another property that differentiates scuPA from tPA is scuPA's resistance to irreversible inhibition by plasminogen activator-inhibitor I, as well as to other plasminogen activator-inhibitors. For this reason, unlike tPA, scuPA is stable in human plasma for extended periods. For example, plasminogen activator-inhibitor I binds reversibly to scuPA: when scuPA forms a ternary complex with fibrin and plasminogen, plasminogen activator-inhibitor I is displaced. It is not until after plasmin cleaves scuPA between residues Lys 158 and Ile 159 to form HMW two-chain urokinase that the catalytic site becomes susceptible to irreversible inhibition. LMW two-chain urokinase derives from subsequent cleavage of the Lys 136-Lys 137 peptide bond and is readily inhibited by plasminogen activator-inhibitor I.

Stump et al. (*J. Biol. Chem.* 261:17120 (1986)) have described a shortened form of scuPA that results from proteolytic cleavage during purification between residues Glu 143 and Leu 144. scuPA is probably not present in this form in vivo. LMW scuPA, now expressed by recombinant DNA methods (Nelles et al., *J. Biol. Chem.* 262:10855 (1987)) does not contain the amino terminal kringle.

Although it is only 14 amino acids longer than LMW two-chain urokinase, LMW scuPA manifests fibrin selectivity identical to that of native, HMW scuPA, clearly excluding the kringle from a role in fibrin selectivity. LMW (32-kDa) scuPA also retains another important property of native (54-kDa) scuPA—its resistance to plasminogen activator-inhibitor I.

Human tPA binds to fibrin and therefore favors the activation of plasminogen in close proximity to the thrombus thus potentially sparing fibrinogen elsewhere in the circulation. However, at the doses required for prompt lysis of coronary thrombi, the use of tPA can also result in hemorrhage.

It is now established that early therapy with PAs reduces mortality in patients with acute myocardial infarction (Aims Trial Study Group, *Lancet I*:545–549 (1988); Check, W. A., *Clin. Pharm.* 10:486–7 (1991); GISSI, *Lancet I*:397 (1986); GISSI-2, Lancet 336:65–71 (1990); ISIS-3, *Lancet* 339:753–770 (1992); and Simoons et al., *Lancet II*:578–582 (1985)). However, this treatment is complicated by: a) failure to achieve reperfusion in 15–20% of patients (TIMI Study Group, *New Engl. J. Med.* 312:932–936 (1985); Topol et al., *Ann. Intern. Med.* 103:837–843 (1985); Topol et al., *Circulation* 77:1100–1107 (1988)); b) abnormal bleeding, particularly hemorrhagic stroke in ~0.5 to 1% of the patients, that requires blood transfusions in ~10% of the patients (ISIS Steering Committee, Lancet 1987–I:502 (1987); Holvoet et al., *J. Biol. Chem.* 266:19717–19724 (1991)); and c) rethrombosis after cessation of therapy in 5–15% of patients (Topol et al., *J. Am. Coll. Cardiol.* 9:1205–1213 (1987); Topol et al., *N. Engl. J. Med.* 317:581–588 (1987); Chesebro et al., *N. Engl. J. Med.* 319:1544–1545 (1988); Braunwald et al., *J. Clin. Invest.* 76:1713–1719 (1985)). To reduce these complications, PAs have been developed that exhibit increased specificity for thrombus, altered clearance properties, or reduced inactivation by plasma inhibitors (Jackson et al., *Circulation* 82:930–40 (1990); Runge et al., *Proc. Natl. Acad. Sci. USA* 88:10337–10341 (1991); Collen et al., *Circulation* 82:1744–1753 (1990); Lijnen et al., *J. Biol. Chem.* 263:5594–5598 (1988); Browne et al., *J. Biol. Chem.* 263:1599–1602 (1988); Madison et al., *Nature* 339:721–724 (1989); Nelles et al., *J. Biol. Chem.* 262:5682–5689 (1987)). Initial studies in animal models demonstrated modest improvements in thrombolytic efficacy for most of these "third generation" molecules. In addition, PA therapy has been combined with therapeutic agents that inhibit platelet function or reduce thrombin activity (Heras et al., *Circulation* 79:657–665 (1989); Eidt et al., *J. Clin. Invest.* 84:18–27 (1989); Jang et al., *Circulation (Suppl)* 80:II:217 (1989)). While combined therapies augment thrombolysis and decrease rethrombosis, they also increase the risk of bleeding because they interrupt hemostatic function.

In order to increase the specificity of the thrombolytic agents to the thrombus, it has been shown that covalent linkage of urokinase to a fibrin-specific monoclonal antibody results in marked enhancement of fibrinolytic potency and specificity (Bode et al., *Science* 229:765–767 (1985)).

One function which is characteristic of every antibody molecule is specific binding to an antigenic determinant. Antibodies in vivo are bivalent and monospecific, containing two identical antigen binding sites. The specificity of the binding of an antigen by an antibody molecule is determined by the structure of the antibody's variable regions ($F_{ab}$) of both heavy and light chains.

Antibodies are tetrameric immunoglobulins consisting of two identical light (L) chains and two identical heavy (H) chains. Each protein chain consists of two principle regions: the N-terminal variable (V) region and the C-terminal constant (C) region. The variable light ($V_L$) and heavy ($V_H$) chains form the variable region domain. The variable domain determines recognition and specificity to a particular antigen. The constant region domains of light ($C_L$) and heavy ($C_H$) chains mediate the effector function responsible for executing the immune response. The hinge region (J) of the antibody molecule connects the Fab fragment to the Fc fragment of the antibody.

Within the variable region, there may be hypervariable regions known as diversity domains (D). These diversity domains are related to exons observed in the genes encoding for the variable regions.

The variable domain of an antibody, a protein structural definition, consists of both $V_L$ and $V_H$ segments of the light and heavy chains. It contains 6 hypervariable regions, three in the light chain and three in the heavy chain. On a genetic level, three exons are responsible for specifying $V_H$, including its framework and hypervariable regions; two exons specify $V_L$. The first two hypervariable regions of both $V_L$ and $V_H$ are specified by the V gene exons of the light and heavy chains respectively. The third hypervariable region of the light chain is specified by two exons, $V_L$ and $J_L$. The third hypervariable region of the heavy chain is specified by three exons $V_H$, D, and $J_H$.

Immunoglobulin gene expression occurs through the joining of the V gene to the C gene by somatic recombination in the B lymphocytes. These genes are joined to form the complete immunoglobulin. The rearranged, joined gene segments then encode the complete immunoglobulin or antigen binding domains of light and heavy variable chains.

There are five principal classes of heavy chains, characterized by chemical and isotypic properties. These heavy chain classes are referred to as mu, gamma, delta, alpha, and epsilon. There are five principal classes of immunoglobulins (antibodies) referred to as: IgG; IgM; IgD; IgA; and IgE. There are also two principal classes of light chains: kappa and lambda.

Antibodies with specificity to fibrin have been described in Hui et al. (*Science* 222:1129 (1983)). Other examples of antibodies with a specificity against fibrin have been described (Kudryk et al., *Mol. Imm.* 21:89 (1984); European Patent Application 146,050 to Callewaert, published Jun. 26, 1985, for "Site Selective Plasminogen Activator and Method of Making and Using Same"; and Australian Patent Application, AV-A-25387/84 to Bundesen et al. for "Monoclonal Antibodies with Specificity for Crosslinked Fibrin and Their Diagnostic Uses").

Antibodies having dual specificities have been prepared by subjecting antibodies of different specificities to a selective cleavage of the disulfide bridges that link the two heavy chains together. Antibody half-molecules are then reassociated under neutral pH to produce the hybrid antibodies having dual specificities (see, for example, Nisonhoff et al., *Nature* (London) 394:355 (1962); Brennan et al., *Science* 229:31 (1985); Liu et al., *Proc. Natl. Acad. Sci. USA* 82:8648 (1985); and commonly assigned formerly United States patent application, Ser. No. 851,554, filed Apr. 14, 1986, now U.S. Pat. No. 4,916,070).

Bispecific antibodies have also been produced from hybridomas. The preparation of bispecific monoclonal antibodies by fusion of antibody-producing hybridoma cells is described in Milstein et al., *Nature* (London) 305:537 (1983) and in PCT application WO83/103679.

Antibodies have also been cloned and produced by recombinant DNA techniques. Genes for heavy and light chains have been introduced into appropriate hosts and expressed, followed by reaggregation of these individual chains into functional antibody molecules (see, for example, Munro, *Nature* 312:597 (1984); Morrison, S. L. *Science* 229:1202 (1985); Oi et al., *BioTechniques* 4:214 (1986)); Wood et al., *Nature* 314:446-449 (1985)). Light and heavy chain variable regions have been cloned and expressed in foreign hosts, and maintain their binding ability (Moore et al., European Patent Publication 0088994 (published Sep. 21, 1983)).

Chimeric or hybrid antibodies have also been prepared by recombinant DNA techniques. Oi and Morrison describe a strategy for producing chimeric antibodies (*BioTechniques* 4:214 (1986)). On pages 218–220 thereof a chimeric:human IgG anti-Leu3 antibody is described. The authors state that a chimeric mouse:human anti-dansyl antibody has been made. This article indicates, without specifically stating so, that the Leu3 binding specificity and the anti-dansyl binding specificity have been cloned together into a single immunoglobulin molecule.

Morrison states that variable light or variable heavy chain regions can be attached to a non-Ig sequences to create fusion proteins (Table 1, *Science* 229:1202 (1985)). This article states that the fusion proteins have three potential uses: (1) to attach antibody specificity to enzymes for use in assays; (2) to isolate non-Ig proteins by antigen columns; and (3) to specifically deliver toxic agents. There is no description in this reference of any specific chimeric immunoglobulin molecule.

Neuberger et al. describe a chimeric antibody whose heavy chain is a human constant region fused to a mouse variable region that is specific for the hapten, 4-hydroxy-3-nitrophenyl-acetyl (*Nature* 314:268 (1985)).

European Patent Application 120,694 describes the genetic engineering of the variable and constant regions of an immunoglobulin molecule that is expressed in *E. coli* host cells. The application states on page 10 that the immunoglobulin molecule may be synthesized by a host cell with another peptide moiety attached to one of the constant domains. This peptide moiety is either cytotoxic or enzymatic. It also states on page 10 that the immunoglobulin molecule may also comprise a therapeutic agent. The description in the application and in the examples describe the use of a lambda-like chain derived from a monoclonal antibody which binds to 4-hydroxy-3-nitropenylacetal (NP) haptens.

European Patent Application 125,023 relates to the use of recombinant. DNA techniques to produce immunoglobulin molecules that are chimeric or otherwise modified. One of the uses for these immunoglobulin molecules is their use in whole body diagnosis and treatment, wherein antibodies directed to specific target disease tissues are injected into a patient (pages 3–4). The presence of the disease can be determined by attaching a suitable label to the antibodies, or the diseased tissue can be attacked by carrying a suitable drug with antibodies. The application describes antibodies engineered to aid the specific delivery of an agent as "altered antibodies."

PCT application WO83/03971 relates to a hybrid protein that comprises antibody-enzymatically active toxins.

PCT application W083/01533 describes on page 5 chimetic antibodies with the variable region of an immunoglobulin molecule linked to a portion of a second protein which may comprise the active portion of an enzyme.

Boulianne et al. constructed an immunoglobulin gene in which the DNA segments that encode mouse variable regions specific for the hapten trinitrophenol (TNP) are joined to segments that encode human mu and kappa constant regions (*Nature* 312:643 (1984)). These chimeric genes were expressed as functional TNP-binding chimeric IgM.

Morrison et al. created a chimetic molecule utilizing the heavy chain variable region exons of an anti-phosphoryl choline myeloma protein gene, which were joined to the exons of either human kappa light chain gene (*Proc. Natl. Acad. Sci. USA* 81:6851 (1984)). The genes were transfected into mouse myeloma cell lines, generating transformed cells that produced chimeric mouse-human IgG with antigen binding function.

Sharon et al. fused a gene encoding a mouse heavy chain variable region specific for azophenylarsonate with the mouse kappa light chain constant region gene (*Nature* 309:604 (1984)). This construct resulted in a polypeptide chain that dimerized with the corresponding $V_L$-Kappa polypeptide chain when introduced into the appropriate myeloma cell line. The $V_{Hkappa}V_LC_{kappa}$ molecule bound to the azophenylarsonate hapten.

Neuberger et al. joined the heavy chain variable region gene of a hapten-specific antibody to a gene specifying the synthesis of micrococcal nuclease, and obtained a hybrid molecule that had both antigen binding and enzymatic activity (*Nature* 312:604 (1984)).

Robbins and coworkers described covalently linked hybrid PAs that covalently linked the fibrin binding of the plasminogen A chain with the catalytic domain of urokinase (*Biochemistry* 25:3603–3611 (1986)). Stump et al. described a shortened form of scuPA which, like scuPA, was fibrin specific, although it apparently did not bind to fibrin directly (*J. Biol. Chem.* 26:17120–17126 (1986)). Attempts to further improve the fibrin specificity of this molecule by either site-directed mutagenesis to provide stability (Nelles et al., *J. Biol. Chem.* 262:10855–10862 (1987)), or by conferring direct fibrin affinity by creating a recombinant molecule combining the fibrin-binding A chain of tPA with the low molecular weight (LMW) form of scuPA (Nelles et al., *J. Biol. Chem.* 262:5682–5689 (1987) were disappointing.

It would be desirable to have a selective thrombolytic enzyme, such as a PA, that is characterized by high affinity and specificity for fibrin relative to fibrinogen, and that would effect activation of plasminogen only in the immediate environment of a fibrin-containing thrombus.

SUMMARY OF THE INVENTION

This invention relates to hybrid immunoglobulin-thrombolytic enzyme molecules having antigenic binding sites which specifically bind an epitope(s) specific for either a venous or arterial thrombus that are operably linked to an enzyme, or derivative or fragment thereof, comprising the enzymatically active site of a thrombolytic enzyme such as a PA. In a preferred embodiment, the antigentic binding sites of the hybrid molecules specifically bind fibrin and the enzymatically active sites of the hybrid molecules are from fibrinolytic enzyme molecules. In a preferred embodiment the antibody is an IgG molecule.

The invention is also directed to the production of these novel hybrid immunoglobulin-enzyme molecules. The invention also comprises: genetic sequences coding for the hybrid immunoglobulin-enzyme molecules; cloning and expression vectors containing such genetic sequences; hosts transformed with such vectors; and methods of production of such hybrid molecules by expression of these genetic sequences in such hosts.

This invention is further directed to methods of using these hybrid immunoglobulin-enzyme molecules in immunodiagnostic and immunotherapeutic processes.

In one embodiment, the invention is directed to a hybrid immunoglobulin-enzyme molecule, comprising: an antibody, or derivative or fragment thereof, which specifically binds fibrin that is operably linked to the active site of a fibrinolytic enzyme.

In another embodiment, the invention is directed to a recombinant DNA molecule, comprising: a DNA sequence coding for an antibody, or derivative or fragment thereof, which specifically binds a thrombus that is operably linked to a DNA sequence coding for a thrombolytic enzyme, wherein the DNA molecule encodes a hybrid immunoglobulin-enzyme molecule.

In another embodiment, the invention is directed to a recombinant DNA molecule, comprising: a DNA sequence coding for an antibody, or derivative or fragment thereof, which specifically binds fibrin that is operably linked to a DNA sequence coding for a fibrinolytic enzyme, wherein the DNA molecule encodes a hybrid immunoglobulin-enzyme molecule.

In another embodiment, the invention is directed to a vector comprising a recombinant DNA molecule comprising a DNA sequence coding for an antibody, or derivative or fragment thereof, which specifically binds a thrombus that is operably linked to a DNA sequence coding for a thrombolytic enzyme, wherein the DNA molecule encodes a hybrid immunoglobulin-enzyme molecule.

In another embodiment, the invention is directed to a vector comprising a recombinant DNA molecule comprising a DNA sequence coding for an antibody, or derivative or fragment thereof, which specifically binds fibrin that is operably linked to a DNA sequence coding for a fibrinolytic enzyme, wherein the DNA molecule encodes a hybrid immunoglobulin-enzyme molecule.

In another embodiment, the invention is directed to a vector selected from the group consisting of a plasmid, a phage or an artificial chromosome wherein the vector comprises a recombinant DNA molecule encoding a hybrid immunoglobulin-enzyme molecule of this invention.

In another embodiment, the invention is directed to a plasmid comprising a recombinant DNA molecule, comprising: a DNA sequence coding for an antibody, or derivative or fragment thereof, which specifically binds a thrombus that is operably linked to a DNA sequence coding for a thrombolytic enzyme, wherein the DNA molecule encodes a hybrid immunoglobulin-enzyme molecule.

In another embodiment, the invention is directed to a plasmid comprising a recombinant DNA molecule, comprising: a DNA sequence coding for an antibody, or derivative or fragment thereof, which specifically binds fibrin that is operably linked to a DNA sequence coding for a fibrinolytic enzyme, wherein the DNA molecule encodes a hybrid immunoglobulin-enzyme molecule.

In another embodiment, the invention is directed to an expression vector comprising a recombinant DNA molecule, comprising: a DNA sequence coding for an antibody, or derivative or fragments thereof, which specifically binds a thrombus that is operably linked to a DNA sequence coding for a thrombolytic enzyme, wherein the DNA molecule encodes a hybrid immunoglobulin-enzyme molecule; and regulatory sequences for expressing the recombinant DNA molecule.

In another embodiment, the invention is directed to an expression vector comprising a recombinant DNA molecule, comprising: a DNA sequence coding for an antibody, or derivative or fragments thereof, which specifically binds fibrin that is operably linked to a DNA sequence coding for a fibrinolytic enzyme, wherein the DNA molecule encodes a hybrid immunoglobulin-enzyme molecule; and regulatory sequences for expressing the recombinant DNA molecule.

In another embodiment, the invention is directed to a method for producing a recombinant hybrid immunoglobulin-enzyme molecule having an antibody, or derivative or fragment thereof, which specifically binds a thrombus that is operably linked to the active site of a thrombolytic enzyme, comprising:

introducing into a host a DNA sequence coding for an antibody, or derivative or fragment thereof, which specifically binds a thrombus that is operably linked to a DNA sequence coding for a thrombolytic enzyme; incubating the host under conditions in which the DNA sequence is expressed; and purifying the hybrid immunoglobulin-enzyme molecule.

In another embodiment, the invention is directed to a method for producing a recombinant hybrid immunoglobulin-enzyme molecule having an antibody, or derivative or fragment thereof, which specifically binds fibrin that is operably linked to the active site of a fibrinolytic enzyme, comprising:

introducing into a host a DNA sequence coding for an antibody, or derivative or fragment thereof, which specifically binds fibrin that is operably linked to the active site of a fibrolytic enzyme; incubating the host under conditions in which the DNA sequence is expressed; and purifying the hybrid immunoglobulin-enzyme molecule.

In another embodiment, the invention is directed to a host comprising the recombinant DNA molecules coding for these hybrid immunoglobulin-enzyme molecules.

In another embodiment, the invention is directed to a pharmaceutical composition comprising the hybrid immunoglobulin-enzyme molecules of this invention and a pharmaceutically acceptable carrier.

In another embodiment, the invention is directed to a method of lysing a thrombus in an animal comprising administering to the animal an effective amount of a pharmaceutical composition comprising the hybrid immunoglobulin-enzyme molecules of this invention, wherein the amount is effective to lyse the thrombus.

In another embodiment, the invention is directed to a method of imaging a thrombus in an animal, comprising: administering to the animal an effective amount of the hybrid immunoglobulin-enzyme molecules of the invention, wherein the molecule is labeled with a detectable label and the amount is effective to detectably label the thrombus; and detecting the presence of the detectably labelled thrombus.

BRIEF DESCRIPTION OF THE FIGURES

FIG. 5 (comprising FIGS. 5A and 5B) shows the chromogenic substrate assay comparing the catalytic activity of the recombinant protein with that of melanoma tPA.

Urokinase Constructs: pSVUKG(UK) contains the 59D8 VDJ exon, γ2b constant regions, the coding regions from a genomic clone of single-chain urokinase (scuPA) containing exons VII through XI, and a 3' UT sequence from the urokinase gene. Two modified chimeric genes were made by substituting either the 3' UT region of β-globin (pSVUKG(β)) or the 3' UT of the mouse γ2b Ig gene (pSVUKG(Ig)). pSVUKc(Ig) contains the 59D8 VDJ exon, the CH$_1$, CH$_2$ and H regions of the γ2b gene, cDNA coding for exons VII through XI of single chain urokinase, and a 3' UT sequence from the mouse γ2b Ig gene. These 4 plasmids, specifically pSVUKG(UK), pSVUKG(Ig), pSVUKG(β) and pSVUKc(Ig) all coded for r59D8-scuPA.

p220RX contains the 59D8 VDJ exon, the CH$_1$ and H regions of the γ2b gene, the coding regions from a genomic clone of single-chain urokinase (scuPA) containing exons VII through XI and a 3' UT sequence of the mouse γ2b IgG gene. p220RX codes for r59D8(—CH$_2$)-scuPA.

All genes were assembled in the pSV2gpt vector to form their respective expression plasmids. The pSV2gpt vector contained an SV-40 promoter-driven $Escherichia$ $coli$ xanthine guanine phosphoribosyl transferase (gpt) gene, serving as the selective marker in transfected hybridoma cells and a partial pBR322 sequence for plasmid replication and clone selection in *E. coli*.

Figure 8A:
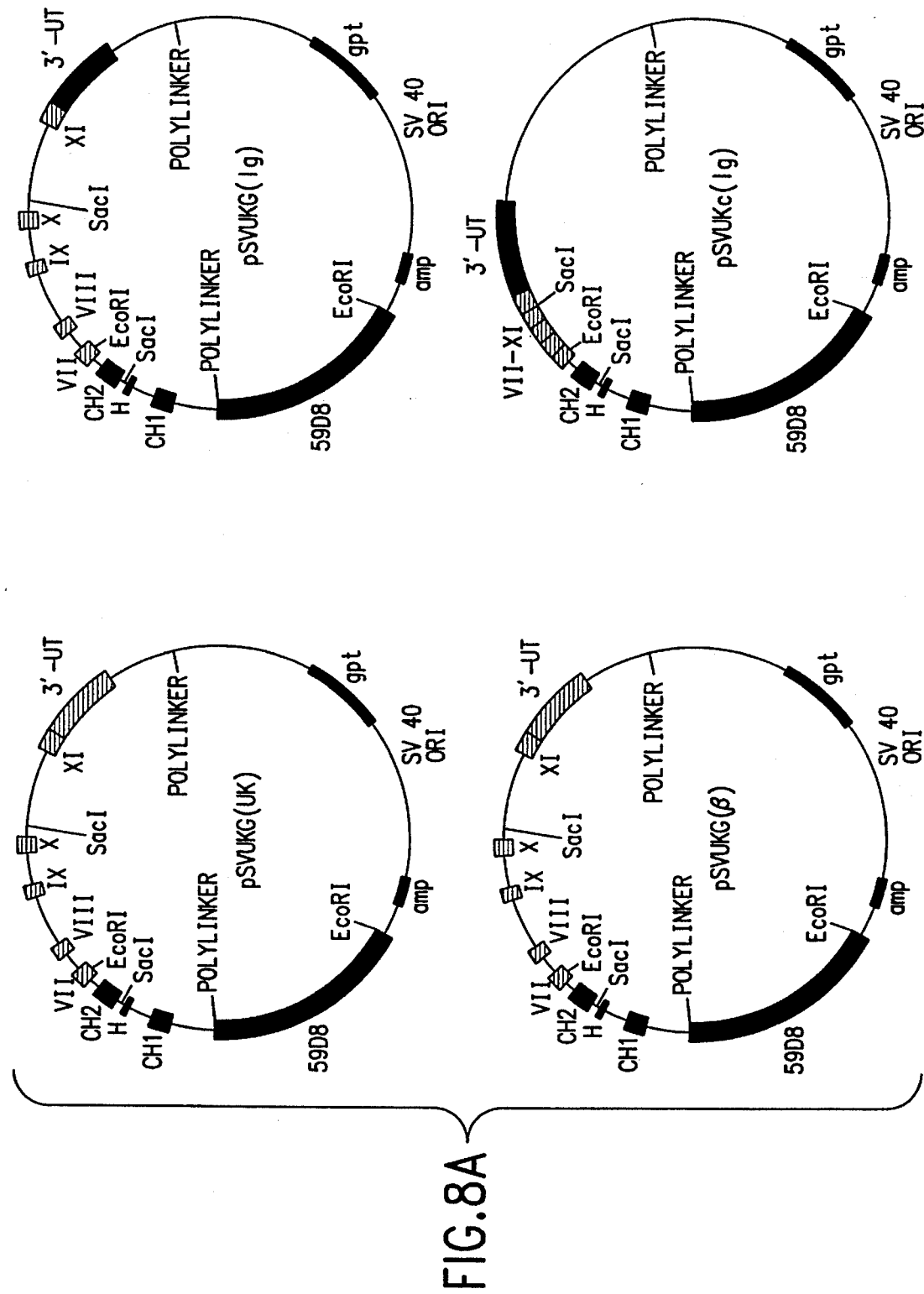
Figure 8B:
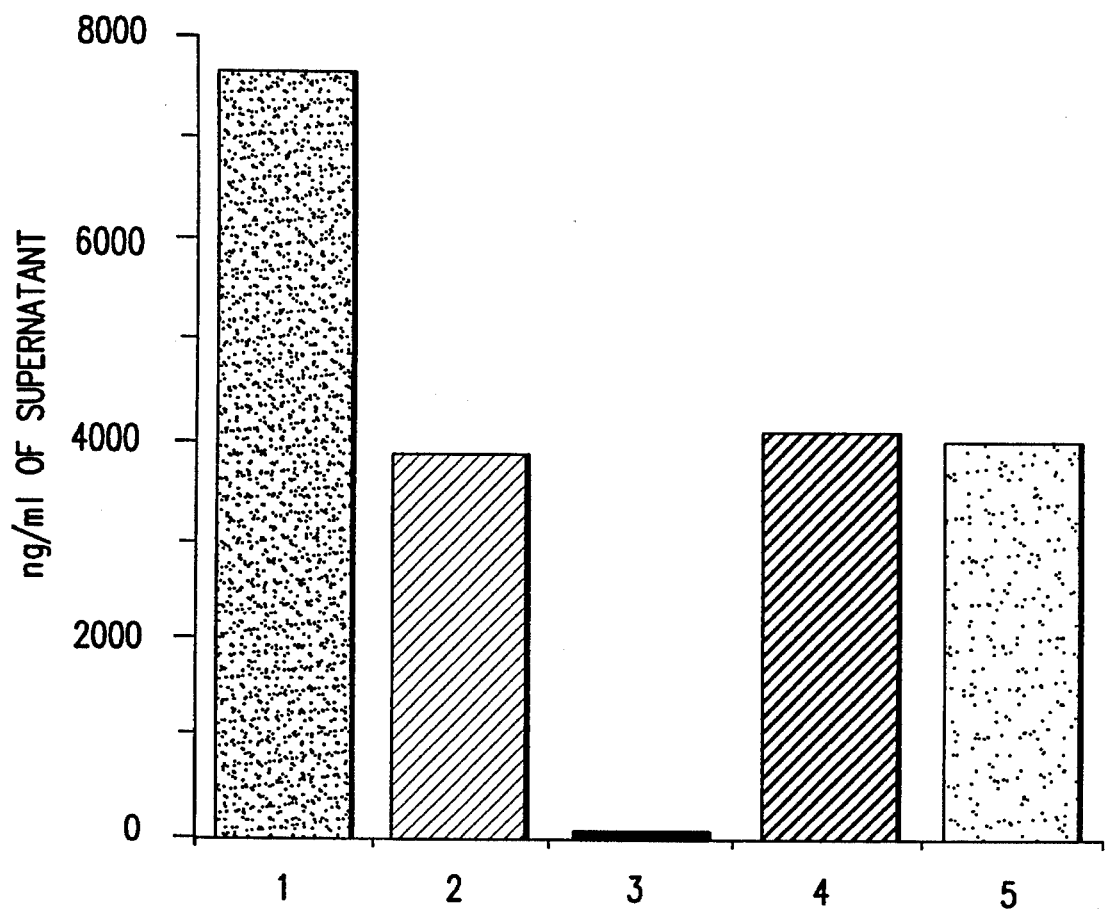

FIG. 8 (comprising FIGS. 8A and 8B) shows expression plasmids for r59D8-scuPA. FIG. 8A: pSVUKG(UK) contains a genomic heavy-chain variable region from fibrin-specific monoclonal antibody 59D8, cloned genomic constant region of the mouse γ2b (CH1, H (hinge) and CH2), and the coding region from a genomic clone of scuPA (containing exons VII through XI). In pSVUKG(UK) the 3' UT region is that of scuPA, beginning at Leu$^{144}$. Also contained in this plasmid are an SV-40 promoter-driver *Escherichia coli* xanthine guanine phosphoribosyl transferase (gpt) gene, serving as the selective marker in transfected hybridoma cells, and a partial pBR322 sequence for plasmid replication and clone selection in *E. coli*. Three modified plasmids were made by substituting either the 3' UT region of β globin (Lawn et al., *Cell* 21:647 (1980)) to form pSVUKG(β), or the 3' UT region of mouse immunoglobulin from antibody 59D8 to form pSVUKG(Ig). and pSVUKc(Ig). pSVUKc(Ig) also differed in that the genomic DNA encoding scuPA was replaced by cDNA encoding the same region (exons VII through XI).

FIG. 8B: Protein expression levels. Stable, subcloned heavy-chain loss variant mouse L2LV cells derived from hybridoma cells producing native 59D8 (Schnee et al., *Proc. Natl. Acad. Sci. USA* 84:6904 (1987); Love et al., In *Methods in Enzymology*, Langone, J. J. (ed.), Academic Press, New York, pp. 515–527 (1989))) were harvested at log phase and were transfected with linearized plasmid (20 μg/1.0 ml of cell suspension) by electroporation (200 volts and 960 μFD). Stable clones were selected and cloned and the cells were grown to confluence in 100-ram petri dishes. The supernatants were harvested at equal cell densities. The ng/ml values for supernatants were based on the presence of mouse immunoglobulin measured by reference to a standard curve. Results represent the means of duplicate determinations. Samples were: (1) supernatant from 59D8 cells; (2) supernatant from γ2b cells (heavy-chain loss variant cells that had been transfected with an expression plasmid encoding only the heavy chain of antibody 59D8); (3) supernatant from pSVUKG(UK); (4) supernatant from pSVUKG(β); and (5) supernatant from pSVUKG(Ig).

Figure 9A:
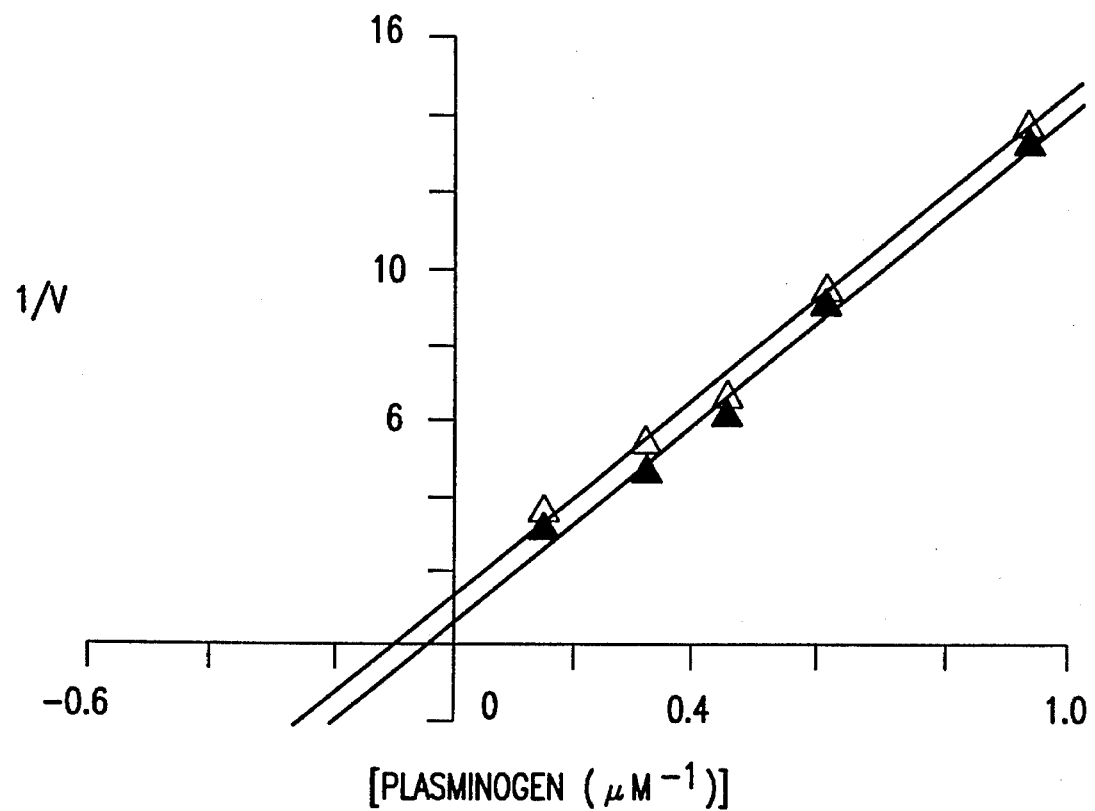
Figure 9B:
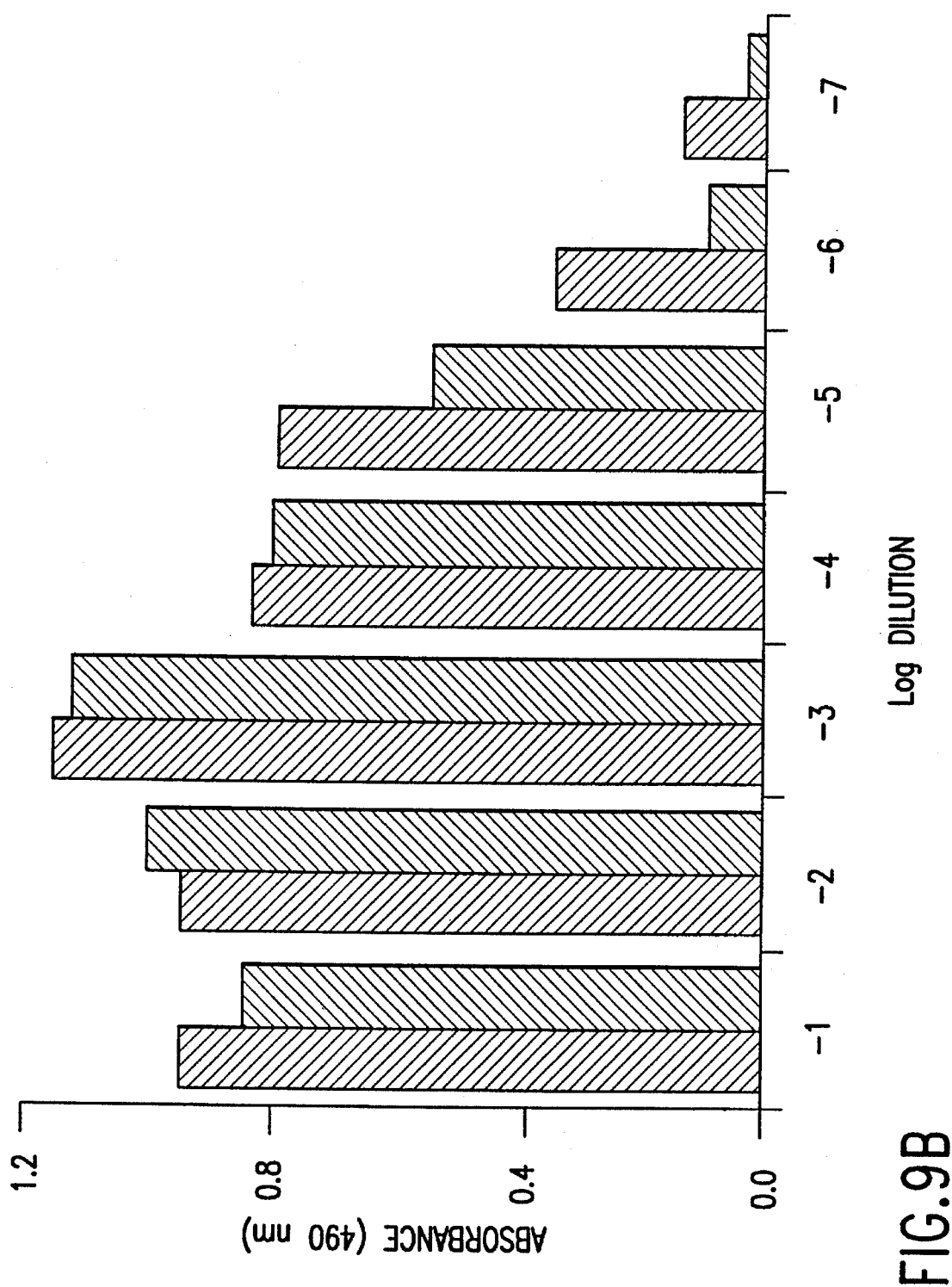

FIG. 9 (comprising FIGS. 9A and 9B) shows kinetic and fibrin binding properties of r59D8-scuPA. FIG. 9A: Initial rates of reaction for two-chain urokinase (Abbott Laboratories, Abbott Park, Ill.) and the two-chain form of r59D8-scuPA were measured by changes in absorbance at 405 nm resulting from the cleavage by plasmin of S-2251 (Helena Laboratories, Beaumont, Tex.). The protocol was adapted from that of Dewerchin et al. (*Eur. J. Biochem.* 185:141 (1989)). Points represent the means of duplicate determinations. Their general pattern was reproduced in several different experiments. Data obtained for urokinase (open triangles) and the two-chain form of r59D8-scuPA (filled triangles) did not significantly differ.

FIG. 9B: Fibrin binding by native 59D8 (stippled bars) and r59D8-scuPA (hatched bars). ELISA plates (96-well were coated with fibrin monomer (5 μg/ml). After blocking, samples of either 59D8 or r59DS-scuPA were incubated on the plates. Serial dilutions of 59D8 or r59D8-scuPA ranged between $1.7 \times 10^{-3}$ and $1.7 \times 10^{-6}$ mg of antibody/ml for one hour to allow binding. The wells were washed extensively with Tris-saline (pH 8, with 0.05% Tween-20) and were blocked again with bovine serum albumin (BSA). The wells were then probed with a Fab'$_2$ preparation of polyclonal rabbit anti-mouse IgG antibodies that had been labeled with biotin. Then the plates were treated with ELISA-amplification reagents (Bethesda Research Laboratories, Bethesda, Md.) to obtain a color reaction. The means of duplicate determinations are shown.

Figure 10A:
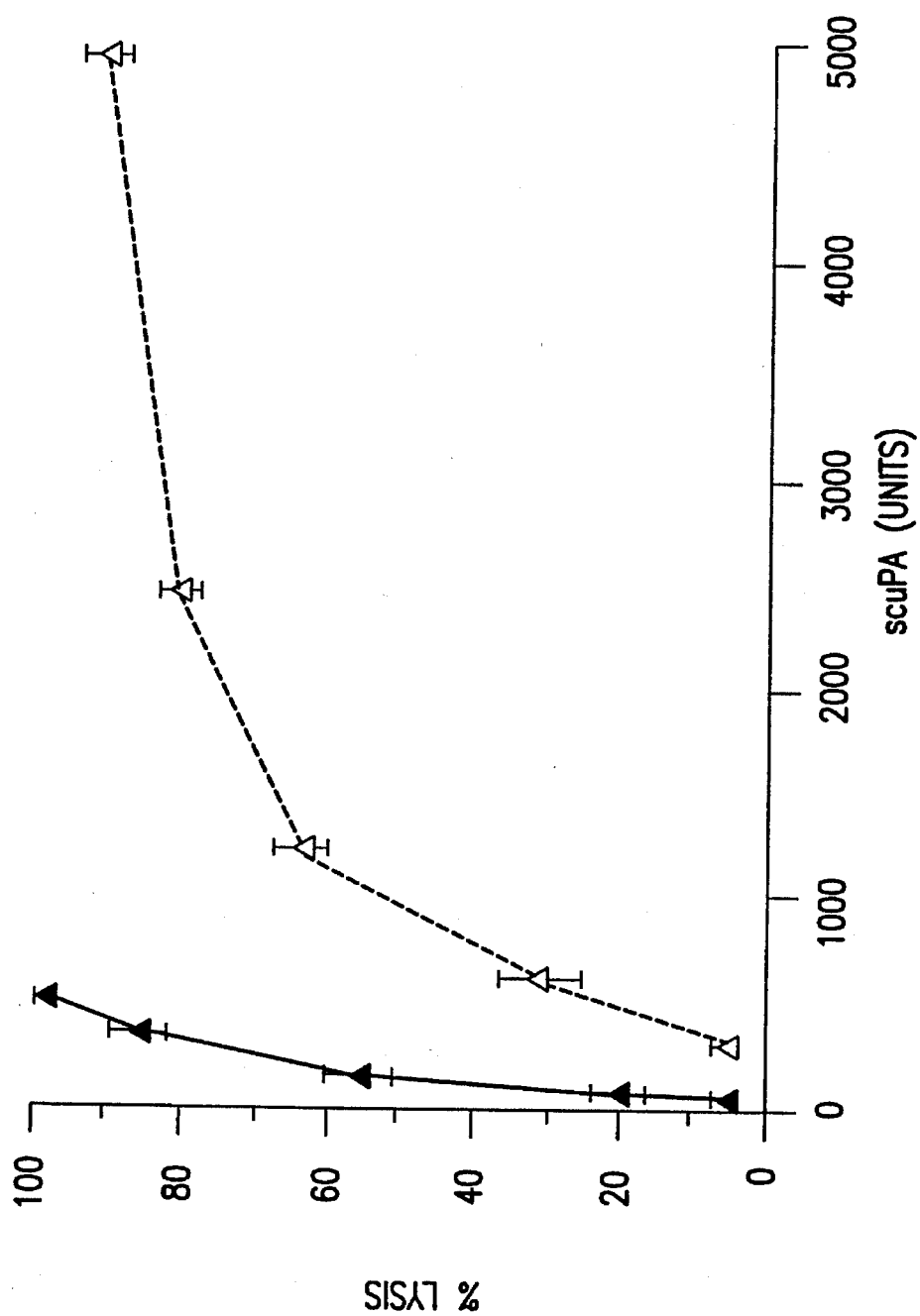
Figure 10B:
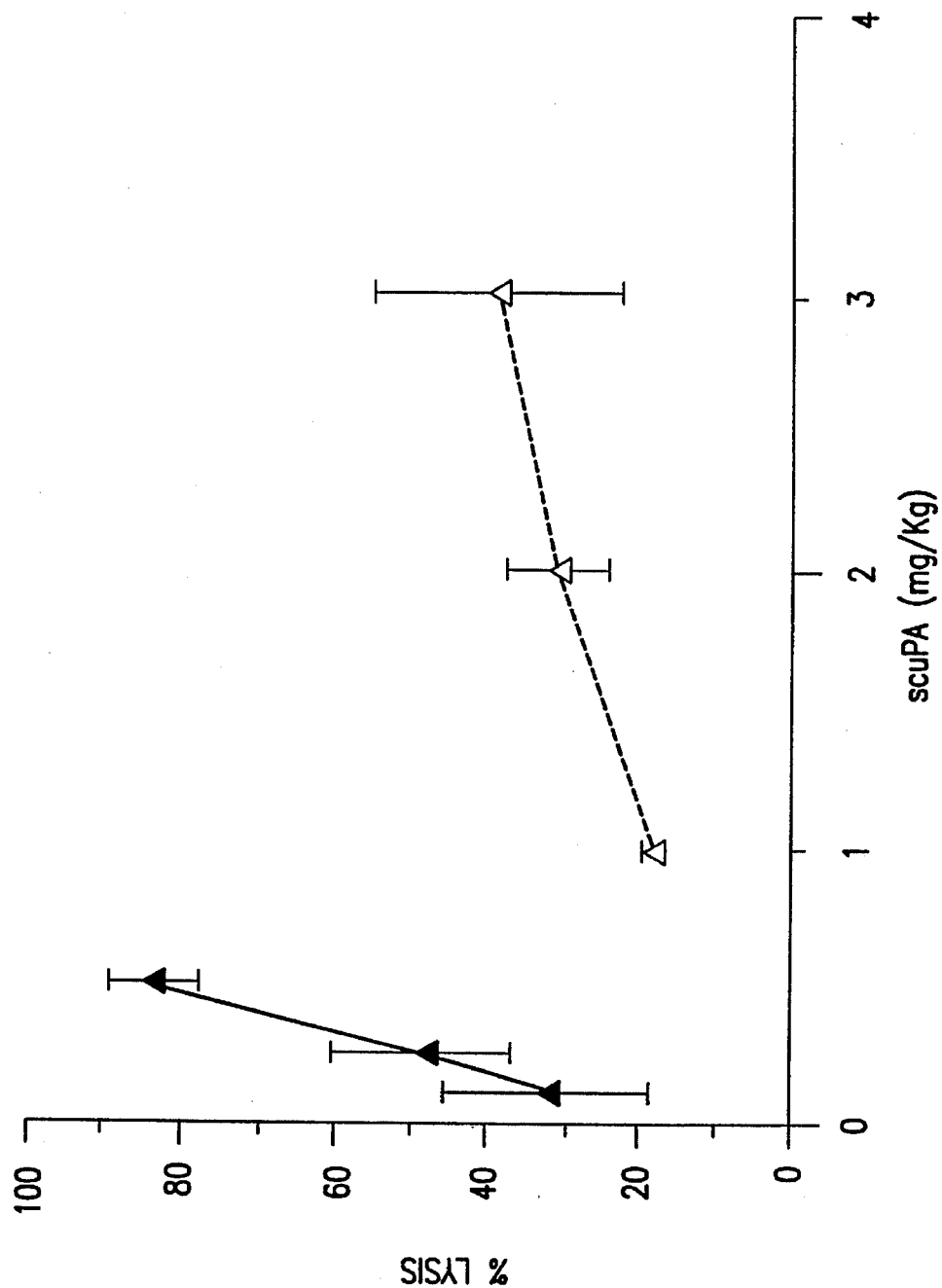

FIG. 10 (comprising FIGS. 10A and 10B). FIG. 10A shows results from a human plasma clot lysis assay, performed as described by Bode et al. (*Circulation* 181:1974 (1990)) which was based on Runge et al. (*Biochemistry* 27:1153 (1988)). PA concentrations were based both on protein concentration and S-2444 activity (see above). Points represent clot lysis at 2 hours. The increase in potency was calculated by fitting the percent lysis curves in the plasma clot and rabbit jugular vein assays to anti-logic functions of two parameters (estimated) that have been shown to fit curves of percent lysis versus dose of PA (Bode et al., *J. Mol. Cell. Cardiol.* 19:335 (1987)). Open triangles represent scuPA data. Filled trangles represent r59D8-scuPA data.

FIG. 10B demonstrates thrombolysis in vivo. The rabbit jugular vein model of Collen et al. (*J. Clin. Invest.* 71:368 (1983)) was modified as described by Runge et al. (*Proc. Natl. Acad. Sci. USA* 84:7659 (1987)) and Collen et al. (*Fibrinolysis* 3:197 (1989)). PAs (or saline) were administered by infusion of a bolus (20% of the total dose) over one minute, along with a heparin bolus (300 units/kg) over one minute, followed by continuous infusion over the next sixty minutes of the remainder of the PA dose and of heparin over the next 180 minutes (60 units/kg/hour). The animals were killed after this three-hour treatment and the amount of thrombolysis was measured by gamma counting of the remaining vein segment. Data represent the means of values from between 3 and 8 animals at each point. The 20-fold increase in potency for r59D8-scuPA was derived as described, above, in connection with FIG. 10A.

Figure 11:
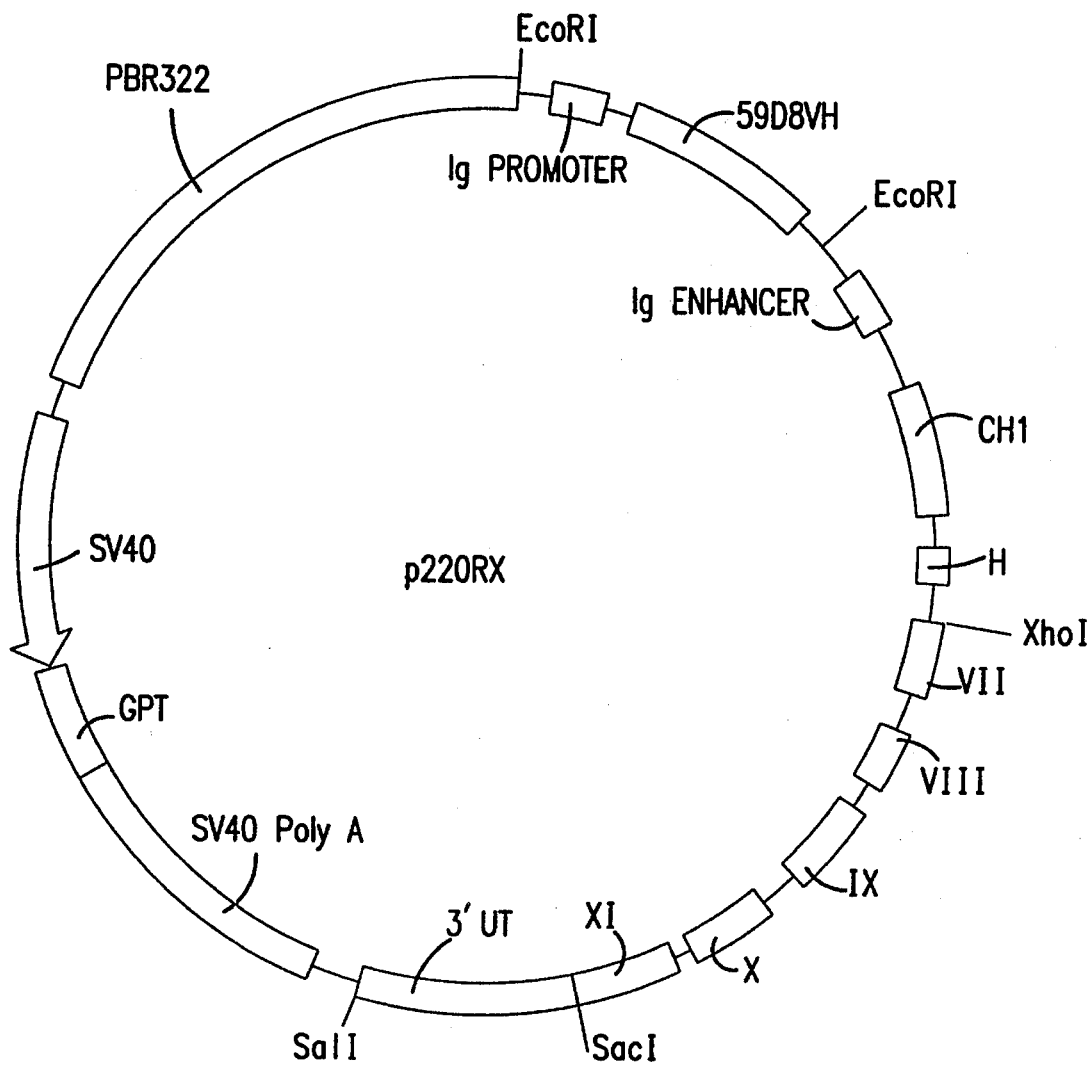
Figure 12A:
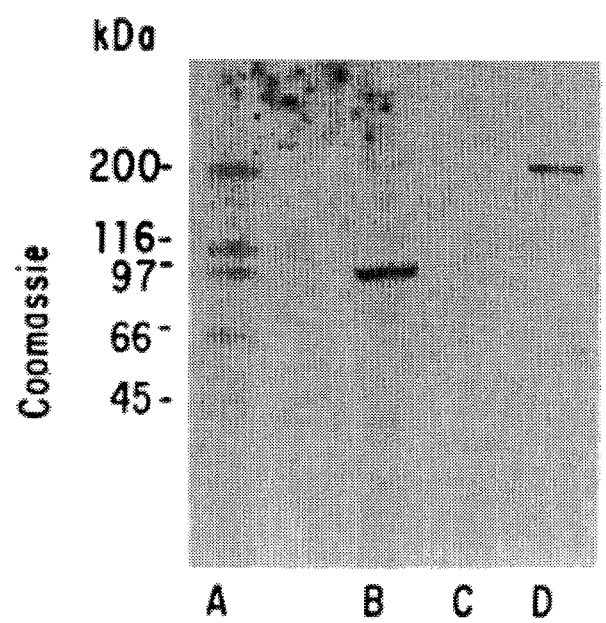
Figure 12B:
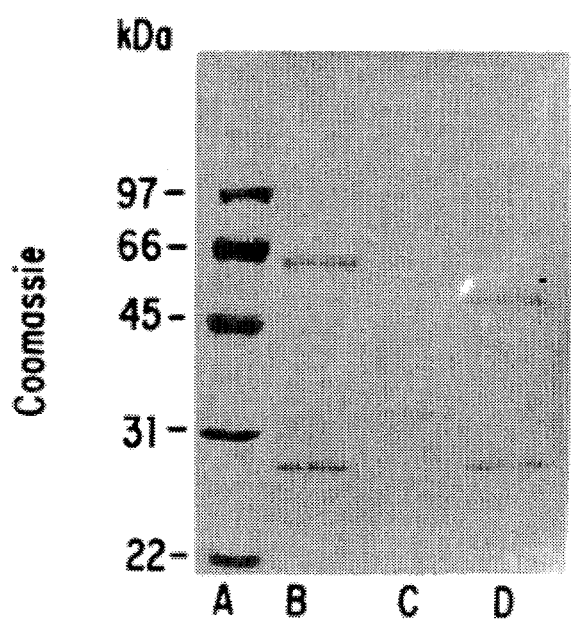
Figure 12C:
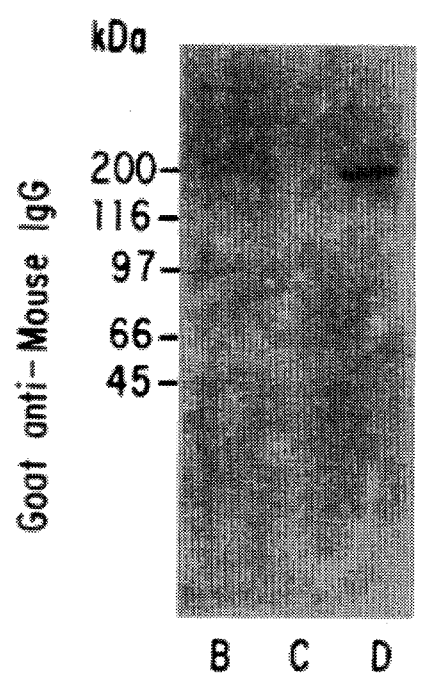
Figure 12D:
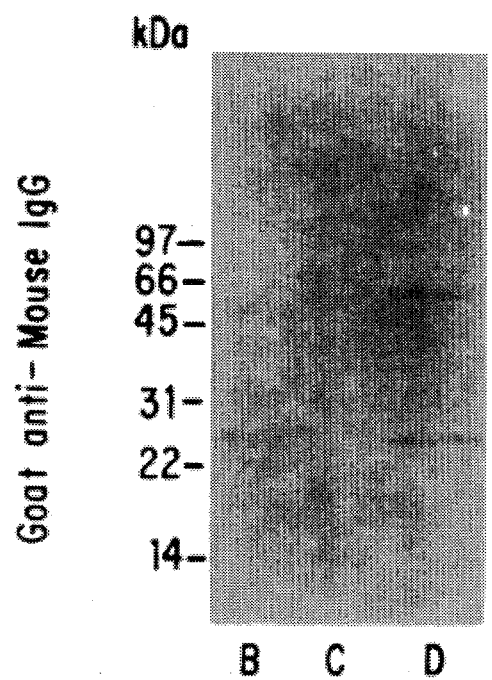
Figure 12E:
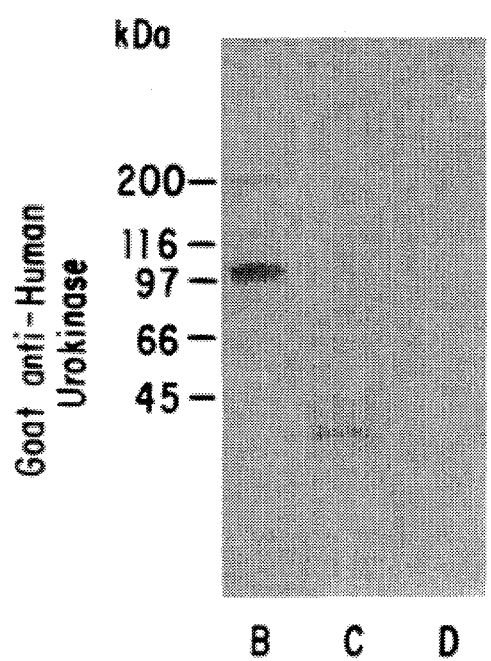
Figure 12F:
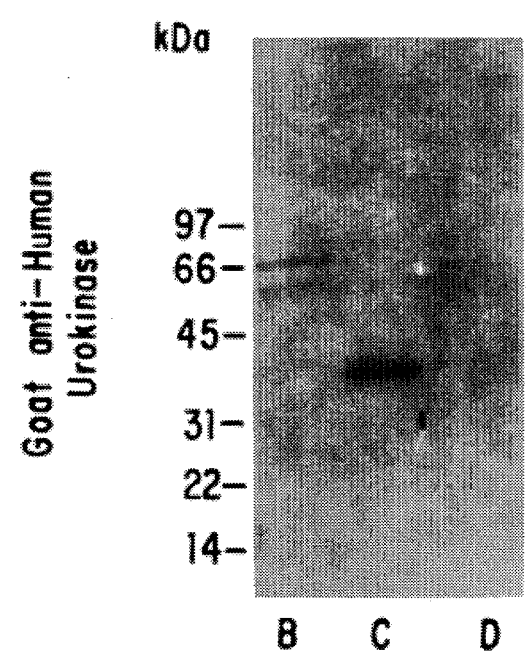

FIG. 11: A map of plasmid p220RX that expressed recombinant protein r59D8(—CH$_2$)-scuPA, also known as AFA-scuPA. This plasmid was constructed by deletion of the CH$_2$ fragment from plasmid pSVUKG(Ig).

FIG. 12A–F: Analysis of r59D8(—CH$_2$)-scuPA isoform lacking the Fc domain. Affinity purified r59D8(—CH$_2$)-scuPA was analyzed by SDS-PAGE using Coomassie blue staining (FIG. 12A–B) or western blotting using either goat anti-mouse IgG (FIG. 12C–D) or goat anti-human urokinase (FIG. 12E–F) antibodies obtained from American Diagnostica. In each of the six panels the following apply: Lane A is protein standard; lane B is r59D8(—CH$_2$)-scuPA; lane C is low molecular weight UK; and lane D is antibody 59D8.

FIG. 13 (comprising FIGS. 13A, 13B and 13C): The thrombolysis device designed for these studies. FIG. 13A: Diagrammatic representation of the accumulation of platelet-rich thrombotic material collecting within the thrombogenic Dacron vascular graft and of the formation of a fibrin-rich thrombus distal to the Dacron graft under the conditions described here. Arrows indicate the direction of blood flow. FIG. 13B: $^{111}$In-platelet imaging at 10, 20, 30 and 40 min after the initiation of flow. Platelet deposition occurred first within the Dacron graft segment, but was soon followed by accumulation within the fibrin-rich tail. FIG. 13C: Quantitation of platelet deposition in the presence of heparin but in the absence of a PA indicated the formation of a stable non-occlusive thrombus.

Figure 14A:
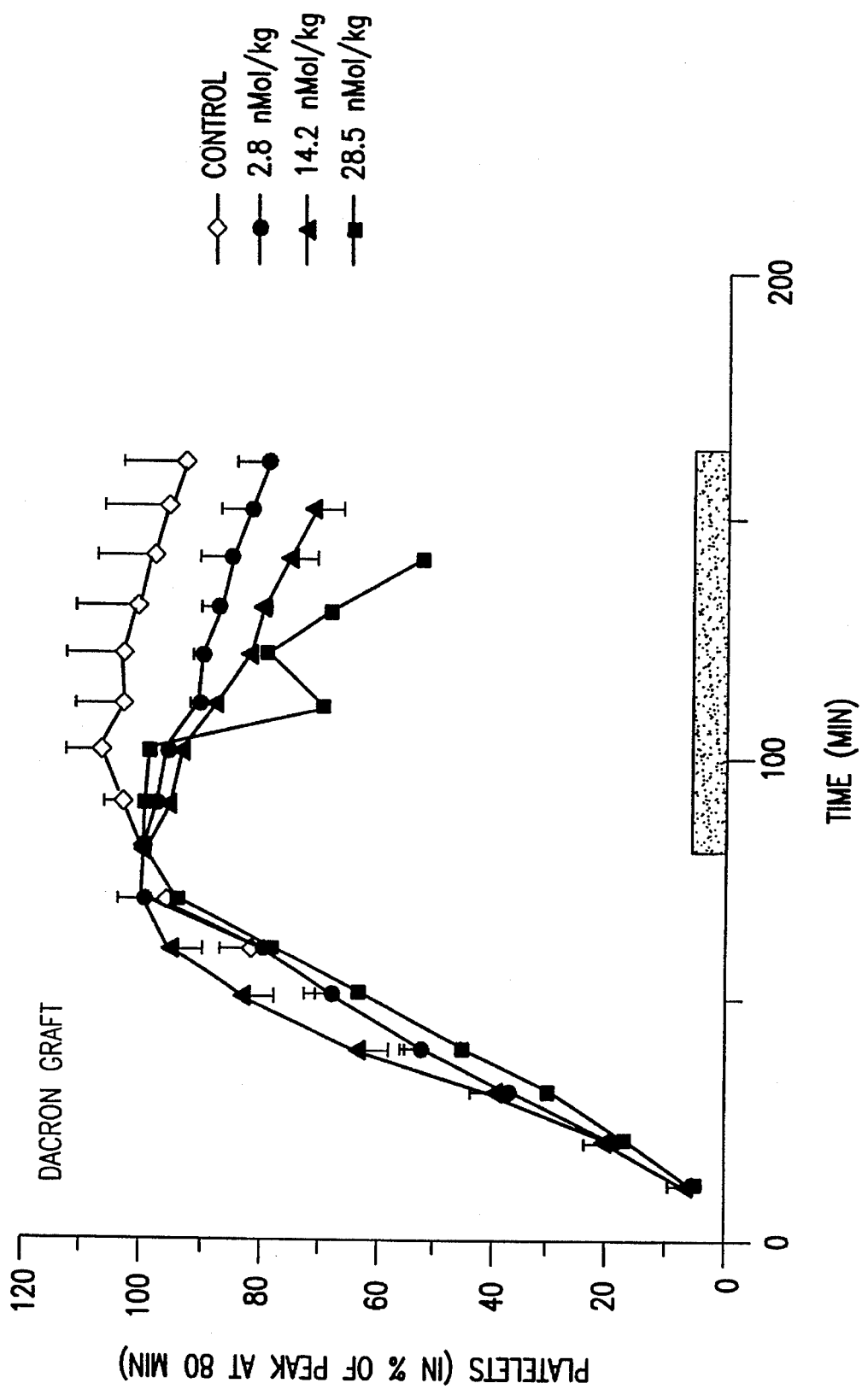
Figure 14B:
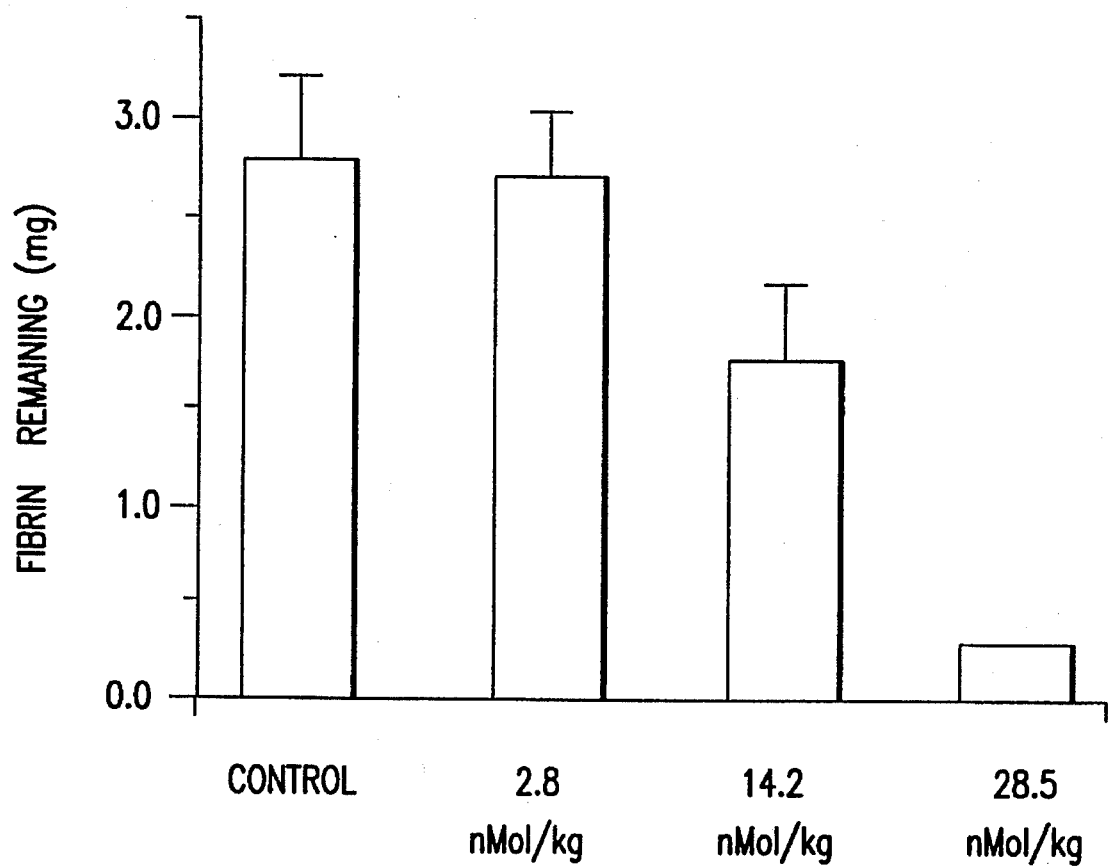
Figure 14C:
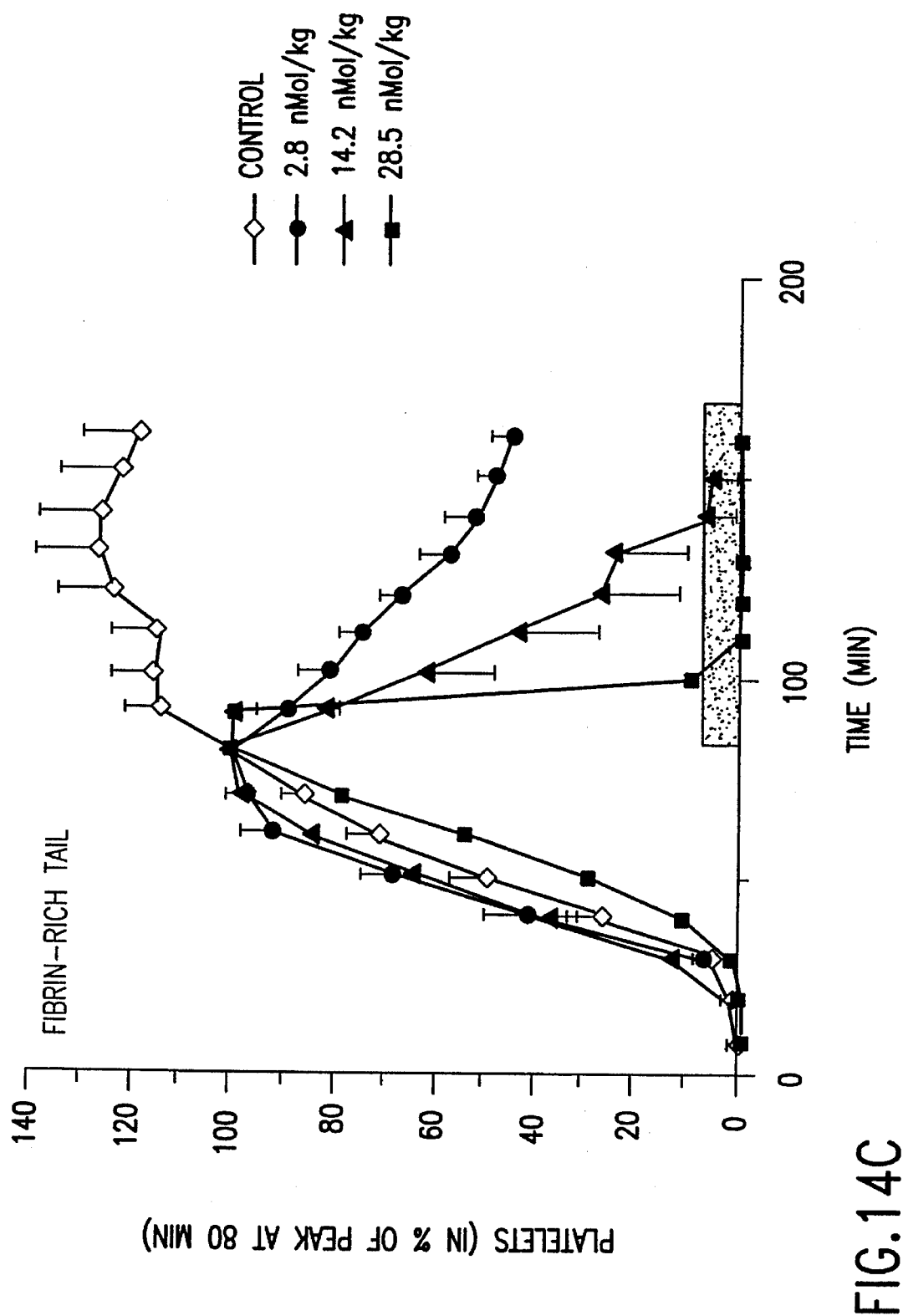

FIG. 14 (comprising FIGS. 14A, 14B and 14C): Thrombolysis in vivo by rtPA. The effects of doses of rtPA as measured by $^{111}$In-labeled platelet imaging following initiation of therapy. FIG. 14A: Dacron vascular graft segment (platelet-rich thrombotic material). FIG. 14B: Loss of $^{125}$I-fibrin from the Dacron vascular graft segment over the same dosage range. FIG. 14C: Fibrin=rich tail. In these dose response studies the doses used for rtPA were: 2.85 nMol/kg (closed circles), 14.2 nMol/kg (closed triangles) or 28.5 nMol/kg (closed squares). Open diamonds represent controls in each figure. Each point represents the mean of determinations in 4–6 different baboons. Error bars show the standard errors of the means. The stippled horizontal bars in FIGS. 14A and 14C indicate the time during which a plasminogin activator was infused.

Figure 15A:
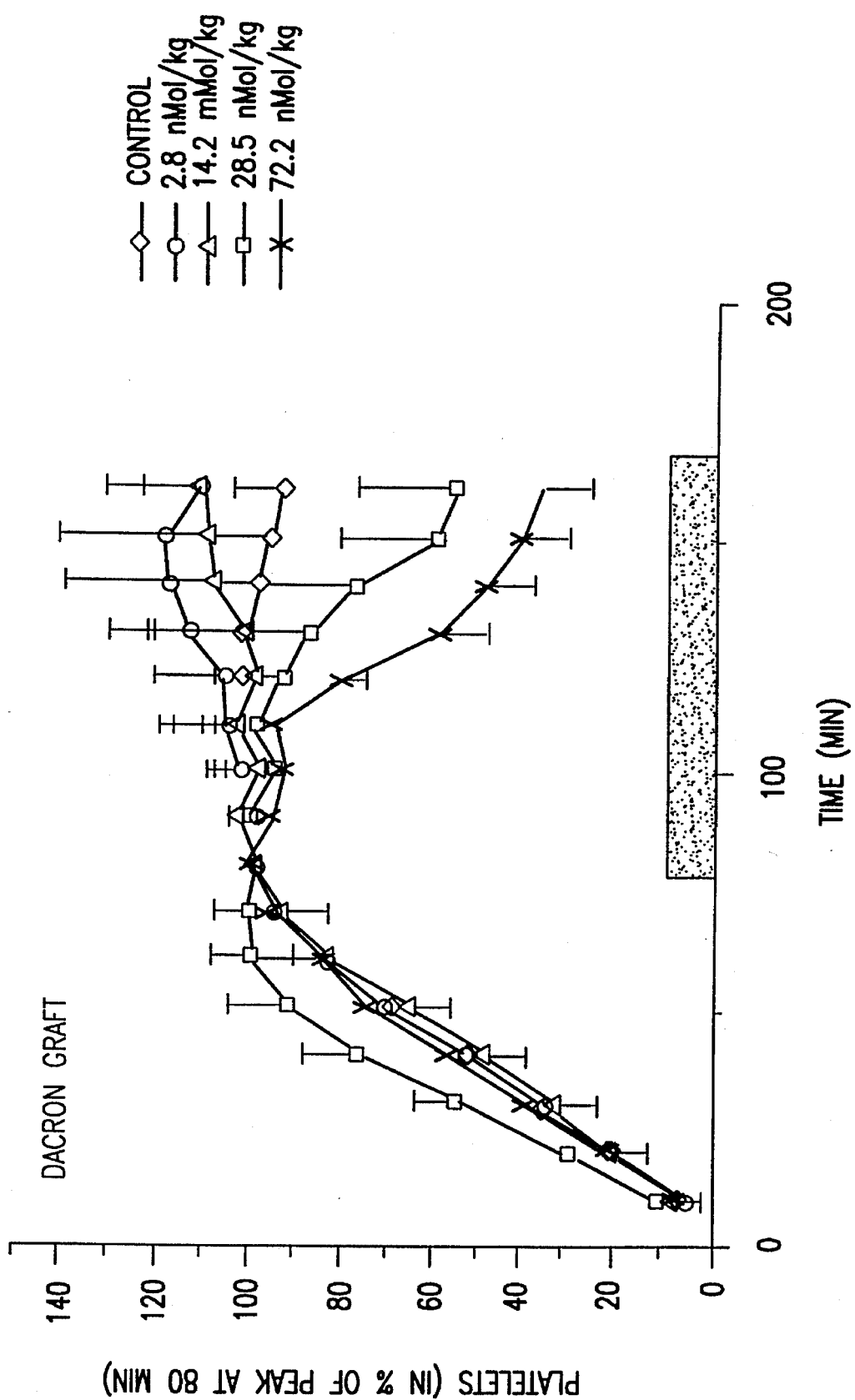
Figure 15B:
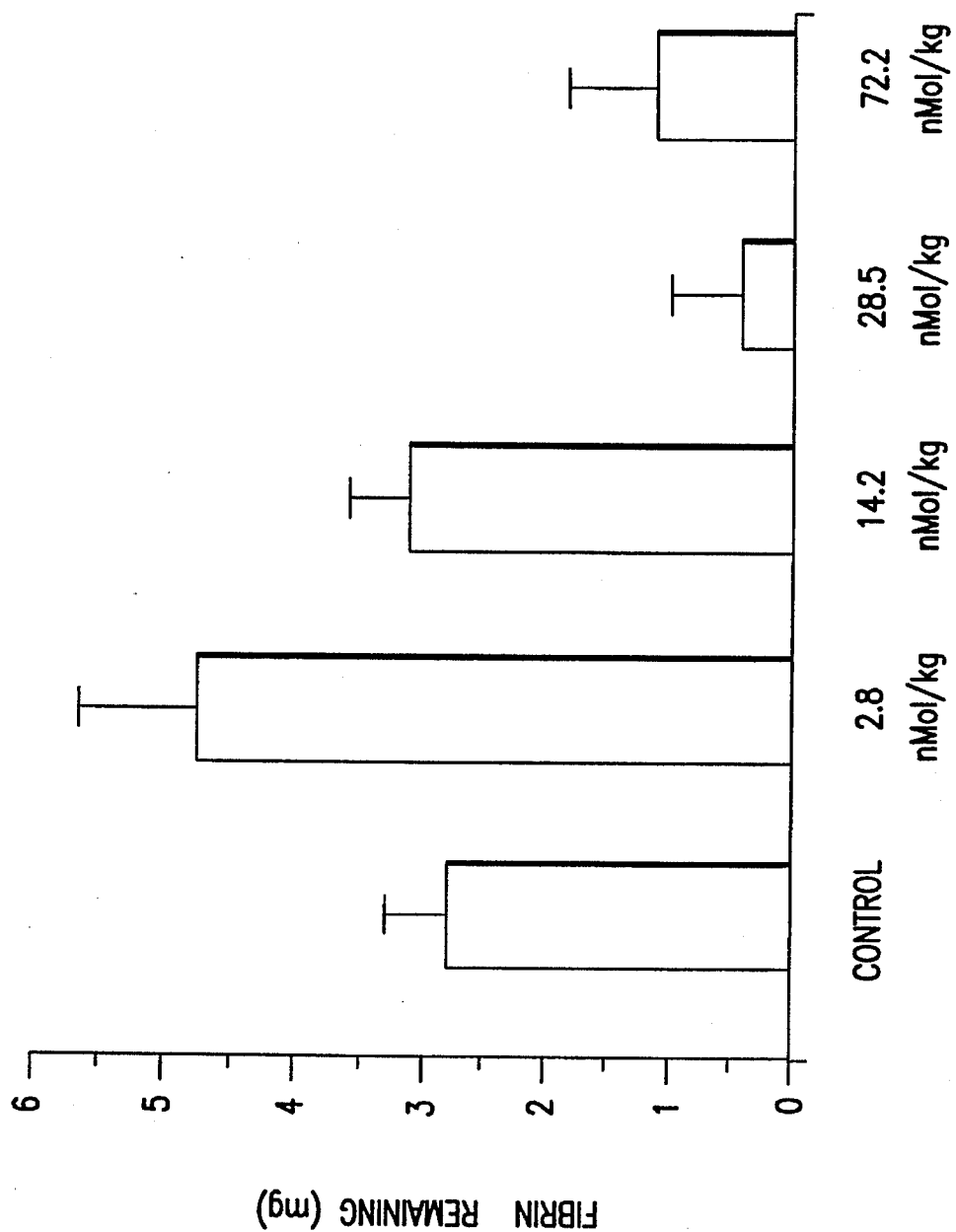
Figure 15C:
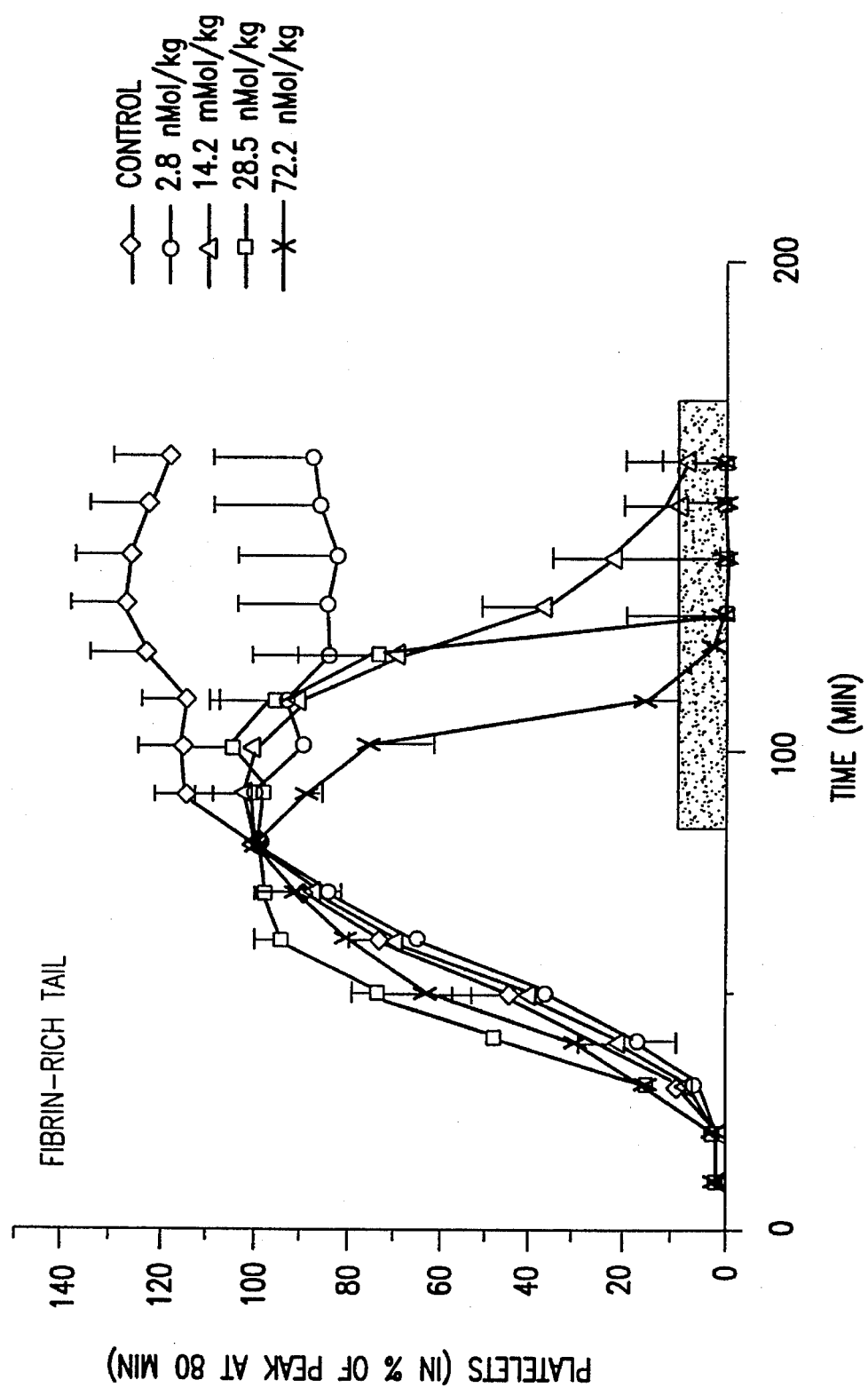

FIG. 15 (comprising FIGS. 15A, 15B and 15C): Thrombolysis in vivo by rscuPA. The effects of increasing doses of rscuPA as measured by $^{111}$In-labeled platelet imaging following initiation of therapy. FIG. 15A: Dacron vascular graft segment (platelet-rich thrombotic material). FIG. 15B: Loss of $^{125}$I-fibrin from the Dacron vascular graft segment is shown over the same dosage range. FIG. 15C: Fibrin-rich tail. The doses of rscuPA used were 2.85 nMol/kg (open circles), 14.2 nMol/kg (open triangles), 28.5 nMol/kg (open squares), or 72.2 nMol/kg (▶◀). Open diamonds represent the controls. Each point represents the means of determinations in 4–6 different baboons. Error bars show the standard errors of the means. The stippled horizontal bars in FIGS. 15A and 15C indicate the time during which a plasminogin activator was infused.

Figure 16A:
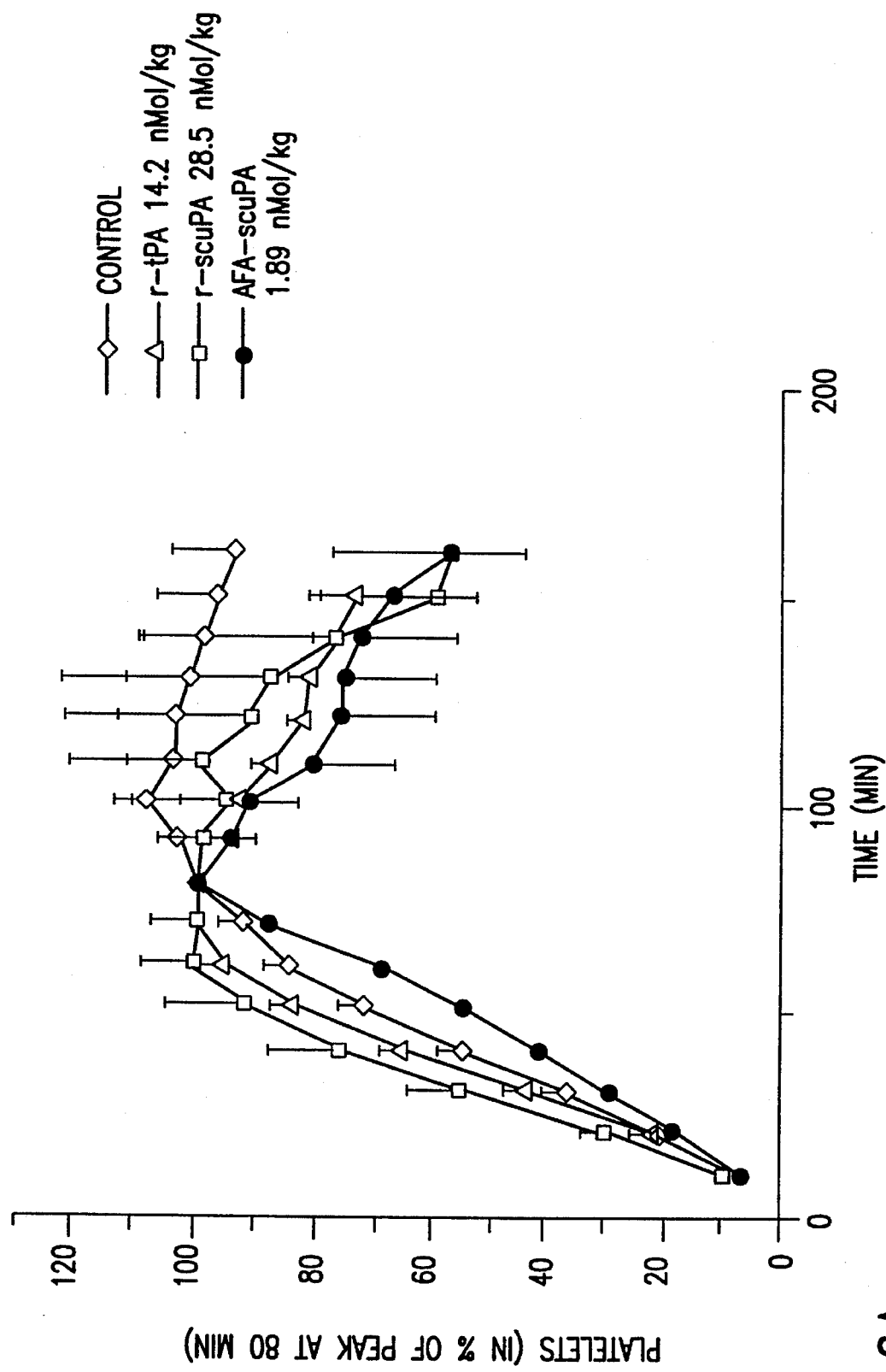
Figure 16B:
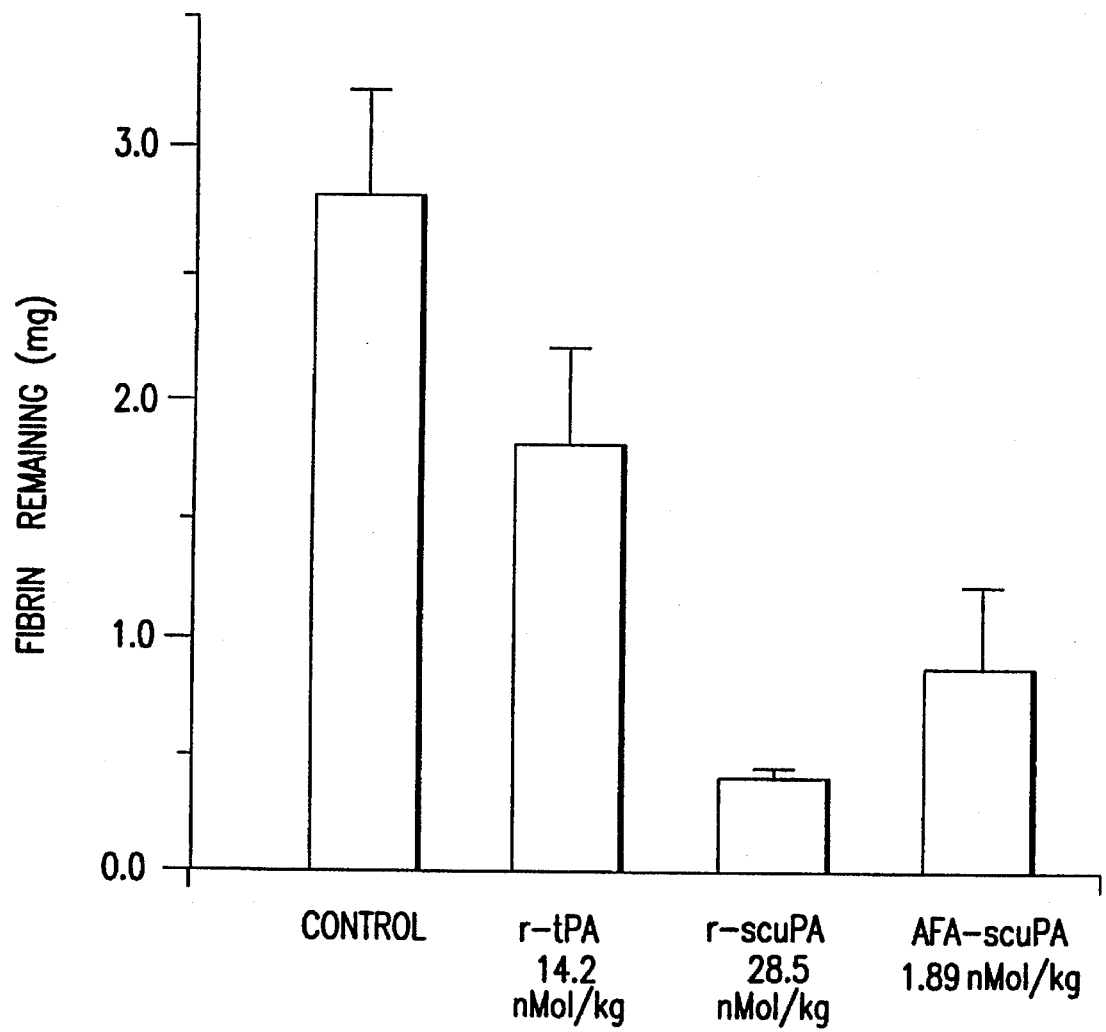
Figure 16C:
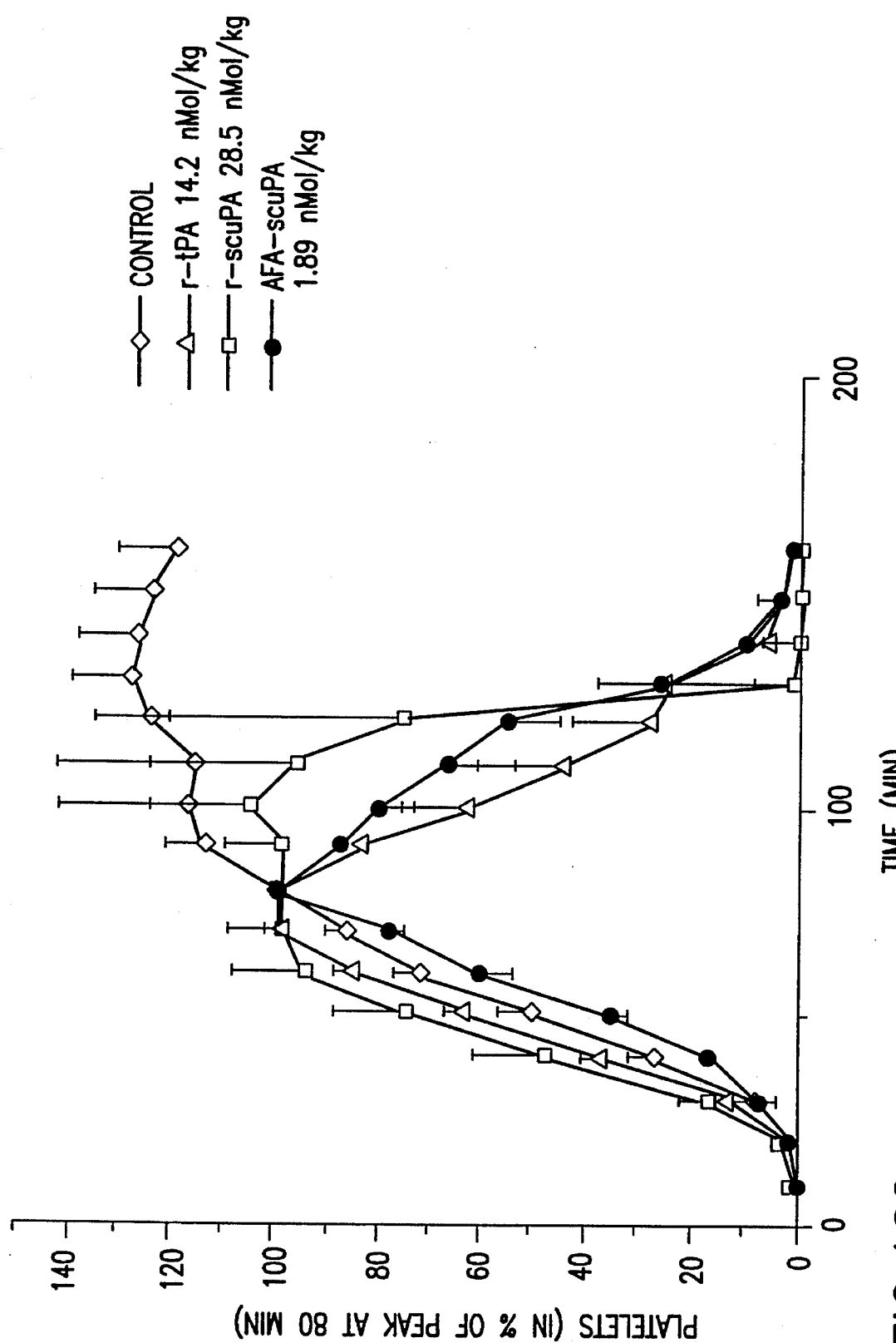

FIG. 16 (comprising FIGS. 16A, 16B and 16C): Comparison of thrombolytic potencies of rtPA, rscuPA and r59D8(—CH$_2$)-scuPA in vivo. $^{111}$In-labeled platelet imaging following initiation of therapy is shown with selected doses of each PA for thrombolysis in the Dacron vascular graft segment in platelet-rich thrombotic material (FIG. 16A) and in the fibrin-rich tail (FIG. 16C). Loss of $^{125}$I-fibrin from the Dacron vascular graft segment is shown over the same dosage range (FIG. 16B). The following doses were selected as equipotent: rtPA, 14.2 nMol/kg (open triangles); rscuPA, 28.5 nMol/kg (open squares); and r59D8(—CH$_2$)-scuPA, 1.89 nMol/kg (solid circles). In each panel the control data show the effect observed when only heparin was administered. Each point represents the means of determinations in 4–6 different baboons.

Figure 17:
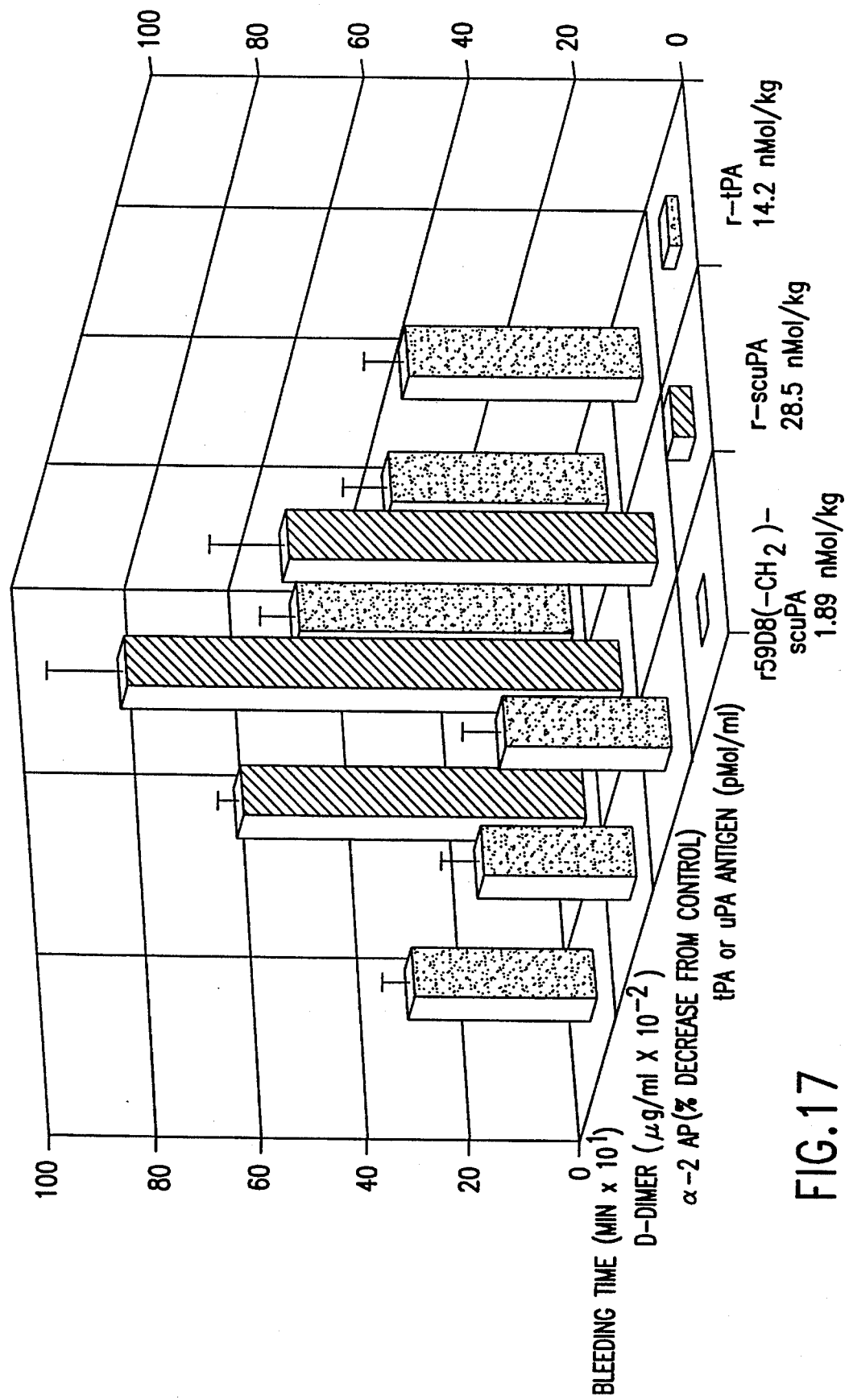

FIG. 17: Effects of comparable thrombolytic doses of r59D8(—CH$_2$)-scuPA (light stipling), rscuPA (hatched) and rtPA (heavy stipling) on α-2-antiplasmin levels, D-dimer levels, and template bleeding times were determined. The plasma concentrations of 59D8(—CH$_2$)-scuPA, rscuPA and rtPa at the doses administered are shown as "tPA or uPA antigen (pMol/ml)." Measured levels are shown according to the units described. Error bars represent standard deviations.

Figure 18A:
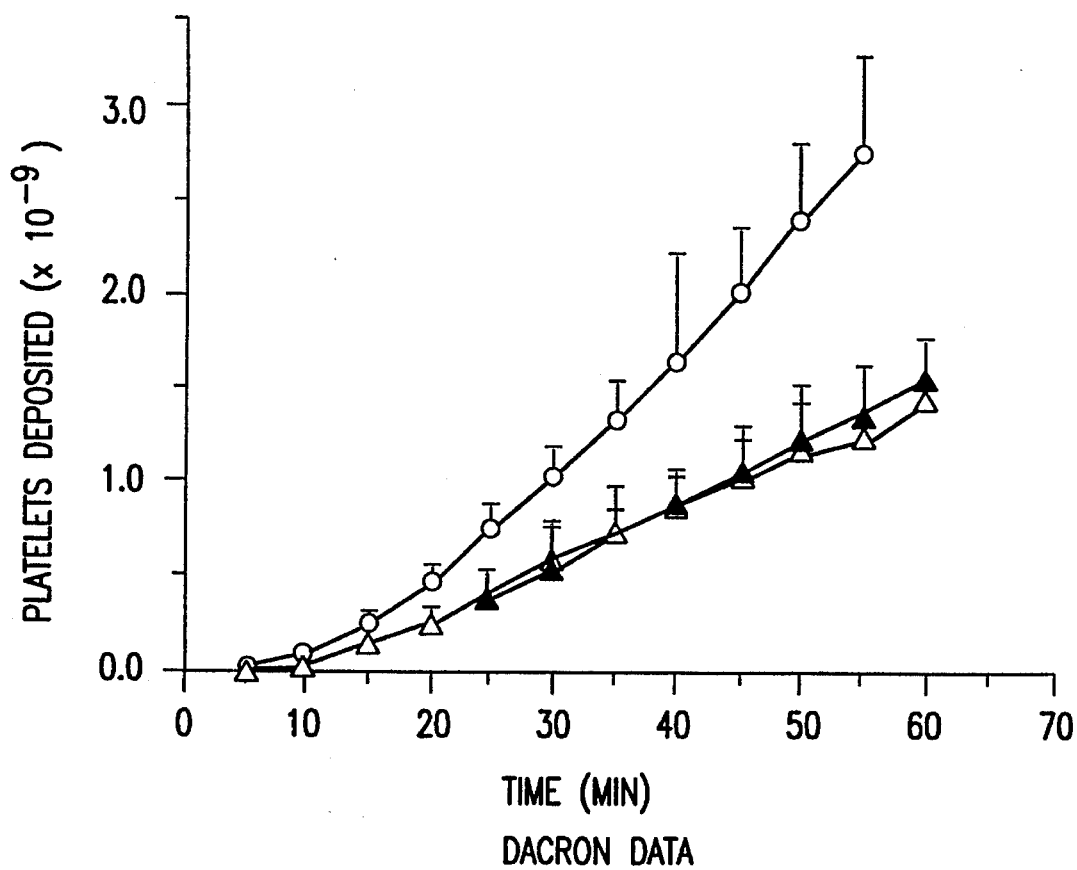
Figure 18B:
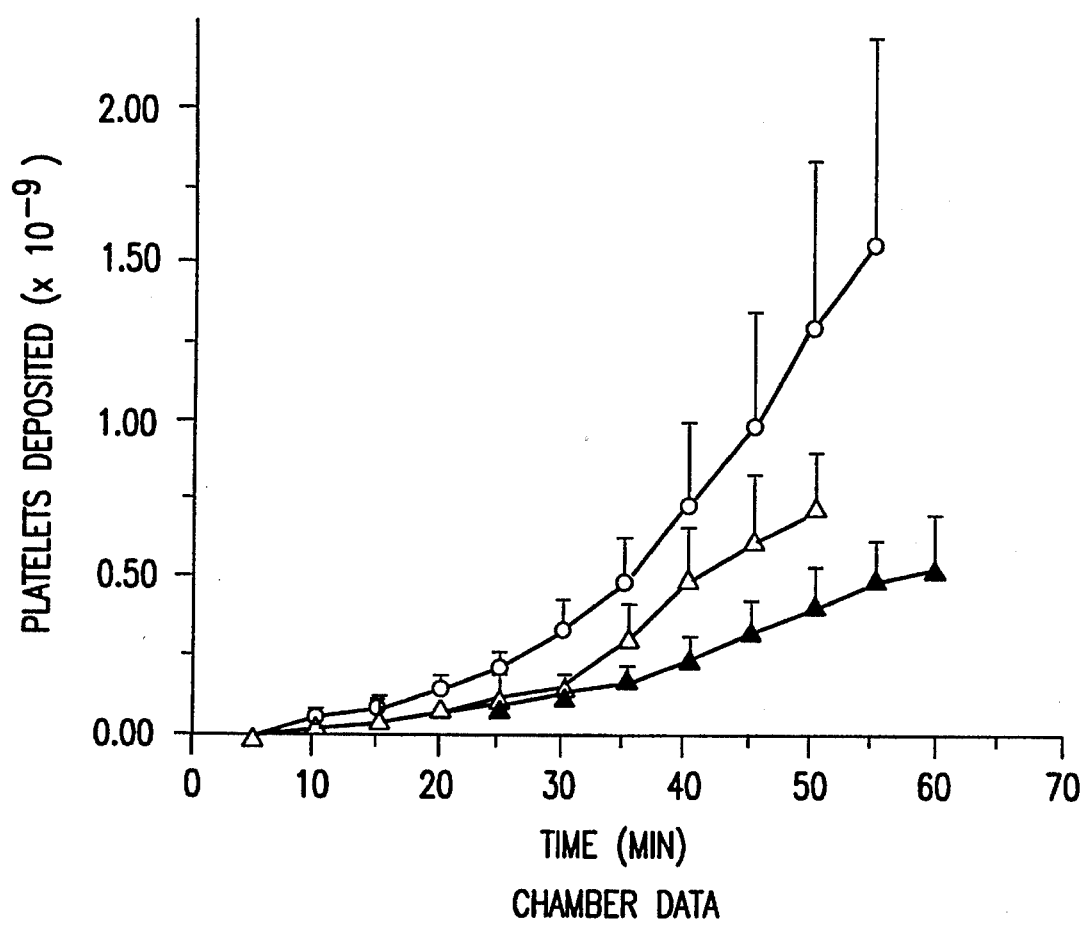

FIG. 18 (comprising FIGS. 18A and 18B): Inhibition of thrombus formation by rscuPA and r59D8(—CH$_2$)-scuPA. Thrombus accretion was measured as described in Materials and Methods (controls=open circles). The effects of rscuPA (3.7 nMol/kg/hr; open triangles) and r59D8(—CH$_2$)-scuPA (0.31 nMol/kg/hr; closed triangles), administered over 60 min, were measured. Each point represents the means and standard deviations of 4–6 separate measurements. FIG. 18A shows platelet-rich thrombus accretion in a segment of Dacron vascular graft. FIG. 18B shows fibrin-rich thrombus accretion in a low flow expansion chamber.

DEFINITIONS

In order to provide a clear and consistent understanding of the specification and claims, including the scope to be given such terms, the following definitions are provided. Any terms which are not specifically defined in this or other sections of this patent application have the ordinary meaning they would have when used by one of skill in the art to which this invention applies.

As used herein, "hybrid immunoglobulin-enzyme molecule" means a molecule that comprises: (1) all, or a portion of, an antibody including the variable region thereof which specifically binds an epitope that is specific for either a venous or arterial thrombus; and (2) all, or a portion of, an enzyme molecule which possesses thrombolytic activity; (3) wherein the antibody and enzyme portions of the hybrid immunoglobulin molecule are operably linked together. Any antibody, or fragment or derivative thereof, that specifically binds an epitope which is specific for either a venous or arterial thrombus can be used to produce the molecules of this invention. These antibodies may be of the IgG, IgA, IgM, IgD or IgE type. Preferably they are IgG molecules or fragments or derivatives thereof. Complete antibody molecules do not have to be used to form the hybrid molecules of this invention. Fragments or derivatives of antibody molecules may be used as long as the fragment or derivative specifically binds an epitope that is specific for either a venous or arterial thrombus. For example, these antibodies, or derivatives or fragments thereof, can specifically bind to: fibrin epitopes other than those recognized by monoclonal antibodies (MAbs) 59D8 and 64C5; platelet activation epitopes, including glycoprotein IIb/IIIa, LIBS, etc.; other platelet specific epitopes, such as the thrombin receptor; and thrombin itself.

As used herein, "fibrin specific" means that antibodies, or derivatives or fragments thereof, specifically bind to fibrin but do not substantially bind to other molecules.

As used herein, "specifically binds fibrin" means that the antibody, or derivative or fragment thereof, including hybrid immunoglobulin-enzyme molecules, selectively bind fibrin.

As used herein, fibrin epitopes that may be used in this invention to bind to fibrin specific antibodies include, but are not limited to, the amino terminus of the fibrin beta chain, the amino terminus of the fibrin alpha chain, the beta (43–49) amino acid sequences, which are carboxy-terminal to a plasmin cleavage site, and the gamma chain crosslink site. Antibodies with fibrin specificity are described in commonly assigned, formerly co-pending United States application, Ser. No. 824,228, filed Jan. 30, 1986, now U.S. Pat. No. 4,927,916, for "Fibrin-Specific Monoclonal Antibodies Lacking Fibrinogen Cross-Reactivity." Fibrin-specific monoclonal antibodies with essentially no fibrinogen cross-reactivity are also described in commonly assigned, formerly co-pending, United States patent application Ser. No. 851,514, filed Apr. 14, 1986 (U.S. Pat. No. 4,916,070).

As used herein, "operably linked" means that the antibody-derived and thrombolytic enzyme-derived portions of the hybrid immunoglobulin-enzyme molecules are chemically joined so that they function as one molecule. The antibody-derived and thrombolytic enzyme-derived portions of the hybrid molecule may be directly linked to each other or may be joined together by an intermediate atom or molecule. The antibody-derived and thrombolytic enzyme-derived portions of the hybrid immunoglobulin-enzyme molecules may be produced separately, then linked together, for example, by chemical conjugation steps which are well known to those of skill in the art, or alternatively, may be produced as one molecule through, for example, the use of genetic engineering, recombinant DNA, and/or hybridoma technologies.

In one embodiment the thrombolytic enzyme molecule is a fibrinolytic enzyme such as PA and the antibody is an IgG molecule, or portions thereof.

As used herein, "thrombolytic" means to dissolve or split up a thrombus.

As used herein, "fibrinolytic" means pertaining to or characterized by fibrinolysis.

As used herein, "fibrinolysis" means the dissolution of fibrin by enzymatic action.

As used herein, "plasminogen activator" (PA) is meant to include any thrombolytic agent or fibrinolytic agent. This term is meant to include, but is not limited to, streptokinase, urokinase, prourokinase (also known as single chain urokinase), tPA, scuPA, anisoylated plasminogen streptokinase activation complex (APSAC), mutant plasminogen activator agents and any other thrombolytic or fibrinolytic agent or enzyme.

As used herein, "uPA" means urokinase-type plasminogen activator.

As used herein, "scuPA" means single chain urokinase-type plasminogen activator and is meant to include both high and low molecular weight forms of scuPA. scuPA exists in two biological forms: high molecular weight scuPA ($\approx 54$ kDa), and low molecular weight scuPA ($\approx 32$ kDa). Both forms of scuPA are single chain molecules and both biological forms are meant to be included by the general term "scuPA." Modifications of "scuPA" have been cloned and are also meant to be included by the term "scuPA". For example, "scuPA (32)" is a form of low molecular weight scuPA that the Inventors cloned. Either of the naturally occurring forms of scuPA can be converted by the enzyme plasmin to the corresponding form of two chain urokinase.

As used herein, "urokinase" (UK) means two chain urokinase which exists biologically as two forms: high molecular weight, two chain UK ($\approx 54$ kDa), and low molecular weight two chain UK ($\approx 32$ kDa).

As used herein, recombinant hybrid molecule "r59D8-tPA(B)", which is also known as "r59D8-tPA", is coded for by the plasmid "pSVtPA(tPA)," which is also known as "pSVD8t($\beta$)." This plasmid does not contain a $CH_2$ region. The 3' untranslated sequence of "pSVtPA(tPA)" came from tPA (FIG. 7).

As used herein, recombinant hybrid molecule "59D8-tPA(AB)" is coded for by plasmid "pSVtPA(Ig)." This plasmid does not contain a $CH_2$ region. The 3' untranslated sequence of "pSVtPA(Ig)" came from the $\gamma$2b IgG molecule (FIG. 7).

As used herein, recombinant hybrid molecule "r59D8-scuPA" is coded for by four plasmids: "pSVUKG(UK)"; "pSVUKG(Ig)"; "pSVUKG($\beta$)"; and "pSVUKc(Ig)." All four of these plasmids code for "r59D8-scuPA ". All four plamids contain a $CH_2$ region and a 144–411 urokinase region. They differ from each other in their 3' untranslated (UT) regions. The 3' UT region of "pSVUKG(UK)", which is also known as "pD8CH2UK," came from the urokinase gene. The 3' UT region of "pSVUKG(Ig)" and "pSVUKc(Ig)" came from the 3' UT region of the mouse $\gamma$2b IgG gene. The 3' UT region of "pSVUKG($\beta$)" came from the 3' UT region of the $\beta$-globin gene (FIG. 7).

Figure 7:
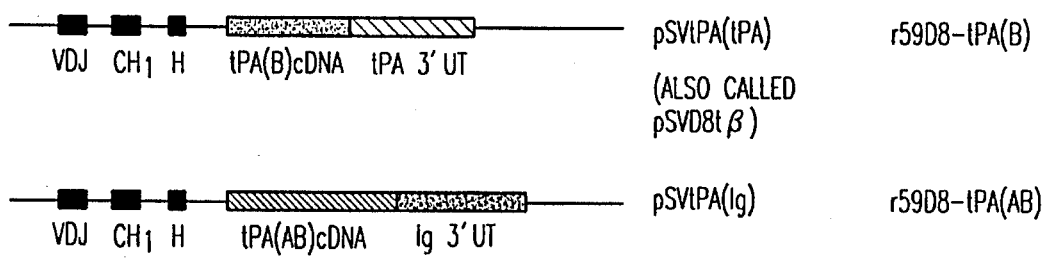
FIG. 7 shows genes transfected into 59D8 L2LV cells, including tPA constructs and urokinase constructs. tPA Constructs: pSVtPA(tPA) contains a genomic variable (VDJ) region from fibrin-specific monoclonal antibody 59D8, cloned genomic constant region (CH1,H) of the mouse γ2b antibody, and the cDNA sequence coding for the B-chain of tPA (amino acids 275 to 527) and the tPA 3' UT region. pSVtPA(tPA) codes for recombinant protein 59D8-tPA(B). In pSVtPA(Ig), the tPA 3' UT domain has been replaced by the 3' UT region from the γ2b Ig gene. In addition, the protein encoding sequence has been expanded to include both the A and B chains of tPA (amino acids 1 to 527). pSVtPA(Ig) codes for recombinant protein 59D8-tPA(AB).
Figure 7:
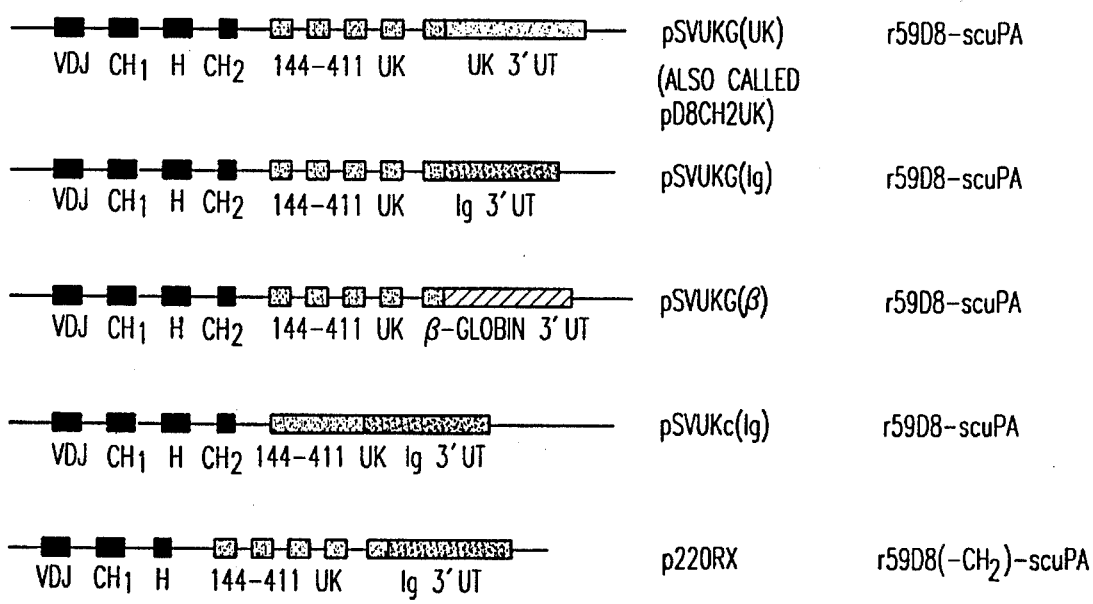

As used herein, recombinant hybrid molecule "r59D8(—$CH_2$)-scuPA", which is also known as "AFA-scuPA", is coded for by the plasmid "p220RX." This plasmid does not contain a $CH_2$ region, hence the "(—$CH_2$)" in the name of the protein produced by it, specifically "r59D8(—$CH_2$)-scuPA." The 3' UT region of "p220RX" came from the $\gamma$2b IgG gene (FIG. 7).

As used herein, "59D8" refers to a murine monoclonal IgG antibody.

As used herein, "64C5" refers to a murine monoclonal IgG antibody.

As used herein, "animal" is meant to include, but is not limited to, humans, including patients, and non-human primates.

As used herein, "imaging" means the visualization or localization of a thrombus which binds the detectably labeled, hybrid immunoglobulin-enzyme molecules of this invention.

As used herein, a "detectable label" is an atom or molecule which is attached to the hybrid immunoglobulin-enzyme molecules of this invention, or a constituent thereof, and which is used in imaging a thrombus. Examples of such labels include, but are not limited to, radioisotopic labels, non-radioactive isotopic labels, chemiluminescent labels, fluorescent labels and enzyme labels, etc.

DETAILED DESCRIPTION OF THE PREFERRED EMBODIMENTS

This invention is directed to hybrid immunoglobulin-thrombolytic enzyme molecules having antigen binding sites which specifically bind a thrombus that is linked to second molecules comprising the enzymatically active portion of thrombolytic enzymes. In one embodiment, this invention is directed to hybrid immunoglobulin-enzyme molecules having an antigen binding site with fibrin specificity and an enzymatic site with fibrinolytic activity. This invention is also directed to the production of these novel hybrid immunoglobulin-enzyme molecules. The hybrid immunoglobulin-enzyme molecules of the present invention may be produced by any known means, including recombinant DNA technology, genetic engineering technology, hybridoma technology, or a combination of all three, as well as by routine chemical conjugation methods. This invention is also directed to methods of using the hybrid immunoglobulin-enzyme molecules of this invention in diagnostic and therapeutic methods.

In preparing the hybrid immunoglobulin-enzyme molecules of this invention, the entire thrombus-specific antibody may be cloned and comprise a portion of the hybrid molecule. However, in order to reduce the size of the hybrid immunoglobulin-enzyme molecule, and to reduce its antigenicity, it is preferable to use only that variable region of the antibody that will recognize and specifically bind a thrombus. Either the variable light or variable heavy chain, or both, may comprise part of the hybrid molecule. In addition, the hinge region of the thrombus-specific antibody may be cloned. The constant domain of the Fab portion of the thrombus-specific antibody joined to the variable region may also be cloned. The variable and constant region of the thrombus-specific antibody cloned and used in the hybrid immunoglobulin-enzyme molecule may be derived from a mammalian source, with humans as the preferred source. Alternatively, the variable region may be from a mammalian source, with the constant region from a human source.

In preparing the hybrid immunoglobulin-enzyme molecules of this invention, the entire thrombolytic enzyme may be cloned and expressed as part of the hybrid molecule. Preferably, only the enzymatically active portion of the thrombolytic enzyme is cloned and expressed as part of the hybrid molecule. This active site or catalytic site may be determined by routine screening as described in the Examples.

The thrombolytic enzyme portion of the construct contains the DNA sequence for a human protein, while the framework of the antibody, or derivative or fragment thereof, will typically be murine in nature. In order to reduce the antigenicity of the construct, modifications can be made to the antibody or antibody fragment. In addition to cloning only the Fv region as described above, most of the murine structural framework of the antibody may be replaced with human framework. This "humanizing" of a mouse antibody, or portions thereof, will reduce the antigenicity of the complex. These modifications can also be done on other animal antibodies.

The process for cloning a hybrid immunoglobulin-enzyme molecule according to the present invention requires the cloning of the thrombus-specific antibody and the thrombolytic enzyme portions and expression of their DNA sequences into a single hybrid molecule.

The DNA sequences of the thrombus-specific antibody and the thrombolytic enzyme employed for preparation of the hybrid immunoglobulin-enzyme molecule may be derived from a variety of sources. These sources include genomic DNA, cDNA, synthetic DNA and combinations thereof. The genomic DNA may or may not include naturally occurring introns.

The DNA obtained from the genomic DNA or cDNA may be obtained in a variety of ways. Cells coding for the desired sequence may be isolated, their genomic DNA fragmented conveniently by one or more restriction endonucleases, and the resulting fragments cloned and screened with a probe for the presence of the DNA sequence coding for thrombus-specificity or for thrombolytic enzymatic activity.

For the variable region of the thrombus-specific antibody, the rearranged heavy chain coding DNA may include V, D and J regions. The rearranged germline light chain coding DNA may include the V and J regions. Once the cloned fragment has been identified which contains the desired thrombus-specific DNA sequence binding site, this fragment may be further manipulated to remove superfluous DNA, modify one or both termini, remove all or a portion of intervening sequences (introns) or the like.

The joining of the various fragments is performed in accordance with conventional techniques, employing blunt-ended or staggered-ended termini for ligation, restriction enzyme digestion to provide for appropriate termini, filling in of cohesive ends as appropriate, alkaline phosphatase treatment to avoid undesirable joining, and ligation with appropriate ligases.

For cDNA, the cDNA may be cloned and the resulting clone screened with an appropriate probe for cDNA coding for the desired variable or constant region. Once the desired clone has been isolated, the cDNA may be manipulated in substantially the same manner as the genomic DNA. However, with cDNA there will be no introns or intervening sequences.

Further, the genes of the thrombus-specific antibody and the genes of the thrombolytic enzyme may be synthesized according to well-known means and cloned for use in preparing the hybrid immunoglobulin-enzyme molecule.

To express the hybrid immunoglobulin-enzyme molecule, transcriptional and translational signals recognized by an appropriate host are necessary. Eukaryotic hosts will be mammalian cells capable of culture in vitro, particularly leukocytes, and more particularly myeloma cells or other transformed or oncogenic lymphocytes, e.g., EBV transformed cells. Alternatively, non-mammalian cells may be employed, such as bacteria, fungi, e.g., yeast, filamentous fungi, or the like.

The DNA sequence coding for the fibrin-specific variable region may be obtained in association with the promoter region from genomic DNA. To the extent that the host cells recognize the transcriptional regulatory and translational initiation signals associated with the variable region, then the region 5' of the variable region coding sequence may be retained and employed for transcriptional and translational initiation regulation.

The contiguous non-coding region 5' to the variable region will normally include those sequences involved with initiation of transcription and translation, such as the TATA box, capping sequence, CAAT sequence, and the like. Usually the 5'-non-coding sequence will be at least 150 bp, more usually at least 200 bp, usually not exceeding about 2 k bp, more usually not exceeding about 1 k bp.

The non-coding region 3' to the thrombus specific constant region may be retained for its transcriptional termination regulatory sequences, such as termination and polyadenylation. In addition, the non-coding region 3' to the coding region also contains an important enhancer in immunoglobulin genes. Thus, by retaining the 3'-region naturally contiguous to the DNA sequence coding for the constant region, the transcriptional termination signals may be provided. Where the transcriptional termination signals are not satisfactorily functional in the expression host cell, then a 3' region functional in the host cell may be substituted.

The constructs for the thrombus-specific antibody and the thrombolytic enzyme may be joined together to form a single DNA segment or may be maintained as separate segments, by themselves or in conjunction with vectors.

The construct(s) may be introduced into a cell by transformation in conjunction with a gene allowing for selection where the construct will become integrated into the host genome. Usually the construct will be part of a vector having a replication system recognized by the host cell.

Expression vehicles for production of the molecules of the invention include plasmids or other vectors. In general, such vectors containing replicon and control sequences which are derived from species compatible with a host cell are used in connection with the host. The vector ordinarily carries a replicon site, as well as specific genes which are capable of providing phenotypic selection in transformed cells. For example, E. coli is readily transformed using pBR322, a plasmid derived from an E. coli species. pBR322 contains genes for ampicillin and tetracycline resistance, and thus provides an easy means for identifying transformed cells. The pBR322 plasmid or other microbial plasmids must also contain, or be modified to contain, promoters which can be used by the microbial organism for expression of its own proteins. Those promoters most commonly used in recombinant DNA construction include the beta lactamase, lactose promoter systems, lambda phage promoters, and the tryptophan promoter systems. While these are the most commonly used, other microbial promoters have been discovered and can be utilized.

For example, a genetic construct for the hybrid immunoglobulin-enzyme molecule can be placed under the control of the leftward promoter of bacteriophage lambda. Control is exerted by the lambda repressor, and adjacent restriction sites are known.

The expression of the hybrid immunoglobulin-enzyme molecule can also be placed under control of other regulatory sequences which may be homologous to the organism in its untransformed state. For example, lactose dependent E. coli chromosomal DNA comprises a lactose or lac operon which mediates lactose utilization by elaborating the enzyme beta-galactosidase. The lac control elements may be obtained from bacteriophage lambda plac5, which is infective for *E. coli*. The lac promoter-operator system can be induced by isopropyl-1-thio-β-D-galactosidase (IPTG).

The expression of the hybrid immunoglobulin molecule can be optimized by replacing the 3' UT region in the plasmid with the 3' UT region of either beta globin or mouse immunoglobulin. For the most part, the 3' UT region which is replaced is that of the thrombolytic enzyme.

Other promoter/operator systems or portions thereof can be employed as well. For example, colicin E1, galactose, alkaline phosphatase, tryptophan xylose, taq, and the like can be used.

The preferred hosts are mammalian cells, grown in vitro in tissue culture, or in vivo in animals. Mammalian cells provide post-translational modifications to immunoglobulin protein molecules including correct folding or glycosylation at correct sites.

Mammalian cells which may be useful as hosts include cells of fibroblast origin such as VERO or CHO-$K_1$ or cells of lymphoid origin, such as the hybridoma SP2/0-AG14 or the myeloma P3x63Sg8, and their derivatives. Preferred mammalian host cells include SP2/0 and J558L. Several cell lines secrete urokinase and may be used for transfection, such as cultured kidney carcinoma cells (Ferraivolo et al., *J. Cell. Physiol.* 121:363 (1984)) and 3T3 cells (Belin et al., *EMBO J.* 3:190 (1984)).

For a mammalian host, several possible vector systems are available for the expression of the hybrid immunoglobulin-enzyme molecule. One class of vectors utilizes DNA elements which provide autonomously replicating extra-chromosomal plasmids, derived from animal viruses such as bovine papilloma virus, polyomavirus, adenovirus, or SV40 virus. A second class of vectors relies upon the integration of the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, or biocide resistance, e.g., to antibiotics, or heavy metals, such as copper, or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayarea, H. (*Mol. Cell Biol.* 3:280 (1983)), and others.

A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are subject to chemical regulation, e.g., by a metabolite or which are temperature-sensitive so that by varying the chemical environment or temperature, their expression can be repressed or initiated.

Another preferred host is yeast. Yeast provides substantial advantages because it can also carry out post-translational peptide modifications including glycosylation. A number of recombinant DNA strategies exist which utilize strong promoter sequences and a high copy number of plasmids which can be utilized for production of the desired proteins in yeast. Yeast recognizes leader sequences on cloned mammalian gene products, and secretes peptides bearing leader sequences (i.e., pre-peptides).

Any of a series of yeast gene expression systems can be used which incorporate promoter and termination elements from the actively expressed genes coding for glycolytic enzymes produced in large quantities when yeast are grown in mediums rich in glucose. Known glycolytic genes can also provide very efficient transcription control signals. For example, the promoter and terminator signals of the phosphoglycerate kinase gene can be utilized.

Once the vector Or DNA sequence containing the construct(s) has been prepared for expression, the DNA construct(s) may be introduced into an appropriate host. Various techniques may be employed, such as protoplast fusion, calcium phosphate-precipitation, electroporation or other conventional techniques. After the fusion, the cells are grown in a selective medium, where untransformed cells are killed, leaving only cells transformed with the DNA construct. Expression of the gene(s) results in assembly to form the hybrid immunoglobulin-enzyme molecule of this invention.

The host cells will, for the most part, be immortalized cells, particularly myeloma or lymphoma cells. These cells may be grown in an appropriate nutrient medium in culture flasks or injected into a synergenic host, e.g., mouse or rat, or immunodeficient host or host site, e.g., nude mouse or hamster pouch. Particularly, the cells may be introduced into the abdominal cavity for production of ascites fluid and harvesting of the hybrid molecules. Alternatively, the cells may be injected subcutaneously and the hybrid molecules harvested from the blood of the host. The cells may be used in the same manner as the hybridoma cells. (See, for example, Diamond et al., *N. Eng. J. Med.* 304:1344 (1981); and Kennatt et al. (eds.), *Monoclonal Antibodies: Hybridomas—A New Dimension in Biologic Analysis*, Plenum Press, New York, New York (1980), which are both incorporated herein by reference).

The hybrid immunoglobulin-enzyme molecule may be isolated and purified in accordance with conventional conditions, such as extraction, precipitation, chromatography, affinity chromatography (the preferred method), electrophoresis, or the like. In the embodiment where the antibody portion is fibrin specific and the enzyme portion is fibrinolytic, the preferred method to selectively isolate the hybrid molecules is affinity chromatography with either the amino terminal heptapeptide of the fibrin beta chain (which binds to the antifibrin site) or with benzamidine (which binds to the PA catalytic site).

The present invention also provides methods for therapy and diagnosis using the hybrid immunoglobulin-enzyme molecules of this invention.

Therapeutic Uses of the Hybrid Immunoglobulin-Enzyme Molecules

The hybrid immunoglubulin-enzyme molecules of this invention may be used in in vivo therapeutic applications in an animal, including primates such as a human being or a baboon. In this embodiment the hybrid molecules are used to lyse a thrombus. The hybrid molecule becomes localized at the site of a thrombus through the thrombus-specific binding site of the hybrid molecule. The thrombus is lysed by the enzymatic activity of the thrombolytic portion of the hybrid molecule. As will be appreciated by one of skill in the art, the specificity of the fibrin specific hybrid enzyme molecule permits selectivity of attachment to and lysis of the thrombus which reduces the risk of serious side effects, such as hemorrhage. In a preferred embodiment the hybrid molecule is fibrin specific and fibrinolytic. In a more preferred embodiment, the hybrid molecule is selected from the group consisting of: 59D8-tPA; 59DS-tPA(β); 64C5-UK; r59D8(—CH$_2$)-scuPA; r59D8-scuPA; r59D8-scuPA; r59D8(—CH$_2$)-scuPA-Fab; and 59D8(—CH$_2$)-scuPA. In a most preferred embodiment, the hybrid molecule is 59D8(—CH$_2$)-scuPA.

In this embodiment, the hybrid molecules of this invention are incorporated into pharmaceutical compositions using standard techniques and methods which are well known to those of skill in the art (see, for example, Regmington's Pharmaceutical Sciences, 18th Edition (Gennaro, A. R., ed.), Mack Publishing Comp., Easton, Pa. (1990).)

The therapeutic compositions which contain the hybrid molecules of this invention can be administered orally, or parenterally, for example, by intravenous (iv), intramuscular, subcutaneous, rectal, transdermal, intrapulmonary, intraperitoneal, intrathecal, intranasalpharyngeal or other known routes of administration. A preferred route of administration is the iv route.

As would be understood by one of ordinary skill in the art, such pharmaceutical compositions may contain salts, buffers, adjuvants, or other substances which are desirable for improving the efficacy of the hybrid molecules of this invention.

Compositions for parenteral administration may include sterile aqueous or non-aqueous solutions, suspensions, and emulsions. Aqueous injection suspensions may contain substances which increase the viscosity of the suspension and include, for example, sodium carboxymethyl cellulose, sorbitol, and/or dextran. Optionally, the suspensions may also contain stabilizers. Examples of non-aqueous solvents are propylene glycol, polyethylene glycol, vegetable oils, such as olive oil, and injectable organic esters such as ethyl oleate.

Carriers or occlusive dressings can be used to increase skin permeability and enhance absorption.

Liquid dosage forms for oral administration may generally comprise a liposome solution containing the liquid dosage form. Suitable forms for suspending liposomes or other encampsulated forms include emulsions, suspensions, solutions, syrups, and elixirs containing inert diluents commonly used in the art, such as purified water.

Besides the inert diluents, such compositions can also include adjuvants, wetting agents, emulsifying and suspending agents, or sweetening, flavoring, or perfuming agents.

Treatment of an animal with a thrombus comprises administering an effective amount of a pharmacological composition containing the hybrid molecules of this invention to the animal in a single dose, multiple doses or infusion.

According to the present invention, an "effective amount" of a therapeutic composition is one which is sufficient to achieve the desired biological effect, herein lysis of a thrombus. Generally, the dosage needed to provide an effective amount of the composition can be adjusted by one of ordinary skill in the art, such as an M.D., and will vary depending upon such factors as the individual hybrid molecule used, the animal's or patient's age, condition, sex, and clinical status including extent of disease, if any, and other variables.

The effective dosage can vary from about 0.01 mg/kg to 500 mg/kg. The dosage should not be so large as to cause adverse side effects, such as, for example, hypersensitivity reactions such as rashes or anaphylactic shock. Diagnostic Uses of the Hybrid Immunoglobulin-Enzyme Molecules The hybrid immunoglobulin-enzyme molecules of this invention may be used in diagnostic applications, including in vivo diagnosis in an animal including a primate, such as a human or a baboon, to label, locate or image a thrombus. In this embodiment, the hybrid molecules are detectably labelled using any of a variety of labels and methods of labeling. The label must produce the type of signal which is detectable by an appropriate type of instrument which is used to detect, locate or image the thrombus. The hybrid molecule becomes localized at the site of the thrombus through the thrombus-specific binding site of the hybrid molecule. If the enzymatic site has been left functionally active after attachment of the label, the labelled hybrid molecule may both label the thrombus and also lyse the thrombus, as previously described. In a preferred embodiment the labelled hybrid molecule is fibrin specific and fibrinolytic.

Examples of types of label which can be used in the present invention include, but are not limited to, enzyme labels, radioisotopic labels, non-radioactive isotopic labels, fluorescent labels, chemiluminescent labels, and nuclear magnetic resonance contrasting agents.

Examples of suitable enzyme labels include, but are not limited to, malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include, but are not limited to, $^{123}$I, $^{99}$Tc, $^{97}$Ru, $^{67}$Ga, $^{68}$Ga, $^{72}$As, $^{89}$Zr, $^{201}$Ti, $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope. Its use may have substantial advantages since it avoids the problem of dehalogenation of $^{125}$I or $^{131}$I-labeled hybrid immunoglobulin molecules by the liver. In addition, this radionucleotide has a more favorable gamma emission energy for imaging (Perkins et al., Eur. J. Nucl. Med. 10:296–301 (1985); Carasquillo et al., J. Nucl. Med. 28:281–287 (1987)). If a radioisotopic label is used for in vivo diagnosis it should have a half-life long enough that it is still detectable at the time of maximum uptake but short enough that unwanted radiation does not remain in the animal after diagnosis.

Paramagnetic isotopes can also be used for purposes of in vivo diagnosis according to the methods of this invention. Examples of elements that are particularly useful as labels for use in Magnetic Resonance Energy techniques include, but are not limited to, $^{157}$Gd, $^{55}$Mn, $^{162}$Dy, $^{52}$Cr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent labels include, but are not limited to, a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to these hybrid immunoglobulin-enzyme molecules can be accomplished using standard techniques which are commonly known to those of ordinary skill in the art such as using an intermediary functional group. Typical techniques are described by Kennedy et al. (*Clin. Chim. Acta* 70:1–31 (1976)), and Schurs et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The detectable label may be attached (o any portion of the hybrid immunoglobulin-enzyme molecule as long as the label does not interfere with the ability of the hybrid molecule to specifically bind to the thrombus or the fibrin in the thrombus. Preferably the label should not interfere with the enzymatic activity of the hybrid molecule either.

A. In Vivo Imaging Using the Labeled Hybrid Immunoglobulin-Enzyme Molecules

The detection of thrombi may be accomplished by the use of in vivo imaging techniques in which the labeled hybrid immunoglobulin-enzyme molecules of the present invention are administered to a patient or other animal, and the presence of a thrombus is detected without the prior removal of any tissue sample. Such in vivo detection procedures have the advantage of being less invasive than other detection methods, and are, moveover, capable of detecting the presence of thrombi in tissues which cannot be easily removed from the patient.

In this embodiment, the hybrid immunoglobulin molecules of this invention can be incorporated into pharmaceutical compositions using standard techniques which are well know to those of skill in the art (see, for example, Remington's Pharmaceutical Sciences, 18th Edition (1990) (Gennaro, A. R., ed.), Mack Publishing Comp., Easton, Pa.), herein incorporated by reference.

The pharmaceutical compositions which contain the hybrid immunoglobulin-enzyme molecules of the present invention, and/or their labeled derivatives just described, can be administered orally or parenterally by the intravenous (iv), intramuscular, subcutaneous, rectal, transdermal, intrapulmonary, intraperitoneal, intrathecal, intranasalpharyngeal or other known routes of administration. A preferred route of their administration is the iv route.

As would be understood by one or ordinary skill in the art, such pharmaceutical compositions may contain salts, buffers, adjuvants, or other substances which are desirable for improving-the efficacy of these hybrid molecules and their conjugates.

Compositions for parenteral administration include sterile aqueous or non-aqueous solutions, suspensions, and emulsions. Aqueous injection suspensions may contain substances which increase the viscosity of the suspension and include, for example, sodium carboxymethyl cellulose, sorbitol, and/or dextran. Optionally, the suspensions may also contain stabilizers. Examples of non-aqueous solvents are propylene glycol, polyethylene glycol, vegetable oils, such as olive oil, and injectable organic esters such as ethyl oleate.

Carriers or occlusive dressings can be used to increase skin permeability and enhance absorption.

Liquid dosage forms for oral administration may generally comprise a liposome solution containing the liquid dosage form. Suitable forms for suspending liposomes or other encampsulated forms include emulsions, suspensions, solutions, syrups, and elixirs containing inert diluents commonly used in the art, such as purified water.

Besides the inert diluents, such compositions can also include adjuvants, wetting agents, emulsifying and suspending agents, or sweetening, flavoring, or perfuming agents.

The detection, localization or imaging of a thrombus in an animal comprises administering an effective amount of a pharmaceutical composition containing the detectably labeled hybrid molecules of this invention to the animal, in a single dose, multiple doses or infusion.

In this embodiment, the dose ranges for administration of the hybrid immunoglobulin-enzyme molecules are those that are effective to delectably label a thrombus. The dosage should not be so large as to cause adverse side effects such as, for example, hypersensitivity reactions such as rashes or anaphylactic shock. Generally, the dosage will vary depending on such factors as the individual hybrid immunoglobulin-enzyme molecule used, the presence and nature of any label, conjugated thereto, the animals' or patients' age, sex, condition, and clinical status, including the extent of disease if any, and other variables. The dose can be routinely adjusted by one of skill in the art such as an M.D. In this embodiment, dosages can range from 0.01 mg/kg to 500 mg/kg of body weight, preferably from 0.01 mg/kg to 200 mg/kg, most preferably from 0.01 to 2 mg/kg.

Having now generally described this invention, the same will be more readily understood by reference to the following methods and specific examples which are included herein for purposes of illustration only. They are not intended to be limiting of the present invention unless specified to be so.

EXAMPLE 1

Production and Fibrinolytic Activity of r59D8-scuPA

The expression plasmid pSVUKG(UK) was designed and cloned. This plasmid coded for the heavy chain of antibody 59D8 and the LMW form of single chain urokinase-like PA (scuPA). The hybrid recombinantly produced immunoglobulin-enzyme molecule obtained (r59D8-scuPA) had an approximate molecular weight of 104 kDa, bound to fibrin, and had the properties unique to single chain urokinase (as tested in the S-2444 and S-2251 assays). r59D8-scuPA effectively bound both fibrin monomer and an anti-urokinase monoclonal antibody simultaneously, thus demonstrating unequivocally the presence of both moieties on the same purified molecule. When r59D8-scuPA was compared to native scuPA in an assay for fibrinolysis, it was approximately 500-fold more potent than native scuPA. This compared to the 100-fold increase in potency obtained by chemically coupling two-chain urokinase to an anti fibrin monoclonal antibody, and surprisingly indicated an even greater than expected effect. This unexpected potency indicated a significantly increased potency in vivo.

Materials

Two-chain, LMW urokinase (Abbokinase™) was purchased from Abbott Laboratories (Abbot Park, Ill.) HMW and LMW scuPA were the kind gifts of Dr. Desire Collen (Center for Thrombosis and Vascular Research, Leuven, Belgium). N-Succinimidyl 3-(2-pyridyldithio)propionate (SPDP) and 2-iminothiolane were obtained from Pierce Chemical (Rockford, Ill.). Sepharose 4B-CL was obtained from Pharmacia P-L Biochemicals (Piscataway, N.J.). The $^{125}$I-labeled fibrinogen came from Amersham (Chicago, Ill.). Plasma was obtained from the local blood bank. Chromogenic substrates H-D-isoleucyl-L-prolyl-L-arginine-p-nitroanilide dihydrochloride (S-2288), L-pyroglutamyl-glycyl-L-arginine-p-nitroanilide (S-2244), and H-D-valyl-L-leucyl-L-lysine-p-nitroanilide dihydrochloride (S-2251) were obtained from Helena Laboratories, Beaumont, Tex. Human placenta factor XIII was purchased from Green Cross (Osaka, Japan). The Superose 12 resin for fast protein liquid chromatography was obtained from Pharmacia (Piscataway, N.J.). Dulbecco's minimum essential medium (DMEM) containing L-glutamine, gentamycin, and fetal calf serum (FCS) was purchased from Gibco Laboratories (Frederick, Md.). The Nutridoma-NS (serum-free medium) was obtained from Boehringer Mannheim (Indianapolis, Ind.). All other chemicals came from Sigma Chemical Company (St. Louis, Mo.).

Methods

Electrophoresis and Autoradiography

SDS-PAGE was performed according to the method of Laemmli (Nature (London) 277:681 (1970)). Proteins were visualized using either Coomassie Brilliant Blue R or, where radiolabeled, by autoradiography for 24–72 hours at −70° C.

Cloning of the 59D8 Heavy Chain Gene

HMW genomic DNA was made from the 59D8 hybridoma cells as previously described in Quertermous et al., *J. Immunol.* 128:2687–2690 (1987), herein incorporated by reference. To identify rearranged heavy chain immunoglobulin genes specific for the 59D8 hybridoma line, Southern blot analysis was performed as previously described With Eco R1-digested genomic DNA and a 1.7-kilobase (kb) Eco R1/Pst1 genomic joining region probe (Southern, E. M., *J. Mol. Biol.* 98:503–517 (1975); Sakano et al., *Nature* 286:676–683 (1980)). Two rearrangements were identified that were not found in the SP2/0 fusion partner or germline Balb/C DNA. Subsequently, one mg of genomic DNA was digested with Eco R1 and was size-fractionated on a preparative agarose gel (Southern, E., in *Methods in Enzymology*, ed. Wu, R. (Academic Press, NY) vol. 68, pp. 152–176 (1979)). Fractions containing each of the two rearranged fragments were identified by hybridization to the joining region probe. These fractions were concentrated and ligated into lambda gt10. The two subgenomic libraries thus constructed were screened with the joining region probe and several potential clones were isolated from each library. (Maniatis et al., *Molecular Cloning*, Cold Spring Harbor Press, Cold Spring Harbor, N.Y. (1982)). Selection of the clone containing the rearranged fragment coding for the 59D8 antigen combining site was accomplished by hybridization to a 20-basepair oligonucleotide that had been constructed on the basis of the sequence of the 59D8 heavy chain mRNA. RNA isolation and sequencing, $^{32}$p labeling of the oligonucleotide with T4 polynucleotide kinase, and hybridization were carried out according to previously described techniques (Maniatis et al., *Molecular Cloning*, supra; Clarke et al., *J. Exp. Med.* 161:687–704 (1985); Suggs et al., *Proc. Natl. Acad. Sci. USA* 78:6613–6617 (1981)).

Fibrin-Specific Antibody/scuPA Genetic Constructs

The cloned restriction fragment, containing variable and joining regions as well as enhancer sequences of the 59D8 gene, was inserted in correct orientation into a plasmid 5' of the mouse gamma 2B heavy chain constant region sequence. This plasmid contained the constant region sequence (PSV GPT/gamma 2B) and also contained the ampicillin resistance gene from pBR322, and the guanine phosphoribosyl transferase (GPT) gene under control of the SV40 viral promoter. It was a gift from Dr. Richard Near (Massachusetts General Hospital, Boston, Mass.). This construct was propagated in *E. coli* MC1061 via the ampicillin resistance gene, and expression of the GPT gene in eukaryotes was selected for in the presence of xanthine, hypoxanthine, and mycophenolic acid. The bulk of the sequence coding for the carboxy terminus of the heavy chain constant region was subsequently removed (using a minimum of amino acids 1–236 of the antibody's genomic heavy chain). It was replaced with a DNA fragment encoding amino acids 144–411 of scuPA, which coded for the LMW form of scuPA. The third exon from either one of the heavy chain constant region genes was joined "in frame" to the scuPA genes such that the usual amino acid sequence would be produced, and a composite protein resulted. This final construct was transfected via electroporation into the appropriate 59D8 hybridoma variant which had stopped producing the usual heavy chain. These transfectants produced an antibody molecule with fibrin specificity, with the PA moiety at the tail end of the truncated heavy chain.

Monoclonal Antibodies and Selection of Loss Variants

Fibrin-specific monoclonal antibody 59D8 was raised by immunization with a synthetic heptapeptide based on the amino terminal sequence of the fibrin beta chain, as previously described in Hui et al., *Science* 222:1129–1132 (1983). Hybridoma cells and loss variants were maintained in complete medium: DMEM with 4.5 mg/ml glucose, 12 percent FCS, 50 g/ml gentamicin sulfate, and 0.6 mg/ml L-glutamine. For selection of heavy chain loss variants, cells were grown in soft agarose. Five ml of complete medium plus 0.2% agarose and an additional 89 FCS was added to tissue culture dishes (60 mm) and was allowed to solidify at room temperature for 3 to 5 minutes. Cells (1 to 2×10$^3$) to be selected for chain loss were layered over the agarose. The plates were incubated at 37° C. in 6% CO$_2$ until clusters of cells were formed (2 to 4 days). To detect heavy chain loss variants, cell clusters were overlayed with an antiserum solution (1.0 ml) containing complete medium with 0.2% agarose and 5 to 10% rabbit or goat anti-mouse heavy chain. Cell clusters which secreted heavy chains developed a precipitin halo. Clusters that did not have a precipitin halo were picked from soft agarose by capillary pipet and subsequently were delivered into 96-well plates which contained complete medium with 89 additional FCS. Individual subclones were assayed by enzyme-linked immunoabsorbent assay (ELISA) or by Western blotting for the presence of heavy and light chain.

Construction and Expression of Recombinant Protein

A recombinant immunoglobulin comprising the fibrin specific monoclonal antibody 59D8 and LMW scuPA as the PA was constructed and expressed. A genomic lambda phage clone of uPA was kindly provided by Dr. F. Blasi (Riccio et al., *Nucleic Acids Res.* 13:2759 (1985)). Eco RI fragments isolated from this clone were ligated into pGem to reconstruct the sequences coding for LMW scuPA. Synthetic oligonucleotides were used to reconstitute the 5' portion of the sequence and provide appropriate restriction sites. A XhoI/Sal fragment carrying this sequence was excised from pGEM and was exchanged for the tPA(B) cDNA sequence in the expression plasmid pSUD8tβ. Thus a peptide identical to LMW scuPA (uPA amino acids leu 144→leu 411) was joined in-frame at the hinge region of the immunoglobulin protein. This expression vector pD8UK was further modified by insertion of the exon coding for the CH$_2$ domain of the immunoglobulin constant region, into the unique XhoI site of the hinge region. The correct reading frame and appropriate cloning ends of the fragment were again provided by synthetic oligonucleotides. The expression plasmid pSVUKG(UK) was then transfected into 59D8 heavy chain loss variant hybridoma cells. Cells were grown in DMEM containing 20% FCS initially. After growth to confluence, the culture supernatant was replaced with DMEM containing 20% Nutridoma-NS™ (serum-free culture medium) and 2 KIU aprotonin/ml, and the cells were monitored for viability. Supernatants were harvested between days 3 and 5. The r59D8-scuPA protein was purified on Sepharose-conjugated β peptide. For purification of larger amounts of r59D8-scuPA, retired Balb/C breeder mice were primed with pristane and 7 days later were injected with 1×10⁶ pSVUKG(UK)-containing hybridoma cells per mouse. After harvesting the ascites, the r59D8-scuPA was purified on a Sepharose-conjugated β peptide column.

Transfection and Selection

The construct pSVUKG(UK) was transfected into loss variant cells by electroporation, using an Isco power supply as described in Potter et al., *Proc. Natl. Acad. Sci. USA* 81:7161–7165 (1984). Optimal transfection conditions were a 2000-volt discharge into 0.8 ml of phosphate buffered saline. Transformants were selected by growth in mycophenolic acid, xanthine and hypoxanthine. Confirmation of transfection and expression was obtained by Northern blot analysis using a 2 kb cDNA probe coding for the 3' portion of the human urokinase chain (Maniatis et al., *Molecular Cloning*, supra). Transfected cell lines were subcloned according to standard techniques.

Characterization of the Hybrid Immunoglobulin-Enzyme Molecules

The hybrid molecules were subjected to SDS-PAGE under both reducing and nonreducing conditions. The gels were either stained with Coomassie Blue or were subjected to Western blotting by labeling the PA with $^{125}$I before coupling.

Chromogenic Substrate Assay for Peptidase Activity

To assess the functional properties of the hybrid molecule, its peptidolytic properties were first examined with respect to a nonselective substrate, H-D-isoleucyl-L-prolyl-L-arginine-p-nitroanalide dihydrochloride (S-2288). The S-2288 assay was performed with a total volume of 1.0 ml in 0.05M Tris-HCl, 0.10M NaCl (pH 8.5) with a substrate concentration of 3×10⁴M. Absorbance at 405 nm was measured every 10 seconds at 20° C.

Activity of scuPA and r59D8-scuPA scuPA contained little activity in the S-2444 assay before activation by plasmin. The pre- and post-activation (by plasmin) activity in the S-2444 assay was determined as described by Stump et all. (*J. Biol. Chem.* 26:17120–17126 (1986)).

Fibrin Monomer-Sepharose Assay

The plasminogen activating potency of tPA, urokinase (Abbokinase™, Abbot lot #82-087-AF Abbot Laboratories (Abbott Park, Ill.), a urokinase-59D8 chemical conjugate, and r59D8-scuPA were compared at equivalent peptidase activities, as measured by the S-2288 chromogenic substrate assay. Relative fibrinolytic potency was quantified by measuring the lysis of $^{125}$I-labeled fibrin monomer covalently linked to cyanogen bromide-activated Sepharose 4B-Cl (Bode et al., *Science* 229:765–767 (1985)). To facilitate direct statistical comparison between fibrinolysis with a PA alone and fibrinolysis with a PA coupled chemically to antibody 59D8 and as part of the recombinant proteins, a Fit-Function Program was applied to the data from each assay and the curves were compared by the t test.

Fibrinogen Assays

The fibrinogen content of samples of citrated human or rabbit plasma was determined by two methods. Clottable fibrinogen was measured by the method of Clauss, *Acta Chir. Scand.* 90:419 (1957), and total fibrinogen was determined by sodium sulfite precipitation.

Plasma Clot Assay

The method of Lijnen et al. (*Thromb. Haemostas.* 52:308 (1984)) was used with the following modifications. Human fresh-frozen plasma obtained from at least four donors was pooled, aliquoted, and refrozen. Immediately before each experiment, the activities of scuPA and the hybrid immunoglobulin molecules were calibrated using the S-2288 assay (i.e., the peptidase activities of the PAs and the hybrid molecules were determined and appropriate dilutions were made so that the peptidase activity (in units/ml) was identical for each sample). Plasma clots were made by adding each of the following to fresh-frozen plasma: thrombin, 8 NIH units/ml; 0.5M $CaCl_2$, 100 µl/ml; and $^{125}$I-labeled human fibrinogen (IBRIN)™, 40,000 cpm/ml (Amersham, Chicago, Ill.). The solution was immediately drawn into Silastic tubing (internal diameter (I.D.)=4 mm), and was incubated at 37° C. for 30 minutes. Silastic tubing containing clotted fresh-frozen plasma was cut into. 1.5 cm sections, yielding clots of 0.2 ml. These clots were then washed in 0.15M NaCl before use. Each clot was placed in a plastic tube, was counted, and was suspended in 1 ml fresh-frozen plasma (from the same pool). Experiments were initiated by the addition of a PA (or hybrid molecule of PA and antibody). At 30 minute intervals, an aliquot of the fresh-frozen plasma was removed from each tube for counting. Samples were saved at the end of the experiment for determination of fibrinogen levels.

In vivo Thrombolysis

The rabbit jugular vein model of Collen et al. (*J. Clin. Invest.* 71:368 (1983)) was used. After sedation of the rabbit with acetopromazine and ketamine, a paramedial incision was made from the right mandible to above the right clavicle. The external jugular vein was isolated by dissection, and its branches were ligated and separated. A segment of woolen thread was introduced to anchor the clot. After bleeding ceased, vascular clamps were placed so as to isolate this segment of the external jugular vein. The components of the clot were introduced into the isolated vein segment. These components consisted of approximately 500,000 cpm of $^{125}$I-labeled human fibrinogen (each sample was counted before use), 100 µl of packed human red blood cells, 100 µl of human fresh-frozen plasma, 10 µl of 0.5M $CaCl_2$ and 10 µl of bovine thrombin (8 NIH units). After 30 minutes, the vascular clamps were removed and blood flow was restored. A sample of blood was taken immediately after the clamps were released to determine radioactivity that was not incorporated into the thrombus. Measured amounts of PA were diluted to a volume of 25 ml, and were delivered via the marginal vein of the contralateral ear over 4 hours by an infusion pump. Lost counts were determined by counting syringes, gauze sponges and tubing. Six hours after initiation of the infusion, the entire vein segment was isolated, removed and counted. Percent lysis was determined as the ratio of the counts remaining at the termination of an experiment over the net counts at the beginning.

Results

Figure 1:
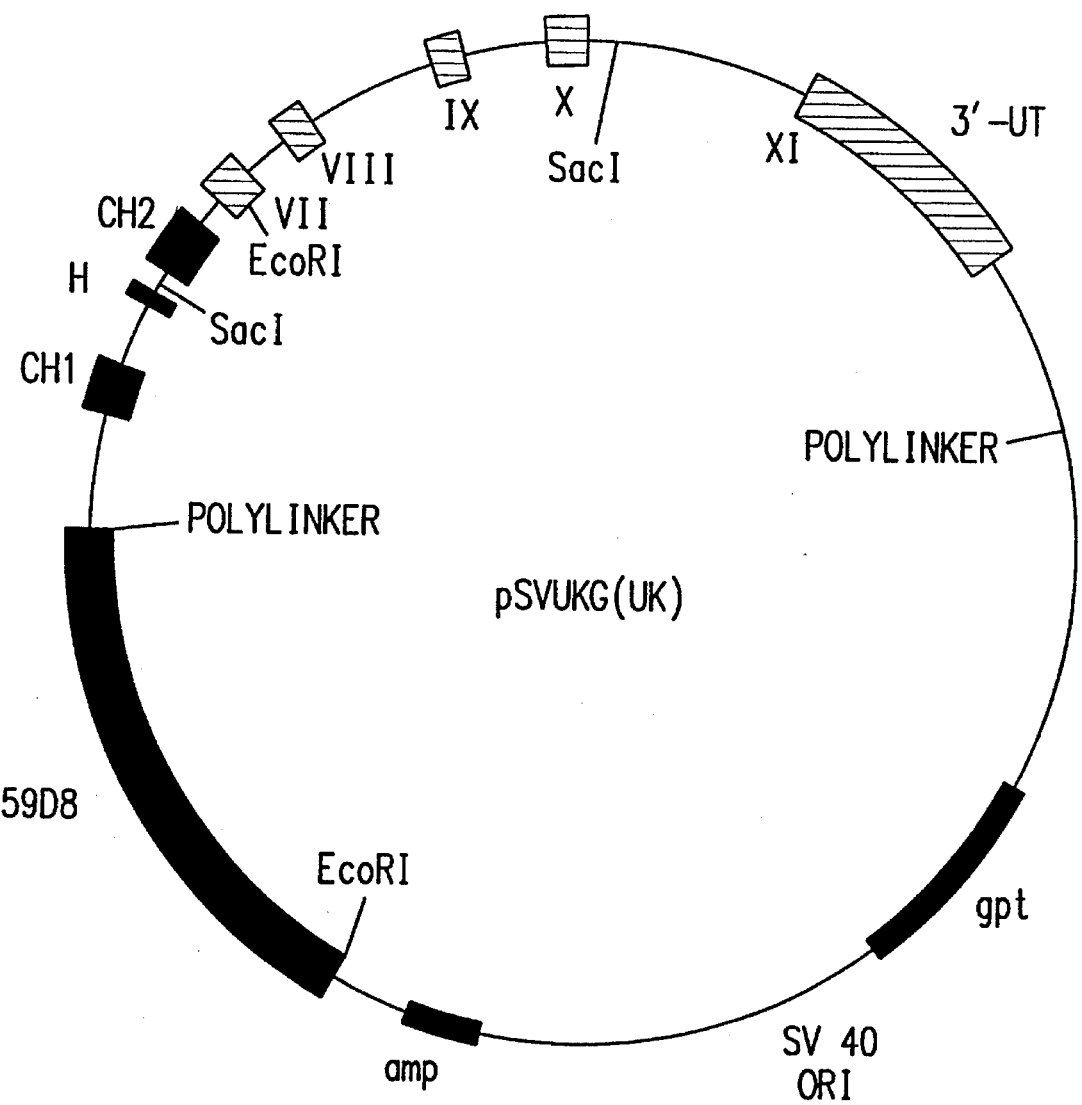
FIG. 1 shows the expression plasmid pSVUKG(UK), which is also known as pD8CH2UK. The structure of this plasmid which contains the DNA coding for the heavy chain of antibody 59D8 and LMW scuPA is shown. Coding sequences are labeled outside the circle, restriction sites are inside the circle, the CH1, hinge (H) and CH2 regions of 59D8 and the domains of urokinase (roman numerals) are shown.

FIG. 1 shows the expression plasmid pSVUKG(UK). The plasmid was transfected into heavy chain loss variant 59D8 hybridoma cells as described. r59D8-scuPA was purified from supernatants and ascites by chromatography on β peptide-Sepharose and the samples were analyzed by SDS-polyacrylamide gel electrophoresis under reducing and non-reducing conditions. A Coomassie-stained SDS polyacrylamide gel under non-reducing conditions with molecular weight standards, antibody 59D8, and r59D8-scuPA purified from ascites demonstrated two visible bands for purified r59D8-scuPA. One, of approximately 104 kDa, was consistent with the predicted size of this molecule. A second, HMW band was also present. When western blotting was performed with a $^{125}$I-labeled goat anti-mouse Fab probe, both bands were visualized. r59D8-scuPA purified from ascites exhibited a band to which $^{125}$I-labeled goat anti-mouse Fab bound, of approximately 104 kDa. Antibody 59D8 was also visualized. Under reducing conditions the approximate molecular weight of r59D8-scuPA was 80 kDa (data not shown).

To assay for urokinase activity, two-chain urokinase, r59D8-scuPA and HMW scuPA were compared in the S-2444 assay. Two-chain urokinase was active in the S-2444 assay, whereas purified scuPA showed little activity. Each r59D8-scuPA preparation contained some urokinase activity. In addition, after incubation with plasmin (which effected the conversion of single-chain urokinase to two-chain urokinase), the activity of r59D8-scuPA increased approximately 6–8 fold. In comparison, two-chain urokinase was not activated by preincubation with plasmin, and the activity of HMW single-chain scuPA was activated 10–12 fold by preincubation with plasmin. This suggested that LMW scuPA activity was partially preserved in the construct.

Figure 2:
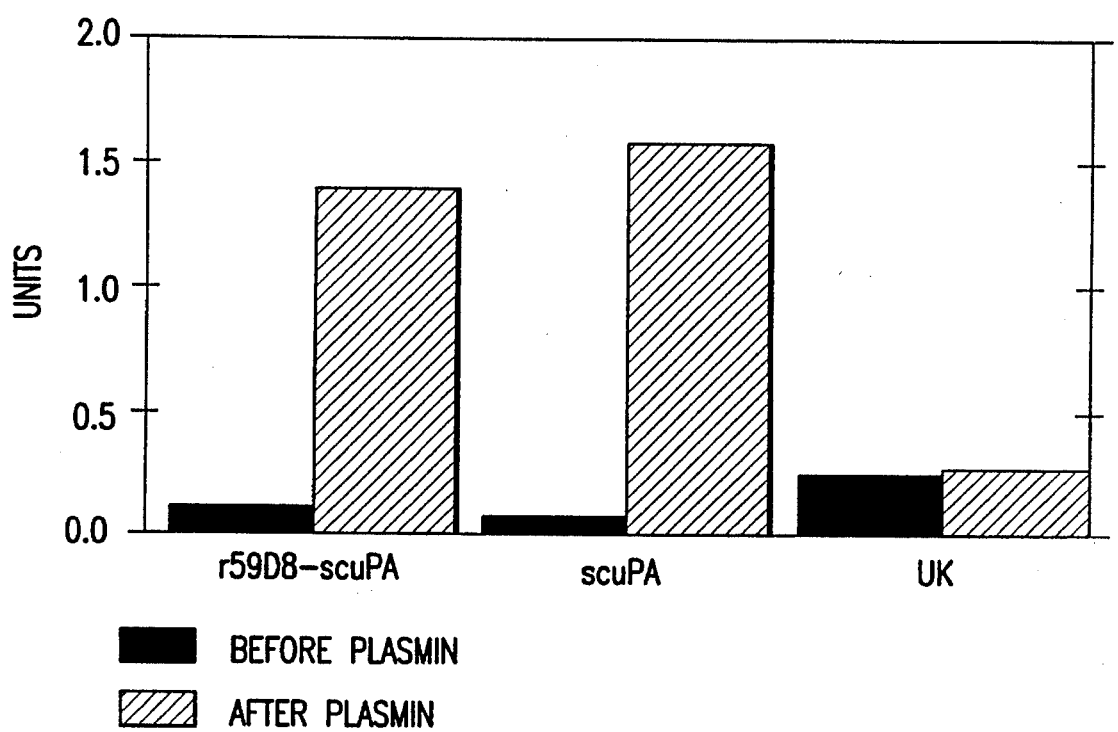
FIG. 2 shows enhanced fibrinolytic potency, activation by plasmin. The fibrinolytic potencies of recombinant 59D8-scuPA (r59D8-scuPA, also known as r59D8-scuPA(32)), scuPA, and UK were compared in the fibrin monomer sepharose assay. Each data point represents the mean of duplicate determinations.

The final test of any modified PA is whether it shows enhanced fibrinolysis. In comparison tests, the activity of r59D8-scuPA, native scuPA, a chemical conjugate between two chain UK and antibody 59D8, and UK were compared in the fibrin monomer sepharose assay. The chemical conjugate between UK and antibody 59D8 had been demonstrated to be 100-fold more potent than UK alone, 10-fold more potent than tPA and equipotent to a chemical conjugate between tPA and antibody 59D8 in this assay. The r59D8-scuPA construct was approximately 500 fold more potent than native scuPA (FIG. 2). Other tests (data not shown) demonstrated that r59D8-scuPA was at least 50 fold more potent than even the 59D8-UK chemical conjugate.

It had been previously demonstrated that molecules which showed enhanced potency in this fibrinolysis assay also showed enhanced potency in the human plasma clot model and in the rabbit jugular vein model. In comparison tests using the human plasma clot and the rabbit jugular vein models, the activity of r59D8-scuPA, native scuPA, a chemical conjugate between two chain UK and antibody 59D8, and UK were compared in the fibrin monomer sepharose assay. These comparison assays showed that r59D8-scuPA had enhanced potency for fibrinolysis over the native scuPA, the UK-59D8 conjugate and native UK.

Figure 3:
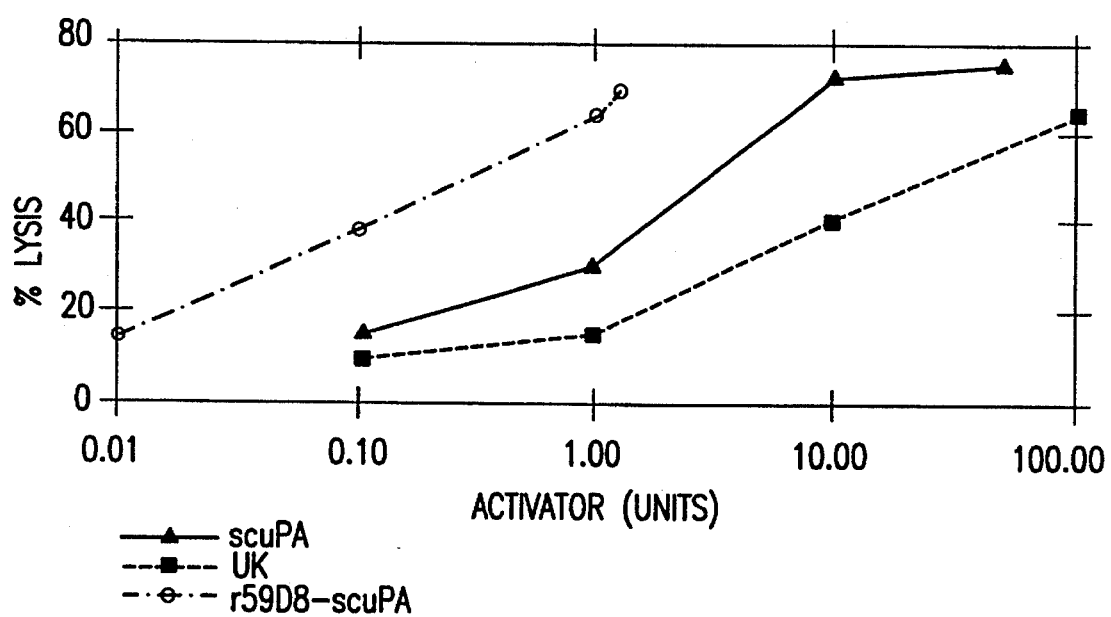
FIG. 3 shows the activation of two-chain urokinase (UK), r59D8-scuPA, and HMW scuPA by plasmin. Equivalent activities of two-chain urokinase, r59D8-scuPA and HMW scuPA were compared in the S-2444 assay before and after a pre-incubation period with plasmin. The reaction was terminated by the addition of 100 μl of 50% glacial acetic acid. The absorbance at 405 nm is shown. Each bar represents the mean of triplicate samples.

The properties of r59D8-scuPA proved to be quite unexpected and remarkable. It bound to fibrin with an affinity equal to that of antibody 59D8 (kDa of $5 \times 10^{-10}$, data not shown) and, although there was more two chain urokinase activity present in the preparations than in preparations of purified scuPA, the evidence demonstrated that a portion of the purified r59D8-scuPA existed in the single-chain form (FIG. 3). Thus by taking advantage of the unique properties of scuPA, a molecule was designed, cloned and expressed in which the PA portion was brought into proximity with fibrin by virtue of its antibody 59D8 domain, and in which plasmin was cleaved while the PA was still attached to the antibody. The result was a fully active recombinant protein with all the intended properties which was more potent than the corresponding chemical conjugate of UK and 59D8.

EXAMPLE 2

Production and Fibrinolytic Activity of r59D8-tPA(B)

Materials and Methods
Cloning of the 59D8 Heavy Chain Gene

HMW genomic DNA was made from the 59D8 hybridoma cells as previously described in Quertermous et al., *J. Immunol.* 128:2687–2690 (1987). To identify rearranged heavy chain immunoglobulin genes specific for the 59D8 hybridoma line, Southern blot analysis was performed as previously described with Eco R1-digested genomic DNA and a 1.7-kilobase (kb) Eco R1/Pst1 genomic joining region probe (Southern, E. M., *J. Mol. Biol.* 98:503–517; Sakano et al., *Nature* 286:676–683 (1980)). Two rearrangements were identified that were not found in either of the cells originally fused to produce the 59D8 hybridoma (SP2/0 and Balb/c). Subsequently, one mg of genomic DNA was digested with Eco R1 and was size-fractionated on a preparative agarose gel (Southern, E., in *Methods in Enzymology* (Wu, R., ed.) (Academic Press, NY), Vol. 68, pp. 152–176 (1979)). Fractions containing each of the two rearranged fragments were identified by hybridization to the joining region probe. These fractions were concentrated and ligated into λgt10. The two subgenomic libraries thus constructed were screened with the joining region probe and several potential clones were isolated from each library (Maniatis et al., *Molecular Cloning*, 1982 (Cold Spring Harbor Press, Cold Spring Harbor, N.Y.)). Selection of the clone containing the rearranged fragment coding for the 59D8 antigen combining site was accomplished by hybridization to a 20 basepair oligonucleotide that had been constructed on the basis of the sequence of the 59D8 heavy chain mRNA. RNA isolation and sequencing, $^{32}$p labeling of the oligonucleotide with T4 polynucleotide kinase, and hybridization were carried out according to previously described techniques (Maniatis et al., *Molecular Cloning*, supra; Clarke et al., *J. Exp. Med.* 161:687–704 (1985); Suggs et al., *Proc. Natl. Acad. Sci. USA* 78:6613–6617 (1981)).

Expression Vector Construction

The tPA sequence was derived from a cDNA clone (pPA34'F) that had been constructed from HeLa cell mRNA (Fisher et al., *J. Biol. Chem.* 260:11223–11230 (1985)). DNA encoding the β chain (SacI site to the Eco R1 site of pBR322) was isolated and ligated into pGEM3. Next, a contiguous 5' fragment was isolated by digestion with SfaN1 and Sac1. A synthetic oligonucleotide, containing a Bam H1 end, an XhoI site, and two bases reconstituting a codon for glycine, was added to this second fragment's 5' end. The modified fragment was then ligated into a plasmid already containing the 3' fragment, thus reconstituting the chain sequence. The chain was excised with XhoI and Sca1—the Sca1 site having been contributed by the pBR322 sequence.

The final construct was assembled in the pSV2gpt vector that had been modified by the insertion of a polylinker containing a 6 kb Xba1 restriction fragment encoding the murine λ2b heavy chain constant region (Mulligan et al., *Proc. Natl. Acad. Sci. USA* 78:2072–2076 (1981); Tucker et al., *Science* 206:1303–1306 (1979)). The productive 59D8 heavy chain rearranged gene that had been cloned on a 2.6 kb Eco R1 fragment was inserted in the correct orientation into an Eco R1 site in the polylinker 5' of the λ2b constant region. The constant region sequence between the unique XhoI site in CH2 and a Sal1 site in the polylinker was excised, the Sal1 site was blunted and the tPA chain was ligated into place. Nucleotide sequence analysis confirmed that the junction between the 59D8 heavy chain and tPA segments was in-frame (Sanger et al., *Proc. Natl. Acad. Sci. USA* 74:5463–5467 (1977)).

Monoclonal Antibodies and Selection of Loss Valiants

Fibrin specific monoclonal antibody 59D8 was raised by immunization with a synthetic heptapeptide based on the amino terminal sequence of the fibrin chain, as previously described in Hui et al., *Science* 222:1129–1132 (1983). Hybridoma cells and loss variants were maintained in complete medium: DMEM with 4.5 mg/ml glucose, 12 percent FCS, 50 g/ml gentamicin sulfate, and 0.6 mg/ml L-glutamine. For selection of heavy chain loss variants, cells were grown in soft agarose. Five ml of complete medium plus 0.2% agarose and an additional 8% FCS was added to tissue culture dishes (60 mm) and was allowed to solidify at room temperature for 3 to 5 min. Cells (1 to $2\times10^3$) to be selected for chain loss were layered over the agarose. The plates were incubated at 37° C. in 6% $CO_2$ until clusters of cells were formed (2 to 4 days). To detect heavy chain loss variants, cell clusters were overlayed with 1.0 ml antiserum solution containing complete medium with 0.2% agarose and 5 to 10% rabbit or goat anti-mouse heavy chain. Cell clusters secreting heavy chain developed a precipitin halo. Clusters that did not have a precipitin halo were picked from soft agarose by capillary pipet and subsequently were delivered into 96-well plates containing complete medium with 8% additional FCS. Individual subclones were assayed by enzyme-linked immunoabsorbent assay (ELISA) or by Western blotting for the presence of heavy and light chains.

Transfection and Selection

The construct pD85Vtβ was transfected into loss variant cells by electroporation using an Isco power supply as described in Potter et al., *Proc. Natl. Acad. Sci. USA* 81:7161–7165 (1984). Optimal transfection conditions were a 2000-volt discharge into 0.8 ml of phosphate buffered saline. Transformants were selected by growth in mycophenolic acid, xanthine and hypoxanthine. Confirmation of transfection and expression was obtained by Northern blot analysis using a 2 kb cDNA probe coding for the 3' portion of the human tPAβ chain (Maniatis et al., *Molecular Cloning*, supra). Transfected cell lines were subcloned according to standard techniques.

Protein Purification

Protein was purified from cell supernatants and from ascites by sequential double affinity chromatography on two columns. One column was constructed by linking the synthetic peptide used for the generation of 59D8 to Sepharose. The other consisted of an anti-human tPA monoclonal antibody linked to Sepharose. A third column, composed of benzamidine linked to Sepharose had been used in the initial purification attempts. However, even though benzamidine bound well to the active site of tPA and benzamidine-Sepharose can be used to purify the intact molecule, the column did not retain the recombinant protein.

Purification of the recombinant protein was monitored by two solid-phase immunoassays. To detect antifibrin antibody activity, 96-well microtiter plates were coated with fibrin monomer and were blocked with 10% horse serum. They were then incubated with samples, and were washed and were probed with $^{125}$I-labeled goat anti-mouse Fab. The second assay was designed to detect tPA antigen associated with antifibrin antibody activity. In this assay, the fibrin-monomer-coated plates were incubated with culture supernatant or ascites and were probed with $^{125}$I-labeled anti-human tPA. Because the chain of tPA possessed no fibrin binding activity, only recombinant protein containing both functional domains was detected.

Western Blot Analysis

Western blots were made from both reduced and nonreduced samples separated on SDS-polyacrylamide gels using established techniques (Burnette, W. N., *Anal. Biochem.* 112:195–203 (1981)). Either goat anti-mouse Fab or a monoclonal anti-human tPA antibody labeled with $^{125}$I was used as a probe.

Antigen Binding Assay

The original antibody (59D8) and the recombinant molecule were first assayed for the presence of fibrin-binding Fab antigen. This was accomplished with the solid-phase immunoassay described above using $^{125}$I-labeled goat anti-mouse Fab as a probe. Titration curves were generated for 59D8 and the recombinant protein by varying their concentrations in the assay. That concentration which would yield the same amount of bound $^{125}$I-labeled antibody was then selected from the linear part of each curve. At this concentration of either 59D8 or 59D8-tPA fusion protein, a competition assay was performed in wells that had been coated with fibrin and filled with various amounts of soluble fibrin. Protein that bound to the soluble rather than insoluble fibrin was removed by washing before application of the labeled antibody.

Assays of Enzymatic Function

To compare the enzymatic function of the recombinant protein with that of native tPA, its peptidolytic properties were first examined in an assay which measured cleavage of the nonselective chromogenic substrate S-2288 (Helena Labs, Beaumont, Tex.). The assay was carried out in a 50 µl volume of buffer (0.15M Tris, 0.15M NaCl) with a 1 millimolar final concentration of chromogenic substrate. Various concentrations of recombinant protein or tPA purified from the Bowes melanoma cell line (Bio Response, Hayward, Calif.) were added and the absorbance at 405 nm was measured at a series of time points.

To determine whether the recombinant protein was capable of activating plasminogen, a second assay was performed utilizing the chromogenic substrate S-2251 (Helena Labs, Beaumont, Tex.). The activity of melanoma tPA, the recombinant protein and bovine trypsin were first determined in the S-2288 assay and the concentrations were adjusted such that each enzyme was present at 100 units/100 µl. One hundred µl of melanoma tPA, recombinant protein or bovine trypsin was then added in serial dilution to 100 µl of human plasminogen (0.15 mg/ml) and 800 µl of S-2251 substrate. The samples were incubated for 60 min at 37° C. The reaction was terminated by the addition of 1 ml of 50% acetic acid and absorbance at 405 nm was determined.

Results

Figure 4:
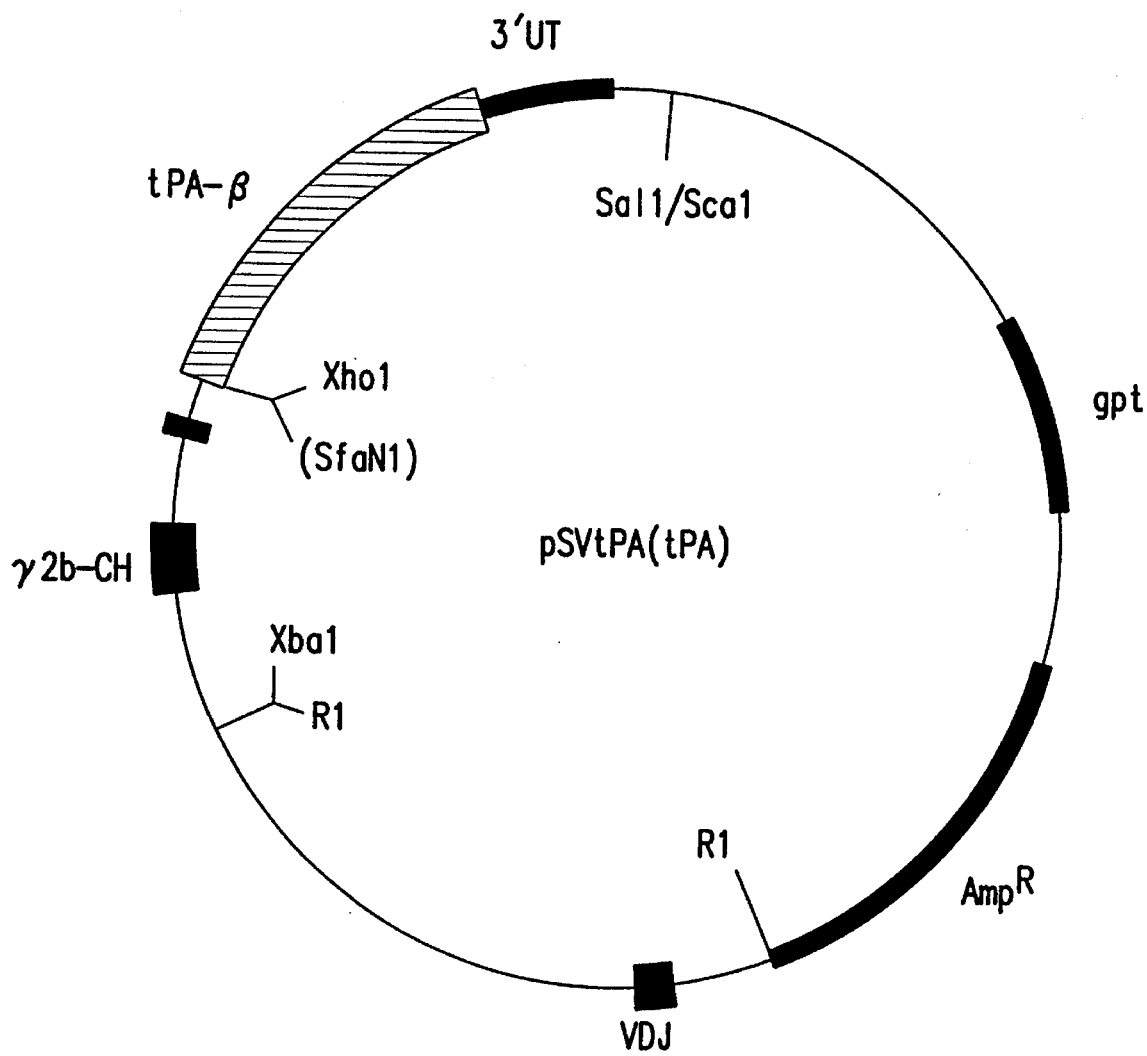
FIG. 4 shows the structure of expression plasmid pSVtPA(tPA), also known as pSVD8tβ, which codes for the heavy chain-tPA fusion protein. Coding sequences are indicated by labels outside the circle; restriction sites used in construction are indicated inside the circle. Abbreviations: VDJ, productive 59D8 heavy chain rearrangement; 2b-CH, genomic sequence of the murine 2b heavy chain constant region; tPA-cDNA, sequence coding for the human tPA chain; 3'-UT, 3' untranslated sequence (UT) of human tPA-cDNA; Amp$^r$, pBR322 ampicillin resistance gene; gpt, $E.$ $coli$ guanine phosphoribosyl transferase gene driven by SV40 promoter; RI, Eco RI.

Electroporation of the construct pSVtPA(tPA) (FIG. 4) into the 59D8 heavy chain loss variants provided numerous transfected clones. When approximately $1\times10^8$ hybridoma cells were mixed with 50 µg of circular plasmid DNA in 0.8 ml of phosphate buffered saline and subjected to a discharge of 2000 volts, approximately 15 of the wells on a 96-well plate contained drug-resistant clones. Approximately 75% of these clones were shown to secrete the recombinant protein. Five clones were chosen for further analysis on the basis of their growth rate and expression of mRNA coding for the fusion protein.

Western blot analysis of the affinity-purified recombinant protein was done. Blots of reduced gels probed with an iodinated anti-human tPA monoclonal antibody revealed labeling of a 65 kDa peptide. This was the expected size of a heavy chain tPA fusion protein. The β chain of tPA is approximately 33 kDa and the truncated heavy chain should contribute 30 kDa. Several lines of evidence indicated that the 65 kDa peptide was not a tPA-like molecule contributed by FCS. The 65-kDa band was observed when the transfected cell lines were grown in serum-free medium or in the intraperitoneal space of mice. Also, when bovine tPA from was purified from FCS by benzamidine affinity chromatography, even though it was labeled by the antibody on Western blots, the size of the molecule was 75 kDa.

Western blots of reduced samples probed with a goat anti-mouse Fab derived from polyclonal sera revealed labeling of a 25 kDa protein, which was the expected size of the 59D8 κ light chain. Although on such blots this reagent usually labels the mouse immunoglobulin heavy chains also, the absence of labeling of the fusion peptide was not surprising since most of the heavy chain constant region had been removed. Blots produced with unreduced samples showed labeling of a single band at a molecular weight of 170–180 kDa by both of the iodinated antibodies. This provided strong evidence that the hybridoma cells produced a molecule that contained both immunoglobulin and tPA peptides. The 170–180 kDa value suggested that the inter-heavy-chain disulfide bonds had formed to give a Fab'$_2$-like molecule that contained two antigen combining sites and two tPA moieties.

Figure 5A:
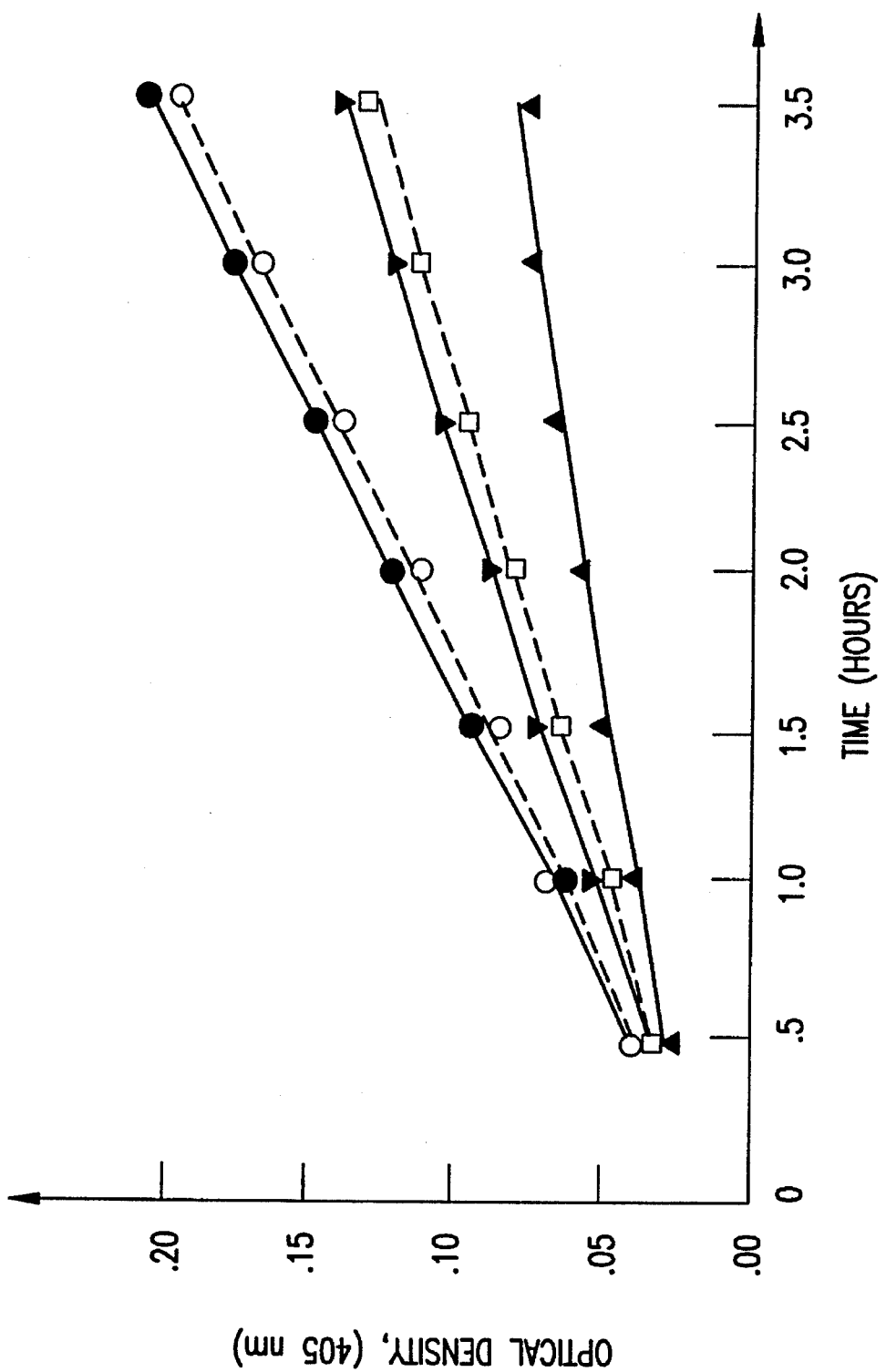
FIG. 5A: As shown by the dashed lines, the S-2288 assay was performed with 105 ng (open circles) or 70 ng (open boxes) of recombinant protein. Solid lines represent the catalytic activity of 50 ng (solid circles), 40 ng (solid boxes) or 30 ng (solid triangles) of melanoma tPA used as standards. Relative molar activity of the recombinant protein was determined by comparison with tPA standards with similar rates of catalysis.

The peptidolytic activity of the tPA portion of the molecule was initially assessed by measuring the cleavage of the nonspecific substrate S-2288. Cleavage of this tripeptide can be accurately monitored by following the production of paranitroaniline, which absorbs light at a wavelength of 405 nm. FIG. 5A shows a typical assay, which directly employed the activity of differing concentrations of pure melanoma tPA. Activity in this assay was defined as the rate of change in optical density. When a comparison was made on a molar basis between the recombinant protein and the native tPA, the recombinant protein possessed 70% of the activity of native tPA.

Figure 5B:
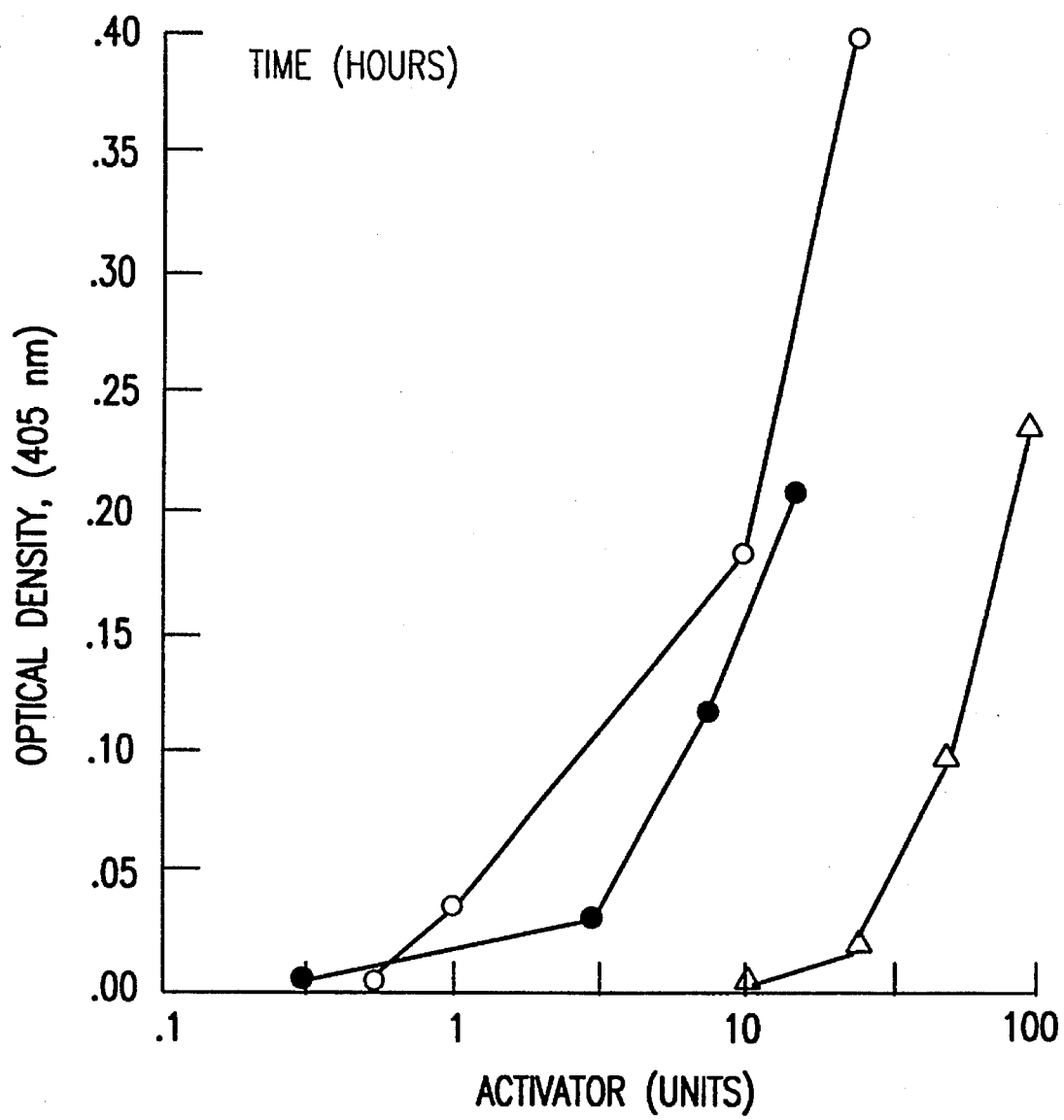
FIG. 5B: The S-2251 assay was conducted with varying activities of melanoma tPA standard (open circles), recombinant protein (solid circles) and bovine trypsin (open triangles). Units of activity of each protein were determined in the S-2288 assay.

A S-2251 assay was performed to determine whether the catalytic β subunit maintained activity against plasminogen (its physiologic substrate). Here the PA was required to convert plasminogen to plasmin and the plasmin subsequently liberated paranitroaniline from a synthetic tripeptide. Neither PA nor trypsin can directly convert the S-2251 substrate. The amidolytic activities of the recombinant protein, melanoma tPA and trypsin were first determined in the S-2288 assay. Then the ability of comparable amounts of each to convert plasminogen was determined. FIG. 5B reveals that the ability of the recombinant protein to act upon the physiologic substrate was very similar to that of native tPA. Although a nonspecific serine protease such as trypsin is able to convert plasminogen to plasmin, it does so much less efficiently than does either the native or recombinant PA.

Figure 6:
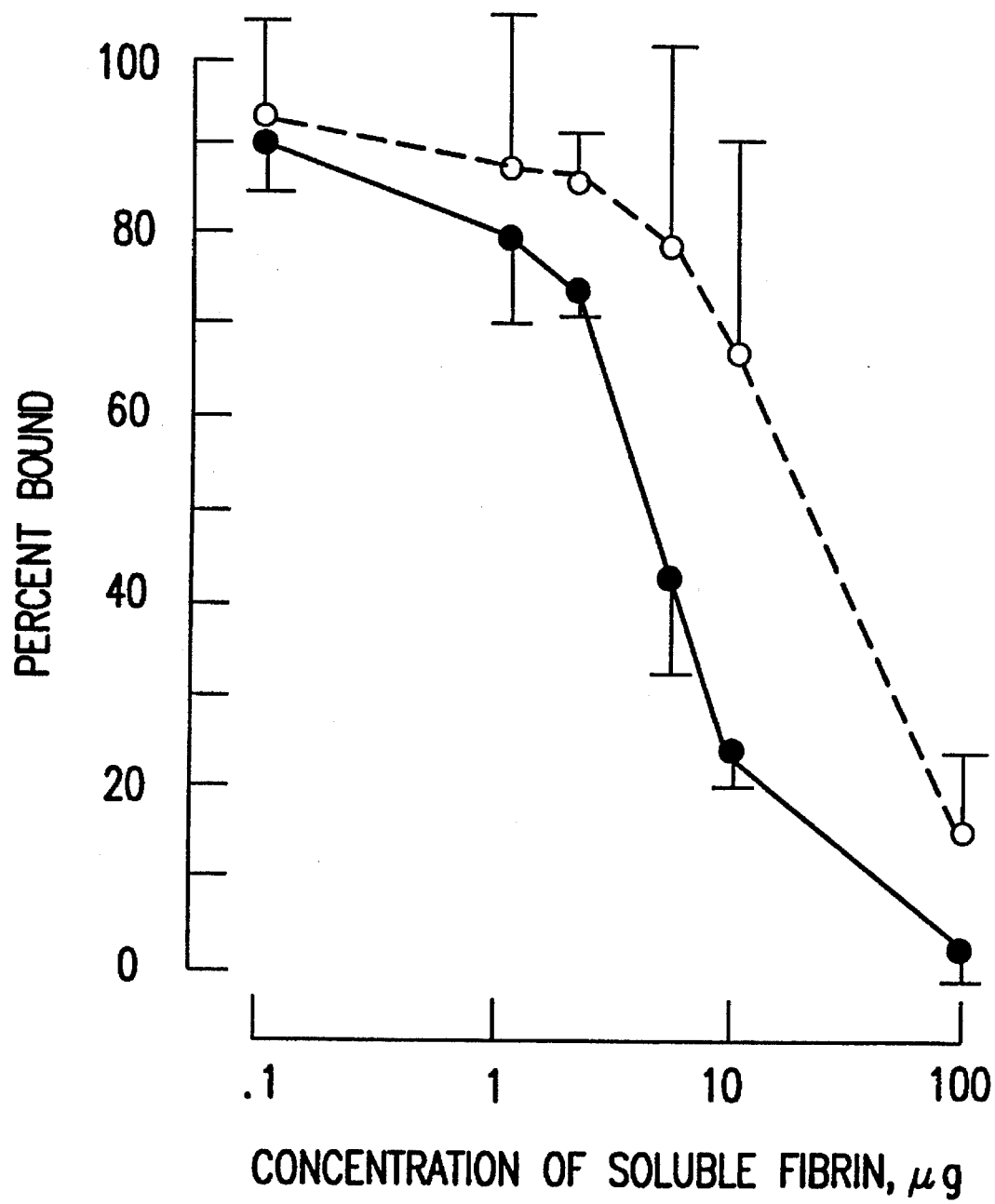
FIG. 6 gives a comparison of the binding behavior of 59D8 antifibrin antibody and recombinant protein. Curves represent the inhibition of antibody binding to solid-phase fibrin monomer by competition with various concentrations of soluble fibrin monomer. Recombinant antibody (dashed lines) requires a slightly higher concentration of soluble fibrin for 50% inhibition than does the antibody (solid lines) and thus binds fibrin somewhat less avidly. This difference is less than 10-fold.

Both the purification scheme and the assays used to follow purification required an intact and functional antigen combining site. In order to more quantitatively compare the recombinant molecule with antibody 59D8, we employed a simple competition assay. This assay measured the ability of soluble fibrin monomer to compete for antibody binding sites against fibrin bound to the bottom of a 96-well plate. Although the assay indicated that the native antibody bound fibrin monomer better than the recombinant protein did, the difference in their binding affinities was less than 10-fold (FIG. 6). It was evident that antibody binding was not significantly impaired in the fusion protein.

Discussion

Extensive analysis of the secreted protein indicated that a 59D8 heavy chain tPA fusion protein was expressed and secreted in association with light chain in the manner predicted. The amount of recombinant protein present in cell culture supernatants, however, appeared to be only 10% of that expected for monoclonal antibodies. By affinity purification, we routinely obtained only 0.1 µg of purified protein per ml of cell culture supernatant or 10 µg per ml in ascites. We monitored the purification with solid-phase immunoassays as described above, and our recoveries from the affinity columns were within the expected range. There were a number of possible reasons for the limited production of recombinant protein. One was that the recombinant protein was being degraded during cell growth or protein purification. In an attempt to limit proteolytic degradation, we added protease inhibitors to the cell cultures. Since no improvement in yield was observed, proteolytic degradation remains a concern.

Other more fundamental problems could be the cause of the low yields of protein. Although messenger RNA of the appropriate size can be seen on Northern blot, transcription of the construct may occur at a low level. Transcription is driven by the natural heavy chain promoter and enhancer, but 3' sequences, which have been shown to be important in regulation of immunoglobulin expression have been excluded from this construct (Gregor et al., *Mol. Cell. Biol.* 6:1903–1916 (1986); Kobrin et al., *Mol. Cell. Biol.* 6:1687–1697 (1986)). In addition, the 3' untranslated region of the chimeric gene was from tPA, a protein that is produced at a low level under normal conditions, and is subsequently stored in the cells where it is produced. It was possible that the 3' UT region of the tPA gene lead to low levels of transcription or translation, or interfered with secretion of the recombinant protein from the cell. Experiments aimed at quantitation of mRNA synthesis, protein synthesis and stability of the recombinant peptide should allow resolution of this problem.

Heavy chain loss variants provided a convenient tool for the reconstitution of the antibody combining site. Their availability made it unnecessary to clone and transfect the productive light chain rearrangement. This approach, of course, depends on being able to transfect these variant cell lines. The two lines used in these experiments were easily transfected using standard techniques, but it is not yet clear whether other SP2/0-derived lines will behave similarly. The amount of light chain that heavy chain loss variants secrete varies. However, some loss variants that secrete small quantities of light chain may be capable of secreting normal amounts of this same light chain when heavy chain synthesis is resumed (Wilde et al., *Eur. J. Immunol.* 10:462–067 (1980)). Little is known about the biological basis for loss of immunoglobulin chain production in these cells and it is possible that the ability of some loss variants to produce light chain as well as heavy chain may be impaired. Our recombinant protein's low level of production could be the result of depressed light chain expression.

The recombinant tPAβ chain has a high level of catalytic activity, and it retained the specific ability to convert plasminogen to plasmin. Earlier studies which linked staphylococcal nuclease and *E. coli* DNA polymerase functions to immunoglobulin heavy chains yielded considerably less effector function activity than the 70% measured in the S-2288 assay (Neuberger et al., *Nature* 312:604–608 (1984); Williams et al., *Gene* 43:319–324 (1986)). This retention of enzymatic activity and substrate specificity indicated that even complex molecules requiring strict folding and formation of multiple intrachain disulfide bonds can be used to form hybrid recombinant proteins. Others have shown that the β chain of tPA was capable of folding correctly and maintaining activity in the absence of the other domains of tPA (MacDonald et al., *Gene* 42:59–67 (1986); von Zonneveld et al., *Proc. Natl. Acad. Sci. USA* 83:4670–4674 (1986)). Our results confirmed the activity of the catalytic chain alone, and indicated that the chain can fold correctly in the context of a different amino terminal sequence. Together, these observations provided evidence for the independent folding of different protein domains.

In summary, we have cloned the heavy chain gene coding for the antigen combining site of an antifibrin antibody and produced a construct that codes for a truncated heavy chain 59D8-tPAβ subunit fusion peptide. The construct was subsequently transfected into heavy chain loss variants of the antifibrin hybridoma. Western blot analysis indicated that the fusion protein had antifibrin antibody activity and retained a level of plasminogen activating activity high enough to be considered similar to that of native tPA.

EXAMPLE 3

Optimization of the Expression and Function of Antibody-Plasminogen Activator Molecules Materials The gene encoding the heavy chain of antifibrin monoclonal antibody 59D8 was cloned from HMW genomic DNA isolated from 59D8 hybridoma cells as previously described (Quertermous et al., *J. Immunol.* 138:2687 (1987); Schnee et al., *Proc. Natl. Acad. Sci. USA* 84:6904 (1987)). The tPA sequence was obtained from a cDNA clone (pPA34′F) that had been constructed from HeLa cell mRNA (Fisher et al., *J. Biol. Chem.* 260:11223 (1985)). Genomic UK DNA was a gift from F. Blasi (International Institute of Genetics and Biophysics, Naples, Italy). The 3′ portion of the human β-globin gene (Lawn et al., *Cell* 21:647 (1980)), cloned in plasmid HβG1-D, was obtained from Dr. T. Maniatis (Harvard University, Cambridge, Mass.). Final constructs were assembled in the pSV2gpt vector that had been modified by R. I. Near to include a polylinker containing a 6 kb Xba 1 restriction fragment encoding the murine λ2b heavy chain constant region (Mulligan et al., *Proc. Natl. Acad. Sci. USA* 78:2072 (1981); Tucker et al., *Science* 206:1303 (1979)).

Synthetic oligonucleotides were purchased from Synthetic Genetics, San Diego, Calif. Reaction conditions and buffers for restriction enzymes, T4 DNA ligase, and the Klenow fragment of DNA polymerase 1 were those listed by the supplier, New England Biolabs (Beverly, Mass.). Transformation of *Escherichia coli* MC1061, preparation of plasmid DNAs, isolation of DNA fragments, and other standard recombinant techniques were carried out as described (Asusbel et al., *Current Protocols in Molecular Biology*, Greene Publishing Associates and Wiley-Interscience, New York (1989)).

Expression Vector Construction

The assembly of pSVtPA(tPA) has been described (Schnee et al., *Proc. Natl. Acad. Sci. USA* 84:6904 (1987)). pSVtPA(Ig) was assembled by first isolating and ligating a 3.3-kb Sac I to Sal I fragment of the λ2b heavy chain gene (containing the 3′ UT region) into pGEM3. A synthetic oligonucleotide encoding RI-XhoI-BamHI-Sac I restriction sites was inserted 5′ of the 3.3 kb λ2b fragment. Then a Bgl II to Bgl II 2.0 kb tPA cDNA fragment encoding the complete 527 amino acid sequence of tPA was ligated into the BamHI site of the synthetic polylinker. The tPA and λ2b fragments were isolated from the pGEM plasmid as a single fragment by Xho I and Sal I digestion. The Xho I to Sal I tPA encoding fragment of pSVtPA(tPA) was then removed to allow insertion of the 5.5 kb tPA-λ2b 3′ UT fragment and generation of the completed pSVtPA(Ig) plasmid.

The expression plasmid pSVUKG(UK) was constructed from a human urokinase gene. Exons coding for 32 kDa single-chain urokinase, from amino acid 144, were assembled in pGEM3 that had been modified to contain an Xho1 site. A coding sequence upstream of the EcoR1 site in Exon VII was constructed from complementary synthetic oligonucleotides. An Xho1 site was incorporated into the 5′ end of this sequence. An internal EcoR1 genomic fragment (1.3 kb) and a 3′ EcoR1-Sma1 fragment (3.4 kb) were assembled into the pGEM3 vector containing the 5′ sequence. An Xho1-Sal1 fragment containing the reconstructed urokinase genomic sequence was then inserted into the pSVtPA(tPA) construct (Fisher et al., *J. Biol. Chem.* 260:11223 (1985)), replacing the tPA sequence.

To generate pSVUKG(β), a synthetic oligonucleotide containing EcoR1-XhoI-BamH1-BglII-SalI-HindIII sites was inserted into pUC19, creating pUC19M. The 5.0-kb Xho1 to Sal1 fragment from pSVUKG(UK) containing the single-chain urokinase gene was inserted into this modified pUC19 plasmid. A synthetic oligonucleotide was made which contained a 5′ BamH1 site, the urokinase sequence 3′ of the BamH1 site of Exon XI to the termination codon, and Bgl2-Sal1 sites on its 3′ end. This oligonucleotide was used to replace the BamH1 to Sal1 fragment from the urokinase-containing pUC19M plasmid above (removing the urokinase 3′ UT domain). The human β-globin 3′ UT sequence was removed from pLL10 (Rothstein et al., Synthetic Adapters for Cloning DNA. *Methods in Enz.* 68:98–109 (1979)), by BamH1 digestion and ligated into the Bgl2 site of pUC19M. Then, the β-globin sequence was removed from this pUC19 vector by BamH1 and Sal1 digestion and ligated into the pUC19M plasmid already containing the single-chain urokinase gene. Finally, the XhoI to Sal1 fragment from this pUC19M vector (containing the urokinase gene beginning at Exon VII and a β-globin 3′ UT element) was substituted for the XhoI to Sal1 fragment in pSVUKG(UK) to generate pSVUKG(β).

pSVUKG(Ig) was constructed by blunt end ligation of the 3.2 Sac1 to Sal1 λ2b 3′ UT sequence from pSV2gpt (see materials section) into the Bgl2-Sal1 sites of the pUC19M vector described above which already contained the desired urokinase protein encoding sequence and termination codon. Then, the Xho1 to Sal1 fragment from this plasmid was used to replace the XhoI to Sal1 fragment of pSVUKG(UK) to generate pSVUKG(Ig).

Transfection and Selection

The isolation of heavy chain loss variants from the parental 59D8 cell line has been described (Schnee et al., *Proc. Natl. Acad. Sci. USA* 84:6904 (1987)). Expression vectors (FIG. 7) were linearized by Sal1 digestion and were transfected by electroporation. A description of the transfection and selection protocols has recently been published (Love et al., *Methods of Enzymology* 178:515–527 (1989), herein incorporated by reference). Essentially, loss variant cells were grown to half confluence, were spun, and were resuspended in 1 ml of buffer containing 20–100 μg/ml plasmid DNA. The cells were exposed to a single pulse of 200 volts (960 μFD) from a Gene Pulser electroporation apparatus (Bio-Rad, Richmond, Calif.). Cells were then transferred to growth medium in the absence of mycophenolic acid.

Selection for clones transfected with the *E. coli* hypoxanthine guanine phosphoribosyltransferase gene (gpt) was begun 3 days after electroporation by exposure to medium containing mycophenolic acid (0.5 μg/ml), xanthine (100 μg/ml) and hypoxanthine (15 μg/ml).

Protein Concentration Determinations

Cells were allowed to grow to maximal confluence in 100 mm petri dishes (for approximately 48–72 hours) before harvesting of conditioned medium. Microtiter plates were coated with 25 μl of fibrin monomer solution (0.01 mg/ml). Conditioned media from each transfected cell line was centrifuged, filtered, then serially diluted with phosphate buffered saline (10 mM potassium phosphate, 0.15M NaCl, pH 7.4). After the plates had been washed with distilled water, the wells were blocked by incubation for at least an hour with 50 μl of a 10% horse serum solution to prevent nonspecific protein binding. The wells were rinsed again with distilled water, and 25 μl of each conditioned medium dilution was incubated for 2 hours. The cell medium was rinsed from the plates, and 25 μl of $^{125}$I-labeled goat anti-(mouse Fab) (50,000 cpm/25 μl) was added and allowed to incubate for 1 hour. The concentration of recombinant protein (assumed to be equal to functional 59D8 activity) was determined relative to a standard curve generated from measurements obtained with purified 59D8 antibody.

RNA Isolation and Analysis

RNA was prepared by conventional methods (Lijnen et al., *J. Biol. Chem.* 265:5677–5683 (1990)) from 59D8 myelomas, 59D8 heavy-chain loss variants, and each of the five transfected cell lines. RNA samples (10 μg/lane) were electrophoresed on a formaldehyde/agarose gel and were transferred to nitrocellulose filters. The filters were hybridized with a $^{32}$P labeled DNA probe that specifically bound to the 59D8 VDJ region. The VDJ probe consisted of a cloned 2.1 kb genomic DNA fragment spanning the VDJ exon. Equal loading of sample RNAs into lanes was confirmed by probing blots with an actin probe. Actin mRNA was detected using a 700 basepair Pst1 fragment of pact-1 plasmid (Spiegelman et al., *J. Biol. Chem.* 258:10083 (1983)) provided by Lloyd Klickstein, Massachusetts General Hospital, Boston, Mass.

Nuclear Runoff Transcription Analysis

The rate of transcription of the pSVUKG(UK) gene relative to that of the endogenous gene in the 59D8 hybridoma was measured essentially as described by Zagardo et al. (*Nature* 304:277 (1983)). Nuclei were harvested from both cell lines and were incubated in $^{32}$P-labeled uridine triphosphates to label nascent RNA transcripts. The radiolabeled RNA was purified and hybridized to equal amounts of Eco R1-digested pSVUKG(UK) plasmid DNA that had been separated on an agarose gel and transferred onto nitrocellulose. Before hybridization, the number of counts/minute incorporated into each sample was determined to allow normalization for variable label in each hybridization. A LKB Ultrascan XL Laser Densitometer was used to determine the relative intensity of the hybridization signals.

Results

Protein Expression Levels

The tPA and urokinase plasmids shown in FIG. 7 were transfected into heavy chain loss variant 59D8 cells. Five unique, transfected cell lines were established, each secreting its encoded fusion protein. To measure the level of 59D8 antibody activity (and thus fusion protein secretion), the conditioned medium from each transfected cell line was analyzed with the radioimmunoassay, supra. Table 1 contains measurements of protein secretion for each of the cell lines. The parental 59D8 hybridoma secreted 7.6–10 μg/ml of functional 59D8 antibody, while the cell line pSVtPA(tPA) secreted a maximum of 0.025 μg/ml fusion protein. However, pSVtPA(Ig), which was modified from pSVtPA(tPA) to contain an Ig 3' UT domain, secreted as much as 2.5 μg/ml. This represented an approximate 100-fold increase in protein secretion.

TABLE 1

| Cell Line | Protein Secreted | Protein Level (μg/ml) | Increase |
| --- | --- | --- | --- |
| 59D8 | 59D8 | 7.6–10 | — |
| pSVtPA(tPA) | r59D8-tPA(B) | 0.008–0.025 | — |
| pSVtPA(Ig) | r59D8-tPA(AB) | 0.25–2.5 | 100x |
| pSVUKG(UK) | r59D8-scuPA | 0.015–0.06 | — |
| pSVUKG(Ig) | r59D8-scuPA | 1.0–4.05 | 68x |
| pSVUKG(β) | r59D8-scuPA | 1.0–4.1 | 68x |

Similarly, pSVUKG(UK) secreted very low levels of fusion protein (0.015–0.06 μg/ml) compared to pSVUKG(Ig) and pSVUKG(β) (1–4.1 μg/ml). This corresponded to enhancements in protein secretion of 16 to 68 fold. The increases in protein expression produced by substitution of either the β-globin or λ2b 3' UT elements were approximately equal.

RNA Transfer Blot and Nuclear Run-off Analysis

RNA transfer blot analysis was performed using equal amounts of total cellular RNA from 59D8 hybridomas and each of the five transfected cell lines. Heavy chain loss variant cells (L2LV) were used as a negative control. Equal loading of the lanes was confirmed using an actin probe as described, The quantity of mRNA encoding 59D8 fusion protein in pSVtPA(tPA) and pSVUKG(UK) cells was confirmed to be dramatically lower than the amount of 59D8-encoding mRNA in the 59D8 myeloma cells. In the lane containing pSVtPA(tPA), no detectable message was visible. In pSVUKG(UK) there was a faint message corresponding to the predicted size of 2.7 KB.

On a similar RNA transfer blot mRNA levels were compared in pSVtPA(Ig), pSVUKG(Ig), and pSVUKG(β) to 59D8 parental cells. In these transfectants, which contained genes with an immunoglobulin or β-globin 3' UT domain, the band intensities suggested mRNA levels which were more comparable to 59D8 cells. As shown in Table 1, the increased levels of mRNA in pSVtPA(Ig), pSVUKG(Ig), and pSVUKG(β) compared with pSVtPA(tPA) and pSVUKG(UK) were associated with corresponding increases in protein secretion.

To determine if the reduced levels of mRNA observed in the pSVUKG(UK) cell line compared to the native 59D8 hybridoma resulted from a lower rate of gene transcription, nuclear run-off transcription analysis was performed. As described above, the rate of mRNA transcription of each gene was assessed by probing a Southern blot containing EcoRI digested pSVUKG(UK) plasmid DNA. The relative intensities of bands corresponding to DNA fragments common to pSVUKG(UK) and 59D8 were measured using a LKB Ultrascan XL Laser densitometer to determine the relative rates of immunoglobulin heavy chain gene transcription. Table 2 contains relative values representing the densities of bands (after normalization for variable cpm used to hybridize) resulting from radiolabeled mRNA transcripts which annealed to the 2.5 Kb VDJ exon fragment and the 1.9 Kb DNA fragment containing the heavy chain constant region sequence. The blots were exposed for 72 and 168 hour periods. The VDJ region bands yielded by mRNA isolated from pSVUKG(UK) nuclei were consistently more dense than those produced from mRNA purified from 59D8. This was also true of bands corresponding to the constant region sequences (despite the fact that 59D8 is a λ1 antibody). Although, we suspect the greater density of pSVUKG(UK) bands compared to corresponding 59D8 bands is within the error of the technique, these data suggest the rate of transcription in the transfected pSVUKG(UK)

gene was at least as great as that of the endogenous 59D8 gene in the parental cell line. Thus, it appears unlikely that the differences in mRNA levels observed in pSVtPA(tPA) and pSVUKG(UK) transfectants compared to pSVtPA(Ig), pSVUKG(Ig) and pSVUKG(β) related to augmentation of gene transcription rates.

TABLE 2

Relative transcription rates of the transfected pSVUKG(UK) and endogenous 59D8 heavy chain genes

|  | 59D8 | | pSVUKG(UK) | |
| --- | --- | --- | --- | --- |
|  | 72 hr | 168 hr | 72 hr | 168 hr |
| 2.5 kb VDJ Region | 0.6 | 1.5 | 1.9 | 3.7 |
| 1.9 kb Heavy chain constant region | 0.3 | 0.4 | 0.6 | 1.5 |

Discussion

The technique of creating novel proteins by transfection of recombinant genes into cells is becoming increasingly important (Morrison et al., *Adv. Immunol.* 44:65 (1989)). Once incorporated into the genome of an appropriate cell line, a transfected gene can be transcribed and translated and the protein product assembled, processed, and secreted. Lymphoid cells have proven to be ideal recipients for transfection of immunoglobulin or immunoglobulin fusion protein genes (Morrison et al., supra; Neuberger et al., *Nature* 312:604 (1984); Dorai et al., *J. Immunol.* 139:4232 (1987)). Unfortunately, a major limitation in the application of this technology has been low levels of protein expression from transfected genes (Morrison, supra; Dorai et al., supra). It has been suggested that transfectomas secrete poorly relative to hybridomas because these cells lack sufficient quantities of the necessary transcriptional factors (Maeda et al., *Cell* 45:25 (1986); Sen et al., *Cell* 46:705 (1986); Singh et al., *Nature* 319:154 (1986)).

Our approach to resolving the problem of low protein expression of transfected genes involved taking advantage of the role that 3' UT sequences play in determining mRNA stability (Kabnick et al., *Mol. Cell. Bio.* 8:3244 (1988); Purvis et al., *Nucleic Acids Res.* 15:7951 (1988); Müllner et al., *Cell* 53:815 (1988); Shaw et al., *Cell* 46:659 (1986); Gregor et al., *Immunol. Reviews* 89:31 (1986)). Kabnick and Housman have previously described prolongation of short-lived mRNA transcripts by substitution of a β-globin 3' UT element (*Mol. Cell. Bio.* 8:3244 (1988)). In this patent application, we describe the successful substitution of the human β-globin or the mouse λ2b immunoglobulin 3' UT domains in transfected genes to increase both the levels of mRNA and protein secretion from genes transfected into hybridomas.

Stable transfected cell lines were established for each of the genes shown in FIG. 7 and the level of protein secretion for each cell line was determined (Table 1). RNA transfer blots were analyzed to determine if transfectants which secreted lower levels of protein also contained similarly diminished levels of mRNA. After establishing that low levels of protein secretion did correlate with low mRNA levels, nuclear run-off analysis demonstrated that there was not a significant difference in the rates of transcription of the transfected pSVUKG(UK) gene (which produced low levels of mRNA) and the endogenous 59D8 heavy chain gene (which produced high levels of mRNA). While we have not directly determined mRNA half-lives for each of the transfected genes, the mechanism of increased mRNA levels in the genes modified to contain an immunoglobulin or β-globin 3' UT element appears most likely to relate to increased mRNA stability.

The exact mechanisms by which 3' UT domains contributed to mRNA stability have not been defined. Proposed mechanisms have included the suggestion that a specific AU-rich 3' UT sequence can promote mRNA degradation (Shaw et al., *Cell* 46:659 (1986)). Others have proposed that mRNA 3' UT regions can form secondary structures which might mediate mRNA stability by impeding access to exonucleases (Müllner et al., *Cell* 3:815 (1988); Shaw et al., *Cell* 46:659 (1986); Gregor et al., *Immunol. Reviews* 89:31 (1986); Freier et al., *Proc. Natl. Acad. Sci. USA* 83:9373 (1986); Zucker et al., *Nucleic Acids Res.* 9:133 (1981)). Analysis of the human β-globin and mouse λ2b 3' UT sequences using computer models suggest that both sequences can potentially form stable loop structures (Zucker et al., *Nucleic Acids Res.* 9:133 (1981)) (data not shown).

Despite the presence of 3' UT elements from the human β-globin or mouse Ig genes, transfectomas (pSVtPA(Ig), pSVUKG(Ig), and pSVUKG(β)) never produced mRNA or protein levels equal to the original hybridoma. This suggested that factors other than the 3' UT element are involved in this determination of mRNA and protein levels. However, these experiments indicated that both mRNA and protein levels may be increased in transfectants by modification of the 3' UT element in the transfected gene. It is interesting to speculate if simultaneous 3' UT element modification and DHFR-amplification (Dorai et al., *J. Immunol.* 139:4232 (1987)) might achieve transfectomas capable of secreting protein levels exceeding the original hybridomas.

EXAMPLE 4

Recombinant 59D8-scuPA Fusion Protein with High Affinity for Fibrin and Increased Thrombolytic Potency In Vitro and In Vivo A genomic sequence coding for a portion of the mouse immunoglobulin γ2b constant region, genomic DNA for the rearranged heavy chain gene of antibody 59D8, and a cDNA coding for the catalytic light chain of human tPA was previously cloned into plasmid pSV2gpt (Schnee et al., *Proc. Natl. Acad. Sci. USA* 84:6904 (1987); Love et al., In *Methods in Enzymology*, Langone, J. J. (ed.), Academic Press, New York, pp. 515–527 (1989), both herein incorporated by reference). The resulting expression plasmid, pSV5PA(tPA), was used as a starting point for the constructs described here (FIG. 8A). scuPA genomic DNA encoding amino acids 144 to 411 was then inserted into pSV5PA(tPA) in place of the tPA light chain gene (a plasmid containing genomic sequence encoding the entire scuPA molecule was a gift from F. Blasi (International Institute of Genetics and Biophysics, Naples, Italy). An additional portion of the mouse immunoglobulin γ2b constant region, containing sequences coding for the entire CH2 domain and a portion of the CH3 domain, was also ligated into pSV5PA(tPA). The resulting expression plasmid, pSVUKG(UK) (FIG. 8A), was transfected into 59D8 heavy-chain loss variant hybridoma cells by electroporation, as described by Schnee et al., *Proc. Natl. Acad. Sci. USA* 84:6904 (1987); Love et al., In *Methods in Enzymology*, Langone, J. J. (ed.), Academic Press, New York, pp. 515–527 (1989), both herein incorporated by reference), and recombinant protein was purified from the culture supernatant by affinity chromatography.

Although initial assays of the culture supernatant indicated the presence of scuPA and 59D8 antigens, and both activities, the levels of expressed r59D8-scuPA protein was extraordinarily low (FIG. 8B), on the order of 30 to 200 ng/ml of culture supernatant. Northern blot analysis with poly A+RNA from P220R-15 cells, a stable, subcloned line expressing pSVUKG(UK), that had been probed with two $^{32}$P-labeled oligonucleotides (one specific for mouse IgG, the other specific for scuPA) showed a low steady-state mRNA level (relative to that of antibody 59D8 in control cells) consisting of a single, 2.7 kb transcript (as discussed in Example 3). Nuclear run-off experiments indicated that this low steady-state mRNA level was likely due to mRNA instability rather than to a reduced transcription rate (as discussed in Example 3). We then replaced the 3' UT domain of scuPA in pSVUKG(UK) with the 3' UT domain of β globin (pSVUKG(β), FIG. 8A) or immunoglobulin (pSVUKG(Ig), FIG. 8A). This change produced an approximately 100-fold improvement in levels of protein expression (FIG. 8B), with corresponding increases in steady-state mRNA levels (not shown). The protein expression level was similarly greater for the plasmid pSVUKc(Ig) (FIG. 8A), in which the genomic DNA encoding amino acids 144 to 411 of scuPA had been replaced with cDNA encoding the same sequence and the PA 3' UT domain had been replaced with the immunoglobulin 3' UT domain (not shown). The r59D8-scuPA protein tested in the in vitro and in vivo studies that follow came from the transfection (by electroporation) of the pSVUKG(β) plasmid into 59D8 heavy-chain loss variant cells (L2LV).

Fibrinogen Assays

The fibrinogen content of samples of citrated human or rabbit plasma was determined by two methods. Clottable fibrinogen was measured by the method of Clauss, *Acta Chir. Scand.* 90:419 (1957), and total fibrinogen was determined by sodium sulfite precipitation.

Plasma Clot Assay

The method of Lijnen et al. (*Thromb. Haemostas.* 52:308 (1984)) was used with the following modifications. Human fresh-frozen plasma obtained from at least four donors was pooled, aliquoted, and refrozen. Immediately before each experiment, the activities of scuPA and the hybrid immunoglobulin molecules were calibrated using the S-2288 assay (i.e., the peptidase activities of the PAs and the hybrid molecules were determined and appropriate dilutions were made so that the peptidase activity (in units/ml) was identical for each sample). Plasma clots were made by adding each of the following to fresh-frozen plasma: thrombin, 8 NIH units/ml; 0.5M CaCl$_2$, 100 µl/ml; and $^{125}$I-labeled human fibrinogen (IBRIN)™, 40,000 cpm/ml (Amersham, Chicago, Ill.). The solution was immediately drawn into Silastic tubing (internal diameter (I.D.)=4 mm), and was incubated at 37° C. for 30 minutes. Silastic tubing containing clotted fresh-frozen plasma was cut into 1.5 cm sections, yielding clots of 0.2 ml. These clots were then washed in 0.15M NaCl before use. Each clot was placed in a plastic tube, was counted, and was suspended in 1 ml fresh-frozen plasma (from the same pool). Experiments were initiated by the addition of a PA (or hybrid molecule of PA and antibody). At 30 minute intervals, an aliquot of the fresh-frozen plasma was removed from each tube for counting. Samples were saved at the end of the experiment for determination of fibrinogen levels.

In vivo Thrombolysis

The rabbit jugular vein model of Collen et al. (*J. Clin. Invest.* 71:368 (1983)) was used. After sedation of the rabbit with acetopromazine and ketamine, a paramedial incision was made from the right mandible to above the right clavicle. The external jugular vein was isolated by dissection, and its branches were ligated and separated. A segment of woolen thread was introduced to anchor the clot. After bleeding ceased, vascular clamps were placed so as to isolate this segment of the external jugular vein. The components of the clot were introduced into the isolated vein segment. These components consisted of approximately 500,000 cpm of $^{125}$I-labeled human fibrinogen (each sample was counted before use), 100 µl of packed human red blood cells, 100 µl of human fresh-frozen plasma, 10 µl of 0.5M CaCl$_2$ and 10 µl of bovine thrombin (8 NIH units). After 30 minutes, the vascular clamps were removed and blood flow was restored. A sample of blood was taken immediately after the clamps were released to determine radioactivity that was not incorporated into the thrombus. Measured amounts of PA were diluted to a volume of 25 ml, and were delivered via the marginal vein of the contralateral ear over 4 hours by an infusion pump. Lost counts were determined by counting syringes, gauze sponges and tubing. Six hours after initiation of the infusion, the entire vein segment was isolated, removed and counted. Percent lysis was determined as the ratio of the counts remaining at the termination of an experiment over the net counts at the beginning.

Milligram quantities of r59D8-scuPA protein were produced by growing cells to high density (total mass of approximately 4×10$^{10}$ cells) in DMEM with 10% FCS in the extrafiber space of a CellMax™ (Type B) bioreactor (Cellco Advanced Bioreactors, Kensington, Md. 20895) containing cellulose acetate hollow fibers with a sieving coefficient of approximately 4 kDa. Culture medium was harvested at 12 hour intervals and were immediately frozen at −70° C. After the aliquots had been thawed and pooled, r59D8-scuPA was purified from the medium (the initial concentration of recombinant protein varied between 0.05 and 0.3 mg/ml) by affinity chromatography on a resin containing Sepharose linked to the heptapeptide epitope for antibody 59D8 (Runge et al., *Biochemistry* 27:1153 (1988)). The eluate contained a mixture of r59D8-scuPA (15% to 35%) and enzymatically cleaved r59D8-scuPA (85% to 65%). (Either thrombin or plasmin can cleave the scuPA portion of r59D8-scuPA into LMW two-chain urokinase.) r59D8-scuPA was obtained by passing this mixture through a column of benzamidine-Sepharose. Benzamidine-sepharose chromatography was performed as described by Runge et al., (*Proc. Natl. Acad. Sci. USA* 84:7659 (1987)). Rather than being used for affinity binding of the desired product (Haber et al., *Science* 243:51 (1989)), benzamidine-Sepharose was used to remove two chain r59D8-scuPA from the mixture of single- and two-chain forms. Purified r59D8-scuPA (0.05 to 0.5 mg/ml in Tris-glycine buffer, pH 7.4) was used immediately in assays or frozen at −70° C., at which it remained stable for up to 6 weeks.

The predicted MW of purified r59D8-scuPA was approximately 95 kDa: ~38 kDa for the truncated 59D8 "heavy chain" (lacking CH3), ~32 kDa for scuPA (not accounting for glycosylation on either component molecule) and ~25 kDa for the 59D8 "light chain." SDS-polyacrylamide gel electrophoresis was performed according to the method of Laemmli (*Nature* 227:680 (1970)) as described by Runge et al. (*Biochemistry* 27:1153 (1988)). Proteins were either visualized with Coomassie Brilliant Blue R or were transferred by electrophoresis to a nitrocellulose filter (Bode et al., *Circulation* 81:1974 (1990)). These filters were blocked with a 1% BSA solution and were then probed with phosphatase-conjugated goat-antimouse IgG (ELISAmate kit, Kirkegaard and Perry Laboratories, Gaithersburg, Md.). The molecular weight standards used were (in kDa): 200, myson; 116.3, β galactosidase; 97.4, phosphorylase B; 66.3, bovine serum albumin; 45, ovalbumin; 31, carbonic anhydrase; and 21, soybean trypsin inhibitor. Other lanes contained purified r59D8-scuPA, scuPA (purified scuPA from Sandoz contains human serum albumin, as a stabilizer, present at approximately 66 kDa), and affinity-purified antibody 59D8. Molecular weight calculations were made from unknown bands on the basis of relative mobility in both reduced and nonreduced gels in comparison with the known standards.

Under nonreducing conditions, SDS-polyacrylamide gel electrophoresis of purified r59D8-scuPA revealed a single predominant band at ~104 kDa, which accounted for all the predicted components. The band contained immunoglobulin and scuPA epitopes by Western blot analysis. The presence of a small amount of heavy chain-scuPA fusion peptide was evidenced by the band at 78 kDa. Under reducing conditions, major bands included the heavy chain-scuPA fusion peptide (78 kDa) and light chain (25 kDa) species; the two intermediate bands most likely resulted from degradation of the heavy chain-scuPA fusion peptide by thrombin (at $Arg^{156}$-$Phe^{157}$) or plasmin (at $Lys^{158}$-$Ile^{159}$). The identity of these bands was confirmed by Western blot analysis.

To evaluate the functional properties of r59D8-scuPA, we compared the catalytic activity and $K_m$ for plasminogen of plasmin-cleaved r59D8-scuPA with those of LMW two-chain urokinase, and compared the fibrin-binding activity with that of native 59D8. The catalytic activity of tissue culture-derived scuPA was 85,000 IU/mg. This material was >95% uncleaved (i.e., single-chain) when latent activity was compared with activity after cleavage to HMW two-chain urokinase (scuPA and r59D8-scuPA were converted to the two-chain form with plasmin-Sepharose (Runge et al., *Proc. Natl. Acad. Sci. USA* 84:7659 (1987); Dewerchin et al., *Eur. J. Biochem.* 185:141 (1989))). Preparations of r59D8-scuPA were 90% single chain, with a catalytic activity of 26,000 IU/mg of protein after conversion to the two-chain form. Given the contribution, on a molar basis, of the 32 kDa scuPA portion of the 104 kDa r59D8-scuPA molecule, the activity of the scuPA portion was 83,900 IU/mg of scuPA. This was not significantly different from the activity of native scuPA. In addition, the $K_m$ (16.6 µM) of the plasmin-cleaved (two-chain) form of r59D8-scuPA did not differ significantly from that of LMW two-chain urokinase (9.1 µM) (FIG. 9A). The fibrin-binding activity of r59D8-scuPA did not differ significantly from that of LMW two-chain urokinase (9.1 µM) (FIG. 9A). The fibrin-binding activity of r59D8-scuPA (native scuPA does not bind fibrin directly) was compared with that of native 59D8 by measuring the binding of serial dilutions of either 59D8 or r59D8-scuPA to fibrin monomer-coated, 96-well plates. The fibrin binding of both species was comparable within the error of the method, indicating that the fibrin-binding domain of r59D8-scuPA did not differ significantly from that of native 59D8 (FIG. 9B).

In a human plasma clot assay (Lijnen et al., *Thromb. Haemostasis* 52:308 (1984)), r59D8-scuPA was 6 times more potent than scuPA (p<0.0001) (FIG. 10A). The results were even more striking in vivo, when tested in the rabbit jugular vein model (the in situ formation of a human thrombus in the rabbit's vein) (Runge et al., *Proc. Natl. Acad. Sci. USA* 84:7659 (1987); Collen et al., *Fibrinolysis* 3:197 (1989)). Compared with scuPA, r59D8-scuPA displayed a remarkable 20-fold increase in the thrombolytic potency in vivo over the entire dose-response range (p<0.0001) (FIG. 10B). r59D8-scuPA did not cause a decrease in fibrinogen concentration until 83% lysis was reached, at which point the fibrinogen concentration was 79% that of the control.

r59D8-scuPA demonstrated that it was possible to design a PA dimer in which the activities of the components, though comparable to those of the native proteins, manifest increased selectivity and potency when combined in a single molecule. This approach promised to address two of the remaining problems in PA therapy: bleeding and incomplete lysis.

EXAMPLE 5

Increased Thrombolytic and Antithrombotic Potency of r59D8(—CDWAH$_2$)-scuPA in Baboons To define the determinants for full catalytic and thrombus-binding activity, a panel of hybrid PAs was constructed and characterized in vitro. In vivo evaluation was subsequently performed in baboon models of thrombolysis and thrombosis for the most efficient hybrid PA identified in vitro, AFA-scuPA. Non-human primates were selected for study because of their vascular, hemostatic and immunologic similarities to humans (Hanson et al., *Thromb. Haemostas.* 58:801–805 (1987); Hanson et al., *Proc. Natl. Acad. Sci. USA* 85:3184–3188 (1988); Gruber et al., *Circulation* 82:578–585 (1990); Cadroy et al., *J. Lab. Clin. Med.* 114:349–357 (1990)). The hybrid r59D8(—CH$_2$)-scuPA, which is also known as "AFA-scuPA", offers greatly improved thrombolytic and antithrombotic efficacy with less impairment of hemostasis, compared to thrombolytic agents currently in clinical use. The plasmid p220RX (FIG. 11) expressed r59D8(—CH$_2$)-scuPA. The plasmid p220RX was constructed by deletion of the CH$_2$ fragment from pSVUK-G(Ig).

Materials and Methods

PAs for in civo Use

Several recombinant hybrid PAs have been developed by this and other laboratories (Holvoet et al., *J. Biol. Chem.* 266:19717–19724 (1991); Runge et al., *Proc. Natl. Acad. Sci. USA* 88:10337–10341 (1991); Schnee et al., *Proc. Natl. Acad. Sci. USA* 84:6904–6908 (1987)). The construction of r59D8(—CH$_2$)-scuPA has been previously described (Runge et al., *Proc. Natl. Acad. Sci. USA* 88:10337–10341 (1991), herein incorporated by reference). In r59D8(—CH$_2$)-scuPA almost the entire heavy chain of antibody 59D8 is present, including the CH1, CH2 and the majority of the CH3 domains. Although a second isoform of r59D8(—CH$_2$)-scuPA lacks the Fc domain of antibody 59D8, the thrombolytic potencies for these isoforms were equivalent. The advantage of r59D8(—CH$_2$)-scuPA is that it can be produced in larger amounts with more single-chain product than r59D8-scuPA can be produced. SDS-PAGE was performed according to Laemmli (*Nature* 227:680–685 (1970)) as described previously (Runge et al., *Proc. Natl. Acad. Sci. USA* 88:10337–10341 (1991)). Proteins were either visualized with Coomassie brilliant blue R or were transferred by electrophoresis to a nitrocellulose filter for Western blotting (Runge et al., *Proc. Natl. Acad. Sci. USA* 88:10337–10341 (1991)) using either a goat anti-mouse IgG antibody or a goat anti-human urokinase antibody (both obtained from American Diagnostica). Modified hybridoma cells expressing the isoform of r59D8(—CH$_2$)-scuPA that lacked the Fc domain Fab produced more protein/ml of culture supernatant, and the percentage expressed in the single chain form was increased, allowing more efficient purification of large quantities of this molecule.

For both isoforms, transfection of heavy chain hybridoma cells was performed as described previously (Runge et al., *Proc. Natl. Acad. Sci. USA* 88:10337–10341 (1991); Schnee et al., *Proc. Natl. Acad. Sci. USA* 84:6904–6908 (1987)). Cells were grown to high density (total cell mass of approximately 4×10¹⁰ cells) in AIM-V medium (Gibco) with 1% FCS and aprotinin (600 TIU/L medium) in the extrafiber space of a CellMax™ hollow fiber (type B) bioreactor (Cellco Advanced Bioreactors, 5516 Nicholson Lane, Kensington, Md. 20895). Affinity purification was performed as described previously (Runge et al., *Biochemistry* 27:1153–1157 (1988); Runge et al., *Proc. Natl. Acad. Sci. USA* 88:10337–10341 (1991)). The final purified r59D8(—CH₂)-scuPA and r59D8(—CH₂)-scuPA-Fab were approximately 95% single chain, and had activities of 20–20,000 IU/mg (batch to batch variation). This material was used for these experiments, aliquots being thawed immediately prior to each experiment.

Comparison of r59D8-scuPA and r59D8(—CH₂)-scuPA r59D8-scuPA which contained more of the Fc domain and r59D8-(—CH₂)-scuPA which contained less of the Fc domain, were compared using functional and structural assays. In vitro human plasma clot assays and limited in vivo experiments were found to be equivalent (data not shown). SDS-PAGE and Western blot analysis showed the predicted composition and size of the isoform of r59D8(—CH₂)-scuPA lacking the Fc domain (FIG. 12, all six panels). Affinity purified r59D8(—CH₂)-scuPA-Fab preparations contained a major band of 90 kDa when electrophoresed under non-reducing conditions. This band represented the fusion protein r59D8(—CH₂)-scuPA since the 90 kDa protein was recognized by both anti-mouse IgG and anti-human urokinase antibodies. There was also a minor band of 180 kDa that probably represented a dimer of r59D8(—CH₂)-scuPA-Fab. Under reducing conditions, affinity purified r59D8(—CH₂)-scuPA-Fab consisted of two bands with molecular weights of 63 and 27 kDa. The 63 kDa protein was recognized by both anti-IgG and anti-UK antibodies and the 27 kDa protein was recognized only by the anti-IgG antibodies. These findings were consistent with the identity of the 63 kDa protein as a fusion protein of rscuPA32 and the heavy chain of 59D8 Fab (lacking the Fc domain), and the 27 kDa protein as the 59D8 light chain. For the experiments described here both isoforms of r59D8(—CH₂)-scuPA were used, since no significant functional or structural differences were present. Aliquots from a single pooled sample of the r59D8(—CH₂)-scuPA isoform lacking Fc were used for the thrombolysis experiments and aliquots from a single pooled sample of the r59D8(—CH₂)-scuPA containing Fc was used for the inhibition of thrombosis experiments.

Recombinant single chain rtPA (purchased from Genentech, South San Francisco, Calif.) and recombinant high molecular weight rscuPA (a gift from Farmitalia, Milan, Italy) were also used in the studies described here. Both rtPA and rscuPA were dissolved in the sterile aqueous buffer supplied by the manufacturer to a final concentration of 1 mg/ml (14.2 nMol/ml). Calculations of molar amounts of rtPA, rscuPA, and r59D8(—CH₂)-scuPA were performed immediately prior to each experiment and were based on the protein concentration and the measured amidolytic activity of the pools of material used in these experiments (S-2288 assay for r-tPA or S-2444 assay for rscuPA and r59D8(—CH₂)-scuPA). The amidolytic activities of rscuPA and rtPA were 125,000±5,000 IU/mg and 500,000±8,000 IU/mg, respectively.

TABLE 3

Measurement of Plasma Parameters in the Thrombolysis Experiments.

| | | | Fibrinogen | | | tPA | | uPA | |
|---|---|---|---|---|---|---|---|---|---|
| | n | time (min) | decrease (mg/ml) | α-2 AP (% of control) | D-Dimer (μg/ml) | Antigen (pmol/ml) | Activity (U/ml) | Antigen (pmol/ml) | Activity (U/ml) |
| Controls | 5 | 0 | — | 97.4 ± 1.48 | 901.2 ± 154 | .059 | 1.1 | — | — |
| | | 165 | — | 90.0 | — | .042 | 0.36 | — | — |
| Heparin 100 U/kg | 5 | 0 | — | 93.6 ± 1.97 | 606.7 ± 104 | .058 | — | 0.0 | 0.0 |
| | | 165 | 0.15 ± 0.13 | 97.0 ± 0.36 | 1311.9 ± 266 | .049 | — | 0.0 | 0.0 |
| rtPA 2.8 nmol/kg | 4 | 0 | — | 81.3 ± 3.29 | 946.6 ± 260 | .050 ± .005 | 0.76 ± 0.2 | — | — |
| | | 165 | 0.15 ± 0.08 | 71.3 ± 5.25 | 3988.0 ± 649 | .229 ± .024 | 1.46 ± 0.3 | — | — |
| rtPA 14.2 nmol/kg | 5 | 0 | — | 98.0 ± 1.51 | 1256.4 ± 650 | .067 ± .011 | 0.59 ± 0.06 | — | — |
| | | 165 | 0.4 ± 0.14 | 56.0 ± 11.03 | 4206.2 ± 1103 | 1.24 ± .16 | 7.99 ± 2.02 | — | — |
| rtPA 28.5 nmol/kg | 1 | 0 | — | 95.0 | 978.4 | .034 | 1.73 | — | — |
| | | 165 | 0.2 | 42.0 | 3520 | 2.16 | 32.5 | — | — |
| rscuPA 2.8 nmol/kg | 3 | 0 | — | 97.0 ± 2.54 | 978.5 ± 158 | — | — | 0.04 ± 0.03 | 0.0 ± 0 |
| | | 165 | 0.17 ± 0.49 | 96.0 ± 2.08 | 2639.9 ± 404 | — | — | .106 ± .005 | 0.18 ± 0.04 |
| rscuPA 14.2 nmol/kg | 4 | 0 | — | 91.7 ± 5.25 | 820.6 ± 211 | — | — | 0.0 ± 0 | 0.0 ± 0 |
| | | 165 | 0.47 ± 0.8 | 74.2 ± 8.90 | 4155.9 ± 661 | — | — | .972 ± .198 | 0.96 ± 0.25 |
| rscuPA 28.5 nmol/kg | 2 | 0 | — | 98.0 ± 1.98 | 569.3 ± 178 | — | — | 0.0 ± 0 | 0.0 ± 0 |
| | | 165 | 0.25 ± 0.05 | 29.5 ± 6.51 | 9371.6 ± 2843 | — | — | 2.84 ± .808 | 2.9 ± 1.77 |
| rscuPA 72.2 nmol/kg | 2 | 0 | — | 97.0 ± 2.97 | 689.3 ± 190 | — | — | 0.0 ± 0 | 0.0 ± 0 |
| | | 165 | 2.06 ± 0.25 | 0 | 12853.0 ± 5813 | — | — | 31.95 ± 25.4 | 7.1 ± 7.0 |
| r59D8 (—CH₂)-scuPA 1.89 nmol/kg | 3 | 0 | — | 94.3 ± 3.75 | 677.3 ± 167 | — | — | 0.0 ± 0 | 0.0 ± 0 |
| | | 165 | 0.31 ± 0.28 | 79.0 ± 23.61 | 2778.0 ± 852 | — | — | .010 ± .005 | 0.0 ± 0 |

Thrombolytic, Antithrombotic and Antihemostatic Effects In Vivo

Animal Studies

Eighteen normal male juvenile baboons weighing 9–11.5 kg were used in these studies. All procedures were approved by the Institutional Animal Care and Use Committee (Emory University) in compliance with the National Institutes of Health guidelines (Guide For Care and Use of Laboratory Animals, 1985), Public Health Service policy, the Animal Welfare Act, and related university policies. Before all experiments, the baboons were dewormed and observed to be disease free for at least 3 months.

For surgical procedures, animals were given ketamine hydrochloride (20 mg/kg intramuscularly) for induction of anesthesia, 1% halothane by endotracheal tube for anesthetic maintenance and buprenorphine, 0.01 mg/kg every 8 hr as needed postoperatively. For subsequent short-term immobilization in performing experimental procedures postoperatively, ketamine hydrochloride (5–20 mg/kg intramuscularly) was used.

Chronic exteriorized arteriovenous (AV) access shunts were surgically placed between the femoral artery and vein to expedite interposition of thrombogenic devices, drug infusions and blood sampling. The chronic AV shunts were composed of silicone rubber tubing, 3.0 mm inner diameter (Silastic, Dow Corning Corp., Midland, Mich.). The arterial and venous arms of the shunt were connected with a 1 cm length of blunt-edge polytetrafluoroethylene (Teflon) tubing (2.8 mm inner diameter). All materials were sterilized by autoclaving before surgical placement. These chronic AV shunts do not detectably activate platelets or fibrinogen (Harker et al., *J. Clin. Invest.* 64:559–569 (1979); Savage et al., *Blood* 68:386–393 (1986)). Thrombogenic devices (Cadroy et al., *J. Lab. Clin. Med.* 114:349–357 (1990); Schneider et al., *J. Vasc. Surg.* 11:365–372 (1990); Hanson et al., *Arteriosclerosis* 5:595–603 (1985)) were subsequently incorporated into the exteriorized AV shunts of awake animals for 165 min, and blood flows in the AV shunts were measured with a C-clamp-type ultrasonic flow probe interfaced with a Transonic T206 blood-flow analyzer (Transonic, Ithaca, N.Y.). Blood flows averaged 150±35 ml/min in control animals.

Blood counts and hematocrits were measured on whole blood collected in EDTA (2mg/ml) using a J. T. Baker Chemical Comp. (Jackson, Tenn.) model 810 whole-blood analyzer. The mean platelet count was $318 \pm 70 \times 10^3$ µl in the control group (Harker et al., *J. Clin. Invest.* 64:559–569 (1979)).

Template bleeding time measurements were performed on the shaved volar surface of the forearm as described previously (Hanson et al., *Proc. Natl. Acad. Sci. USA* 85:3184–3188 (1988); Harker et al., *J. Clin. Invest.* 64:559–569 (1979)). Plasma fibrinogen concentrations were measured as thrombin clottable protein using the method described previously (Harker et al., *J. Clin. Invest.* 64:559–569 (1979); Cadroy et al., *J. Lab. Clin. Med.* 114:349–357 (1989); Hanson et al., *Proc. Natl. Acad. Sci. USA* 85:3184–3188 (1988)).

The activated partial thromboplastin time and the thrombin clotting time were determined with citrated plasma samples (9 volumes of blood into 1 volume of 3.8% sodium citrate) from blood samples drawn 30 and 60 minutes after the beginning of each experiment (Kelly et al., *Blood* 77:1006–1012 (1991)). Activated partial thromboplastin time (activated partial thromboplastin time reagent; Ortho Diagnostic Systems, Raritan, N.J.) and thrombin clotting time (bovine thrombin, final concentration 1.7 U/ml) determinations were performed with a fibrometer (Fibrosystem; Becton Dickinson, Cockeysville, Mass.). tPA and uPA activity and antigen assays were performed as described previously (Bode et al., *Circulation* 84:805–813 (1991); Runge et al., *Proc. Natl. Acad. Sci. USA* 88:10337–10341 (1991)).

Model of Thrombolysis

To study thrombolysis in baboons, the lytic effects of infusing different PAs on preformed isotopically labeled thrombi were measured in real time using gamma camera imaging. This model differs from other models in that these thrombi were formed in vivo. Non-occluding platelet-rich thrombi with fibrin-rich propogated tails were preformed endogenously for 75 min on thrombogenic devices incorporated into chronic AV shunts with blood flows controlled at 40 ml/min in non-anticoagulated animals previously labeled with autologous $^{111}$In-platelets and $^{125}$I-fibrinogen.

The thrombogenic device comprised a 2 cm-long segment of Dacron vascular graft incorporated into the chronic AV shunts with blood flowing at 40 ml/min. Uncrimped Dacron graft (Bioknit), 4 mm i.d., was obtained from C. R. Bard, Inc. (Billerica, Mass.). Segments 2 cm in length were rendered impervious to blood leakage by external wrapping with Parafilm (American Can Company, New York, N.Y.) and 5.3 mm i.d. "heat shrunk" Teflon tubing. Butt joints were constructed that ensured smooth transition, forming devices suitable for incorporation into the AV shunts (Hanson et al., *Arteriosclerosis* 5:595–603 (1985); Hanson et al., *Proc. Natl. Acad. Sci. USA* 85:3184–3188 (1988); Kelly et al., *Blood* 77:1006–1012 (1991)). Platelet-rich thrombus formed rapidly on the segment of Dacron vascular graft, reaching a plateau by about 75 min. Because of the low-flow conditions, thrombus forming on the vascular graft concurrently propagated a fibrin-rich tail down-stream in the shunt (FIG. 12).

Autologous baboon platelets were labeled with 1 mCi $^{111}$In oxide as previously described (Hanson et al., *Arteriosclerosis* 5:595–603 (1985)) and were reinjected at least one hour prior to placement of the thrombogenic devices. Labelling efficiencies averaged 90%. $^{111}$In-labeled platelets were functionally normal (Savage et al., *Blood* 68:38;5–393 (1986); Hanson et al., *Arteriosclerosis* 5:595–603 (1985)). Baboon fibrinogen was purified by β-alanine precipitation and was labeled with $^{125}$I by the ICI method as described previously (Harker et al., *J. Clin. Invest.* 64:559–569 (1979); Kelly et al., *Blood* 77:1006–1012 (1991)). Labeling efficiency averaged 70%. The labeled fibrinogen was >90% clottable. A 5 µCi dose of labeled fibrinogen was injected intravenously 10 min before exposing the device.

To maintain the amount of thrombus relatively constant without occlusion during the subsequent hour (FIG. 13C), heparin infusions were initiated (bolus of 100 U/kg, followed by continuous intravenous infusions of 100 U/kg over 60 minutes). Accordingly, test molecules were infused intravenously for this 60 min period of thrombus stability. The lytic loss of pre-existing labeled thrombus was measured for each PA during the periods of infusion and throughout the subsequent 30 min. Blood tests of thrombolysis, thrombosis and hemostatic function (see below) were also performed on blood samples collected in tubes containing 3.8% sodium citrate prior to placing the thrombogenic devices (0 min), before beginning the test infusions (75 min), at the end of the test infusions (135 min), and at the end of the experiments (165 min). Measurements were performed on blinded, coded samples for plasma rtPA and rscuPA antigen and activity levels, and for plasma activity levels of plasminogen, $\alpha_2$-antiplasmin and PAI-1.

After 75 minutes, when the thrombus was established and stabilized, the PAs were administered intravenously in combination with heparin, as described above. Dose-response studies were performed for rtPA at 2.85 nmol/kg (0.2 mg/kg), 14.2 nmol/kg (1.0 mg/kg) or 28.5 nmol/kg (2.0 mg/kg)), for rscuPA at 2.85 nmol/kg (0.15 mg/kg), 14.2 nmol/kg (0.77 mg/kg), 28.5 nmol/kg (1.54 mg/kg), or 72.2 nmol/kg (3.9 mg/kg)), and for r59D8(—CH$_2$)-scuPA at 1.89 nmol/kg (0.15 mg/kg)). Ten percent of the total dose was administered as an intravenous bolus followed by the remainder of the dose infused over one hour. Imaging of both the platelet-rich graft thrombus and fibrin-rich tail were performed as described below, including a final image 30 minutes after completing the infusion. Control studies were carried out in 6 animals receiving no heparin, and in 4 animals receiving heparin only.

Images of the vascular graft, including proximal and distal segments of the AV shunts, were acquired with a General Electric 400T MaxiCamera (Milwaukee, Wis.) and were stored and analyzed with a Medical Data Systems A$^3$ image processing system (Medtronic, Ann Arbor, Mich.) interfaced with the camera (Hanson et al., *Arteriosclerosis* 5:595–603 (1985)). The low energy peak (172 KeV) of $^{111}$In was imaged with a 10% energy window. Dynamic images were acquired at 5-minute intervals. Immediately after each dynamic study, standards were imaged, including a syringe containing 5.0 ml of whole blood (blood standard) and an identical thrombogenic device filled with static autologous blood (device standard). The imaging routines and isotopic detection protocols for these shunt studies used procedures reported previously (Hanson et al., *Proc. Natl. Acad. Sci. USA* 85:3184–3188 (1988); Cadroy et al., *J. Lab. Clin. Med.* 114:349–357 (1989); Savage et al., *Blood* 68:386–393 (1986); Schneider et al., *J. Vasc. Surg.* 11:365–372 (1990)).

For thrombolysis experiments, the thrombus consisted of two regions of interest which were analyzed separately: a) the platelet-rich thrombus at the dacron graft was analyzed over 2 cm (8×10 pixel region of interest); and b) the fibrin-rich tail was analyzed over a length of 20 cm (80×10 pixels). Images were acquired at 5 minute intervals. The total number of deposited platelets in each region (labeled plus unlabeled platelets) was calculated by dividing the deposited platelet activity (counts per minute) by the circulating blood activity (counts per minute per milliliter) and multiplying by the circulating platelet count (platelets per milliliter) as described previously (Hanson et al., *Proc. Natl. Acad. Sci. USA* 85:3184–3188 (1988)). Radioactivity values referred to platelet activity only, with all blood measurements having been corrected for the small fraction of nonplatelet isotope in each experiment. Nonplatelet plasma activities averaged 10%±1% (n=24) of whole blood activity in these studies. $^{111}$In-platelet emissions were counted to measure thrombus formation. For this measurement, emissions from both the Dacron graft and the fibrin-rich tail regions of the experimental device were counted in 2 cm long (8×10 pixels) regions of interest. Deposited $^{111}$In-labeled platelet activity was calculated by subtracting the device standard activity from each region of interest.

The amounts of fibrin in the platelet-rich thrombi and fibrin-rich thrombi were measured using homologous $^{125}$I-labeled fibrinogen. Baboon $^{125}$I-fibrinogen (5 μCi) was injected intravenously 10 minutes prior to incorporating the device in the AV shunt. After completion of the experiment, the device was thoroughly washed with isotonic saline solution perfused at 20 ml/minute. The vascular graft thrombus was then separated from the propogated tail for counting of emissions. $^{125}$I activity was measured at least 30 days after the study to allow for the decay of $^{111}$In activity (half-life, 2.8 days). Total fibrin deposition was calculated by dividing the deposited $^{125}$I-fibrin activity (counts per minute) by the clottable fibrinogen activity (counts per min/ml) and multiplying by the plasma fibrinogen level (mg/ml). The concentration of fibrinogen in plasma was estimated spectrophotometrically by a modification of Jacobsson's method (Harker et al., *J. Clin. Invest.* 64:559–569 (1979); Kelly et al., *Blood* 77:1006–1012 (1991)).

Model of Thrombus Formation

In studies designed to measure the effects of lytic agents on rates of new thrombus formation, thrombogenic devices were interposed between the arms of the permanent shunt system of awake animals for one hour. Use of the device resulted in the formation of platelet-rich, arterial-type thrombi on 2-cm long segments of Dacron vascular graft, and the formation of fibrin-rich, venous type thrombi in a chamber of expanded diameter and disturbed flow placed immediately distal to the segment of vascular graft, as described previously (Cadroy et al., *J. Lab. Clin. Med.* 114:349–357 (1989); Cadroy et al., *Proc. Natl. Acad. Sci. USA* 88:1177–1181 (1991)). Dacron vascular graft segments were prepared from externally supported, uncrimped, knitted Dacron grafts 2 cm long with a 4.0 mm i.d. (Hanson et al., *Proc. Natl. Acad. Sci. USA* 85:3184–3188 (1988); Kelly et al., *Blood* 77:1006–1012 (1991)). The grafts were rendered impervious to blood leakage by an external wrapping of Parafilm, placed inside a 5 cm length of 5.3 mm i.d. heat-shrunk Teflon tubing comprised of an expanded distal chamber. At the flow rate used in these studies, 20 ml/min, the wall shear rate on the dacron graft was 100 sec$^{-1}$. The "chamber" was 2 cm distal to the dacron segment and consisted of an expansion of tubing diameters from 3.2 mm to 9.3 min. This expansion region produced a complex flow pattern, with reverse flow along the wall and formation of a captive annular vortex. Before thrombi formed, shear rates along the chamber walls quite low, with essentially no flow in the corner regions. In general, this pattern of flow recirculation resulted in a prolonged residence time of blood cells and procoagulant species and increased the likelihood that these elements will form a thrombus. At the time of the study, the 3.2 mm inner diameter tubing segments proximal and distal to the thrombogenic device were connected between the segments of the permanent arteriovenous (AV) shunt with 2 cm long Teflon connectors (Chemplast Inc., Wayne, N.J.). Blood flow was maintained at 20 ml/min using a variable-speed peristaltic roller pump (Masterflow model 7016; Cole-Parmer Instrument Co., Chicago, Ill.) interposed between the device and the femoral vein (i.e., distal to the device). As described for the thrombolysis studies, $^{111}$In-platelet emissions were counted to measure thrombus formation. For this measurement, emissions from both the Dacron graft and chamber regions of the experimental device were counted in 2 cm long (8×10 pixels) regions of interest. Deposited $^{111}$In-labeled platelet activity was calculated by subtracting the device standard activity from each region of interest.

Four indicators of acute thrombus formation were measured. Deposited autologous $^{111}$In-platelets were counted by scintillation camera imaging. The accumulation of $^{125}$I-fibrin was measured by gamma counting. Device patency was measured by Doppler flow analysis through the shunt using a C-clamp type flow probe interfaced with a Transonic T206 Blood Flow Analyzer (Transonic Corp., Ithaca, N.Y.). Plasma levels of markers of thrombosis (platelet factor 4 (PF4), beta-thromboglobulin (βTG), fibrinopeptide A(FPA), and thrombin:antithrombin complex (TAT)) (Cadroy et al., *Proc. Natl. Acad. Sci. USA* 88:1177–1181 (1991); Gruber et al., Circulation 82:578–585 (1990)) were determined at three time points: (1) at baseline prior to the incorporation of thrombogenic segments into the AV shunt; (2) after exposing the thrombogenic segments to arterial rates of blood flow for 1 hr (Cadroy et al., J. Lab. Clin. Med 114:349–357 (1989); Hanson et al., Proc. Natl. Acad. Sci. USA 85:3184–3188 (1988); Kelly et al., Blood 77:1006–1012 (1991); Cadroy et al., Proc. Natl. Acad. Sci. USA 88:1177–1181 (1991)); and (3) at the conclusion of the experiment.

Infusion of either rscuPA or r59D8(—CH$_2$)-scuPA and $^{111}$In-labeled platelet imaging were begun as soon as blood flow was established. rscuPA (total dose of 3.7 nmol/kg) or r59D8(—CH$_2$)-scuPA (total dose of 0.31 nmol/kg), diluted in saline solution before the experiment, was given by continuous infusion over 1 hour to maintain a constant systemic drug level throughout the experiment.

Results

Development and Use of the Thrombolysis Model

Figure 13A:
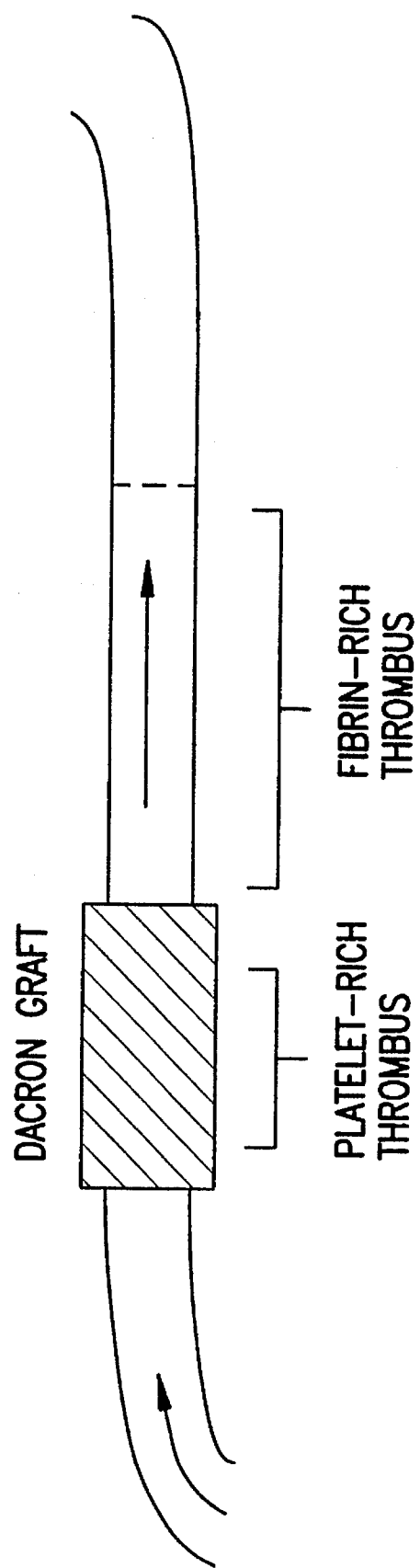
Figure 13B:
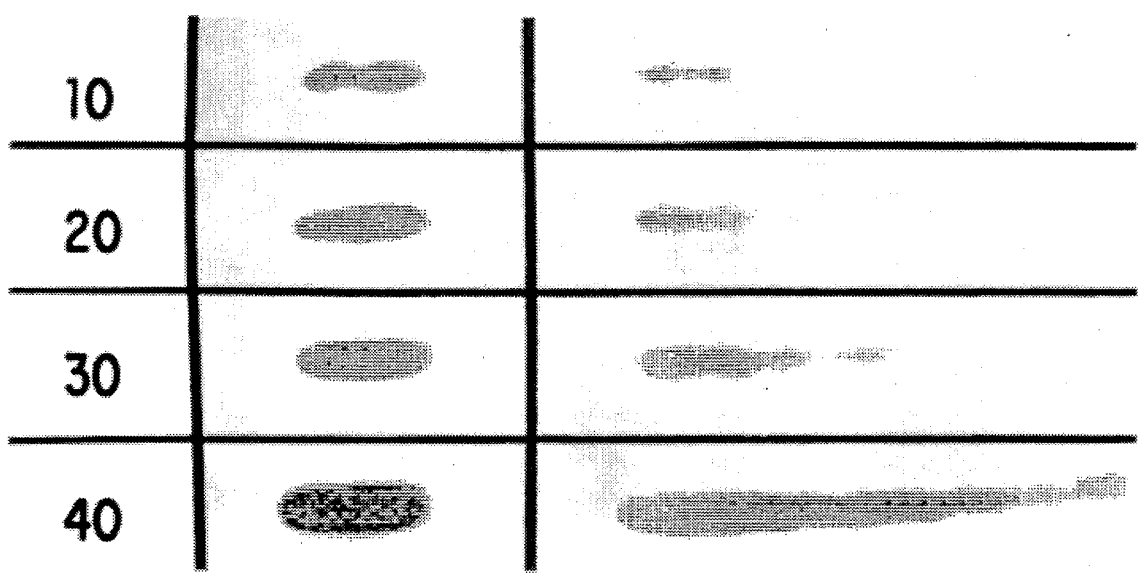
Figure 13C:
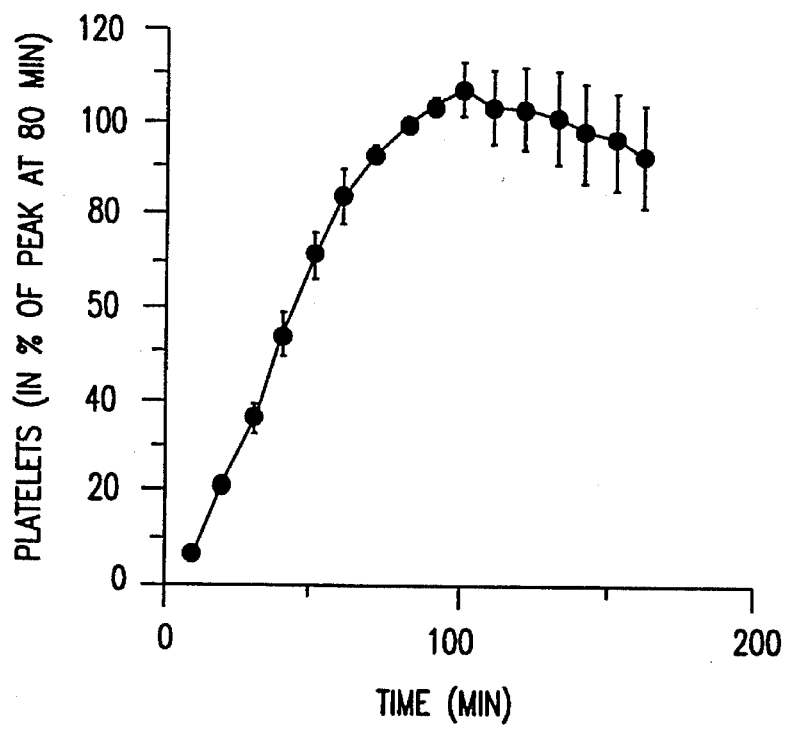
Figure 13D:
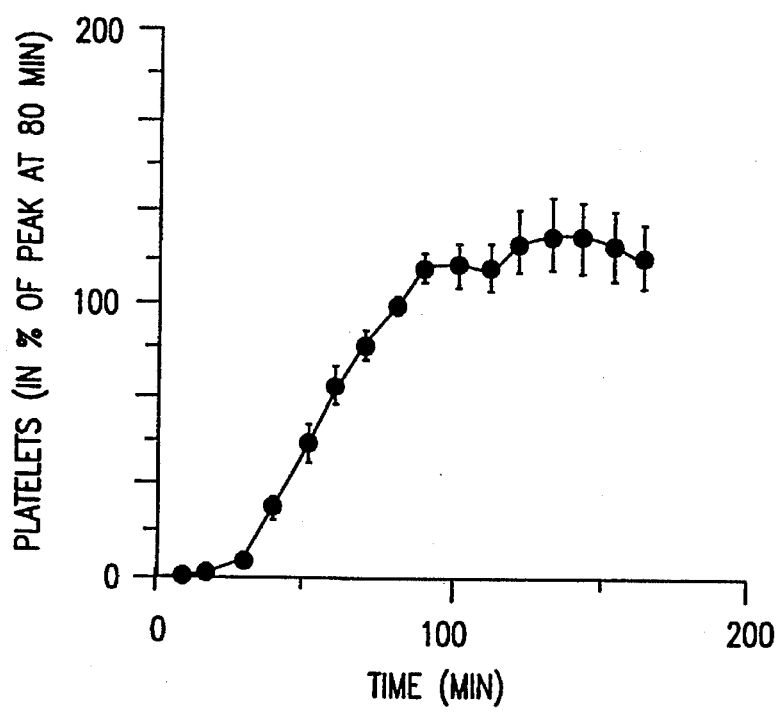

The thrombolytic model is schematically shown in FIGS. 13A, 13B and 13C. In this model thrombi to be lysed are preformed in vivo. The addition of systemic heparin was found to maintain stable, non-occlusive thrombi of defined morphology and geometry throughout the study period in the absence of PA infusion. Six animals were treated with heparin but did not receive PA therapy. In these animals, platelets accumulated rapidly, reaching a plateau by 75 min, with no significant changes in platelet deposition during the subsequent 90 min. This formation of stable platelet-rich thrombi (within the graft) and fibrin-rich thrombi (in the tail) was quantitated by gamma camera imaging (middle and lower panels of FIGS. 13A, 13B and 13C). As shown, sufficient numbers of platelets were present in the fibrin-rich tail to quantify the amount of thrombus by imaging. In contrast, a second control group of controls consisted of six animals that received neither a PA nor heparin (data not shown). Five of the six animals treated in this way occluded the graft at 100±15 min. Thrombi formed in the absence of heparin were not suitable for thrombolytic studies because: 1) the timing of occlusion was unpredictable; 2) the grafts predictably occluded thereby rendering the: thrombus inaccessible to systemic PAs; and 3) when lysed, the occlusive thrombi embolized erratically, thus obscuring the kinetics of thrombolysis.

Thrombolytic Comparision of r59D8(—CH$_2$)-scuPA with rtPA and rscuPA

Four to six animals were evaluated in each control and experimental group to determine the relative thrombolytic potency of rtPA, rscuPA, and r59D8(—CH$_2$)-scuPA for dissolution of platelet-rich and fibrin-rich thrombi. The same cohort of animals received each of the three different PAs on serial days in random sequence. The effects of administrating a PA on platelets or fibrin present in either the platelet-rich or the fibrin-rich thrombi are shown in FIGS. 14–16.

In the fibrin-rich tail segment, dose-dependent thrombolysis was achieved for both rtPA (FIG. 14C) and rscuPA (FIG. 15C). As the dose of the PA was increased, the thrombus was lysed more quickly and more completely. The same dose-response relationships were evident for lysis of the platelet-rich thrombus present on the Dacron graft (FIGS. 15A, 15B, 16A and 16C), although both the rate and extent of thrombolysis was less than for the fibrin-rich tail. FIGS. 16A, 16B and 16C show that a low dose of r59D8(—CH$_2$)-scuPA (1.89 nMol/kg) produced equivalent thrombolysis to that observed for rtPA (14.2 nMol/kg) and rscuPA (28.5 nMol/kg) and exhibited 7.5 and 15-fold higher potencies, respectively.

Plasma measurements of thrombolysis and hemostasis showed that r59D8(—CH$_2$)-scuPA produced significantly less disruption of hemostasis than rtPA or rscuPA (Tables 4 and 5; FIG. 17). Although the measured plasma levels of rtPA and rscuPA increased in a dose-dependent manner, the plasma level of r59D8(—CH$_2$)-scuPA was less than anticipated based on the administered dose. When the plasma levels of the PAs were used to compare thrombolytic efficacy, r59D8(—CH$_2$)-scuPA was 124- and 284-fold more potent than rtPA and rscuPA respectively.

TABLE 4

Measurement of Plasma Parameters for Disruption of Hemostasis in the Thrombolysis Experiments.

| | n | time (min) | Hct % | Plts × 10$^5$ | APTT (sec) | Bleeding Time (min) | TAT (µg/l) |
|---|---|---|---|---|---|---|---|
| Controls | 5 | 0 | 34.6 ± 1.79 | 374 ± 12.4 | 30.5 ± 0.63 | 3.0 ± 0 | 13.6 ± 2.03 |
| | | 165 | — | 304 ± 71 | — | — | — |
| Heparin | 5 | 0 | 37.4 ± 3.09 | 401 ± 72 | 32 ± 0.85 | 3.0 ± 0 | 11.1 ± 1.07 |
| 100 u/kg | | 165 | 34.9 ± 2.15 | 32.8 ± 69 | 219 ± 32.6 | — | 30.6 ± 57.5 |
| rtPA | 4 | 0 | 33.8 ± 0.95 | 360 ± 81 | 31 ± 0.6 | 3.0 ± 0 | 12.01 ± 1.65 |
| 2.8 nmol/kg | | 165 | 30.3 ± 0.9 | 293 ± 37 | 178 ± 42.9 | — | 33.6 ± 7.30 |
| rtPA | 5 | 0 | 34.6 ± 1.52 | 322 ± 71 | 32 ± 0.63 | 5.3 ± 0.36 | 18.1 ± 7.28 |
| 14.2 nmol/kg | | 165 | 32.6 ± 1.79 | 276 ± 59 | 44 ± 1.49 | — | 36.2 ± 8.20 |
| rtPA | 1 | 0 | 32.0 | 300 | 30 | 8.0 | 12.17 |
| 28.5 nmol/kg | | 165 | 27.4 | 255 | 264 | — | 32.5 |
| rscuPA | 3 | 0 | 34.0 ± 0.02 | 360 ± 115 | 35 ± 1.44 | 5.0 ± 0.27 | 14.83 ± 1.62 |
| 2.8 nmol/kg | | 165 | 34.4 ± 1.91 | 276 ± 71 | 202 ± 4.70 | — | 21.6 ± 5.25 |
| rscuPA | 4 | 0 | 35.0 ± 1.20 | 390 ± 20 | 34 ± 1.95 | 5.2 ± 0.04 | 15.5 ± 1.55 |
| 14.2 nmol/kg | | 165 | 33.2 ± 0.15 | 300 ± 51 | 262 ± 19.5 | — | 39.1 ± 11.3 |
| rscuPA | 2 | 0 | 34.6 ± 1.06 | 435 ± 59 | 31 ± 0.21 | 6.5 ± 0.35 | 20.36 ± 7.85 |
| 28.5 nmol/kg | | 165 | 30.6 ± 1.98 | 331 ± 49 | >300 | — | 32.0 ± 5.66 |
| rscuPA | 2 | 0 | 33.5 ± 2.19 | 383 ± 35 | 34 ± 1.95 | >30 | 21.7 ± 0.53 |
| 72.2 nmol/kg | | 165 | 27.8 ± 1.20 | 303 ± 31 | >300 | — | 70.7 ± 30.55 |
| r59D8(—CH$_2$)- | 3 | 0 | 34.3 ± 1.21 | 327 ± 36 | 32 ± 0.75 | 3.5 ± 0.12 | 12.3 ± 1.1 |
| scuPA | | 165 | 31.0 ± 0.98 | 241 ± 31 | 211 ± 21.65 | — | 33.4 ± 3.18 |
| 1.89 nmol/kg | | | | | | | |

TABLE 5

Measurement of Antihemostatic Effects of r59D8(—CH$_2$)-scuPA and rscuPA in the Inhibition of Thrombosis Experiments.

| | uPA Activity (units/ml) | uPA Antigen (pmol/ml) | PAI-1 (ng/ml) | PMG (%) | α-2-antiplasmin (%) | Fibrinogen (ng/dl) |
|---|---|---|---|---|---|---|
| | | | r-scuPA | | | |
| Pre | 6.5 ± 1.4 | 0 | 2.0 ± 1 | 243 ± 24 | 95 ± 4.5 | 197 ± 18 |
| P-30' | 12.5 ± 1.2 | 2.3 ± 0.05 | 1.93 ± 0.92 | 251 ± 45 | 74 ± 8 | 193 ± 20 |
| D-30' | 52.0 ± 12 | 21.04 ± 0.2 | 2.05 ± 1.2 | 209 ± 28 | 76 ± 8 | 169 ± 23 |
| P-60' | 22.0 ± 1.9 | 2.5 ± 0.2 | 2.43 ± 1.3 | 269 ± 33 | 84 ± 9 | 186 ± 20 |
| D-60' | 76 ± 20 | 23.2 ± 0.2 | 2.9 ± 1.7 | 222 ± 28 | 87 ± 12 | 152 ± 18 |
| | | | r59D8(—CH$_2$)-scuPA | | | |
| Pre | 7.5 ± 2.5 | N.D. | 2.65 ± 1.52 | 238 ± 36 | 86 ± 8 | 186 ± 22 |
| P-30' | 11.0 ± 0.8 | N.D. | 3.3 ± 2.3 | 209 ± 29 | 93 ± 10 | 179 ± 22 |
| D-30' | 10.5 ± 0.9 | N.D. | 2.8 ± 1.7 | 245 ± 28 | 80 ± 19 | 175 ± 22 |
| P-60' | 10.0 ± 1.1 | N.D. | 3.3 ± 2.1 | 241 ± 26.5 | 94 ± 10 | 180 ± 22 |
| D-60' | 10.8 ± 1.4 | N.D. | 4.1 ± 1.6 | 232 ± 31.4 | 102 ± 14 | 168 ± 21 |

Antihemostatic Comparison of r59D8(—CH$_2$)-scuPA with rtPA and rscuPA

The antihemostatic effects of these infusions were also studied (Tables 3 and 4). The most significant hemostatic difference was in the template bleeding times (FIG. 17). The template bleeding time was at least doubled in the animals which received 14.2 nmol/kg rtPA (8.0±1.5 min, p<0.05 vs. control) or 28.5 nmol/kg rscuPA (6.5±1.0 min, p <0.05 vs. control) while there was no prolongation of the bleeding time in animals which received a comparable thrombolytic dose of r59D8(—CH$_2$)-scuPA (3.5±0.6 min in animals which received 1.89 nmol/kg; not significantly different from control). In addition, the consumption of α-2-antiplasmin and the increase in D-dimer were significantly less in animals which received r59D8(—CH$_2$)-scuPA than equivalent doses of 28.5 nMol/kg rscuPA and 14.2 nMol/kg rtPA. For comparison, the measured plasma levels for each of the PAs are also shown in FIG. 17. Since the thrombin-antithrombin III complex formation was comparable for all three PAs, the amount of soluble thrombin formed by the thrombus appeared to be relatively constant during the studies.

Inhibition of Thrombus Formation r59D8(—CH$_2$)-scuPA inhibited thrombus formation more effectively than rscuPA (FIGS. 18A and 18B). The antithrombotic effects of rscuPA and r59D8(—CH$_2$)-scuPA was determined at low-flow (40 ml/min) using a thrombogenic device incorporated into chronic exteriorized AV shunts in baboons. This device consisted of a proximal 2 cm segment of vascular graft followed by an expanded chamber with static and disturbed flow. In this model, platelet-rich arterial-type thrombus formed on the graft and fibrin-rich venous-type thrombus formed in the expanded chamber. Each of five animals bearing segments of Dacron vascular graft and the expansion chamber were evaluated on serial days in random sequence. Either rscuPA or r59D8(-CH2)scuPA was infused proximally to the thrombogenic segments for 60 min and the rate and extent of thrombus formation was quantitated by gamma camera imaging of $^{111}$In-labeled platelets. Thrombi formed rapidly on segments of Dacron vascular graft in untreated controls, reaching a peak value by 60 minutes. Platelet and fibrin deposition were interrupted in the chamber by both rscuPA (3.7 nmol/kg per hour achieving a plasma concentration of 23.2±0.2 pmol/ml) and r59D8(—CH$_2$)-scuPA (0.31 nmol/kg/hour and plasma concentrations below the limit of detection of the assay used). Based on the administered dose, r59D8(—CH$_2$)-scuPA was at least 11-fold more effective than rscuPA in preventing platelet deposition on the segment of vascular graft.

Hemostatic determinations were also measured. Fibrinogen levels and platelet counts in animals treated with either rscuPA or r59D8(—CH$_2$)-scuPA did not differ (p=ns) (Table 5). In addition, plasminogen, α-2-antiplasmin and PAI-1 levels were not significantly changed compared with controls for r-scuPA or r59D8(—CH$_2$)-scuPA (Table 5).

Discussion

This study demonstrated that r59D8(—CH$_2$)-scuPA, a hybrid recombinant PA, is a significantly more potent, more specific thrombolytic and antithrombotic agent than either rtPA or rscuPA. These conclusions are based on the results using clinically relevant models in baboons showing comparable thrombolytic efficacy with fewer associated systematic effects when administered at a dose of r59D8(—CH$_2$)-scuPA that was 7% that of rscuPA and 13% that of rtPA. On the basis of measured plasma levels, r59D8(—CH$_2$)-scuPA was 124- and 284-fold more potent than rtPA and rscuPA, respectively. At comparable thrombolytic doses, the template bleeding times were less prolonged, and the degradation of α-2-antiplasmin and generation of D-dimer were reduced.

The thrombolytic model developed in baboons for these studies (FIGS. 13A, 13B and 13C) was quantitative and reproducible. This method discriminated between lytic doses for arterial (platelet-rich) and venous (fibrin-rich) thrombi formed in vivo and provided concurrent evaluation of hemostasis. In this thrombolysis model, non-occlusive platelet-rich and fibrin-rich thrombi were performed by incorporating a segment of Dacron vascular graft into an exteriorized AV shunt and decreasing blood flow to 40 mL/min. This model was clinically relevant for comparing different thrombolytic agents because: flow geometry was defined; thrombus formation was reproduceable; and baboon and human mechanisms are similar. Compared to other thrombolysis models, the novel feature of this model is that the formation of thrombus occurs in vivo prior to the administration of the thrombolytic agent.

Four related observations from these in vivo experiments merit additional comment. First, r59D8(—CH$_2$)-scuPA therapy exhibited thrombolytic efficacy greater than any previously reported, second or third generation PA, based either on administered dose or on measured plasma levels. Second, the administration of r59D8(—CH$_2$)-scuPA produced plasma levels at least 50-fold lower than anticipated. Third, template bleeding times were normal in animals treated with r59D8(—CH₂)-scuPA compared to those treated with comparable thrombolytic doses of rtPA and rscuPA. Fourth, low doses of r59D8(—CH₂)scuPA inhibited the rate and extent of both platelet-rich and fibrin-rich thrombus formation, indicating that thrombolytic doses of r59D8(—CH₂)-scuPA also inhibited thrombus formation.

The increased potency of r59D8(—CH₂)-scuPA for lysis of fibrin-rich thrombi was expected based on prior characterization of venous clot lysis in rabbits treated with r59D8(—CH₂)-scuPA (Runge et al., *Proc. Natl. Acad. Sci. USA* 88:10337–10341 (1991)) and on the observations of Holvoet et al. (*Blood* 81:696–703 (1993)) who used a similar molecule to lyse experimental pulmonary emboli in hamsters. This increase in thrombolytic potency was suggested to reflect both the increased specificity of the hybrid PA and the reduced clearance. The findings reported here indicate that the increased thrombolytic potency is clearly due to increased specificity. The low measured plasma levels (discussed below) for r59D8(—CH₂)-scuPA that corresponded to effective thrombolysis excluded increased plasma half-life as the primary explanation of improved efficacy. These plasma concentrations also indicated that r59D8(—CH₂)-scuPA may depend more on its relative fibrin affinity (i.e. local concentration) than on plasma concentration for effective lysis. The increased potency for lysis of platelet-rich, arterial-type thrombi was unexpected because the relative amount of fibrin present in arterial-type thrombi is much less than in venous-type thrombi. The potency of r59D8(—CH₂)-scuPA for the lysis of arterial-type thrombi indicated that fibrin was an effective target for the treatment of platelet-rich thrombi.

The plasma levels of r59D8(—CH₂)-scuPA that produced effective thrombolysis were much lower than anticipated since previous published reports described a prolonged plasma half-life for other antibody-targeted PAs (Holvoet et al., *J. Biol. Chem.* 266:19717–19724 (1991); Runge et al., *Proc. Natl. Acad. Sci. USA* 88:10337–10341 (1991); Holvoet et al., *Blood* 81:696–703 (1993); Runge et al., *Proc. Natl. Acad. Sci. USA* 84:7659–7662 (1987); Collen et al., *Fibrinolysis* 3:197–202 (1989)). Indeed, in control baboons without thrombogenic devices, bolus infusion Of r59D8(—CH₂)-scuPA resulted in clearance of a significant amount (~50%) of the scuPA antigen within the first 2–3 minutes and subsequent clearance was at a reduced rate (with a plasma half-life of 55±9 min) (unpublished data).

In measuring plasma levels Of r59D8(—CH₂)-scuPA in these experiments, both antigen and activity were decreased. Thus, it is unlikely that the epitope recognized in the antigen assays was obscured, that the activity was inhibited, or that these data represented simple technical artifacts. The explanation for these very low plasma levels may involve several mechanisms. First, the rapid clearance of r59D8(—CH₂)-scuPA is probably explained by the early removal of "microaggregated molecules" present in the preparation despite filtering prior to infusion (see below). In addition, r59D8(—CH₂)-scuPA may have been bound to soluble fibrin or fibrinogen fragments with subsequent more rapid clearance or, r59D8(—CH₂)-scuPA may have undergone modification in the thrombogenic millieu such that it is recognized by reticuloendothelial cells and cleared. Finally, a significant portion of r59D8(—CH₂)-scuPA may have been incorporated into forming thrombi.

To investigate the possibility that "microaggregated particles" were present in these preparations, additional in vitro characterization of the prepartaions used in the in vivo study was performed. Because all material for infusion was passed through a 0.22 µm filter immediately prior to infusion the explanation of "microparticles" seemed unlikely. In fact, in subsequent in vitro experiments passage through a second 0.22 µm filter resulted in no significant decrease in protein or activity. However, centrifugation for 10 minutes at 10,000×g produced a loss of ~30% of protein and 15% of antigen while centrifugation for 30 minutes at 50,000×g caused a loss of ~75% of protein and ~40% of antigen. These experiments suggested a significant proportion of the administered r59D8(—CH₂)-scuPA consisted of "microaggregates" that were rapidly cleared by the reticuloendothelial system or possibly bound to forming thrombus. Although this does not fully explain why measured levels were less than 10% of the anticipated levels, this finding provided a partial explanation.

An important difference in the PAs was the effect on template bleeding times. Clinically both rtPA (Gimple et al., *Circulation* 80:581–588 (1989)) and, to a greater degree, rscuPA prolonged template bleeding times. There has been a correlation reported between elevation in template bleeding time and intracranial bleeding (Kelly et al., *Blood* 77:1006–1012 (1991)). The mechanism for this is not clear, but may relate to systemic effects of the fibrinogen breakdown products. Whether the specificity of r59D8(—CH₂)-scuPA and its limited systemic effects will also reduce intracranial bleeding remains to be determined.

Measurements of both r59D8(—CH₂)-scuPA plasma concentration and antithrombotic potency are relevant when interpreting the differences in template bleeding time, α-2-antiplasmin degradation, and D-dimer generation observed at comparable thrombolytic doses. For example, a minimal decrease in α-2-antiplasmin is expected, based on the very low plasma concentration of r59D8(—CH₂)-scuPA, since r59D8(—CH₂)-scuPA certainly generates less systemic plasmin than either rtPA or rscuPA. X more complex explanation is required to account for the observations that r59D8(—CH₂)-scuPA did not prolong the template bleeding and produced less D-dimer than equipotent does of rtPA and rscuPA. The effects of the three PAs studied were similar with regard to both template bleeding time and D-dimer generation: r59D8(—CH₂)-scuPA<rtPA<rscuPA. Several potential mechanisms may account for these observations. First, it is quite possible that the D-dimer assay used here also measured fibrinogen breakdown products. In that case, the concordance between D-dimer levels and template bleeding times would be due to the known effect of fibrinogen breakdown products on platelet function. It has been shown that fibrinogen breakdown products can compete with fibrinogen for glycoprotein IIb/IIIa binding and when present in high Concentrations fibrinogen breakdown products produce platelet dysfunction. Alternatively, r59D8(—CH₂)-scuPA may inhibit by decreasing the total amount of lysed thrombus (because less new thrombus is formed) during the experimental period and thus less D-direct is produced. The observation that there is no significant difference in thrombin-antithrombin III levels among the three PAs is consistent with either explanation. Finally, there has been much discussion in the literature about the effects of PA therapy on thrombus formation. Data have been reported supporting and contradicting the notion that plasmin activates platelets. Both fibrin and fibrinogen degradation products exhibit antiplatelet and anticoagulant properties, further complicating the interpretation. r59D8(—CH₂)-scuPA clearly inhibited thrombosis more than rscuPA (and probably more than rtPA) at the doses used here. The possibility exists that the small increase in D-dimer generation by r59D8(—CH₂)-scuPA may indicate that at these doses r59D8(—CH₂)-scuPA is less "thrombogenic" than either rtPA or rscuPA. However, the equivalence in the levels of thrombin-antithrombin complexes argues against this explanation.

The thrombosis model used here was designed to simulate the process of rethrombosis occuring in 5–15% of patients following thrombolytic therapy (Chesebro et al., *N. Engl. J. Med.* 319:1544–1545 (1988); TIMI Study Group, *N. Engl. J. Med.* 312:932–936 (1985); Topol et al., *N. Engl. J. Med* 317:581–588 (1987)). In this model, r59D8(—CH$_2$)-scuPA is 11-fold more efficient than rscuPA in preventing formation of both platelet-rich and fibrin-rich thrombi. Although we had anticipated the increased antithrombotic efficacy observed in expansion chambers, the enhanced potency observed in the Dacron vascular graft was of interest. It has previously been argued that fibrin targeting is not applicable to the treatment of coronary artery thrombi because arterial thrombi tend to be platelet-rich and fibrin-poor. Our data indicate that there is sufficient fibrin present in the platelet-rich thrombi found in the vascular graft segments to effectively subserve targeting of rscuPA by an antifibrin antibody. We interpret this antithrombotic activity of r59D8(—CH$_2$)-scuPA to reflect a shift in the balance between thrombus deposition and lytic removal resulting in a net decrease in the rate of accumulated mass of thrombus (see below). Interestingly, this effect of r59D8(—CH$_2$)-scuPA (50% inhibition of platelet deposition at 0.3 nM) reduced thrombus formation more potently than the irreversible thrombin inhibitor D-Phe-Pro-Arg-chloromethylketone (IC$_{50}$~50 nM) (Hanson et al., *Proc. Natl. Acad. Sci. USA* 85:3184–3188 (1988)).

In summary, these data demonstrated that a recombinant hybrid PA, r59D8(—CH$_2$)-scuPA, combined increased thrombus specificity with thrombolytic and antithrombotic efficacy in a clinically relevant animal model. Accordingly, r59D8(—CH$_2$)-scuPA may both lyse thrombi and prevent rethrombosis more effectively and safely than the native PAs, rtPA and rscuPA.

While the invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A recombinant hybrid immunoglobulin molecule comprising (1) at least a variable region which is also specific for fibrin and (2) a fibrinolytic enzyme, wherein said fibrinolytic enzyme is selected from the group consisting of tissue-type plasminogen activator, streptokinase, urokinase, and prourokinase, wherein said recombinant hybrid immunoglobulin molecule is a single chain molecule encoded by a single contiguous DNA sequence.

2. The hybrid immunoglobulin molecule according to claim 1, wherein said hybrid immunoglobulin molecule is selected from the group consisting of urokinase-64C5 and tPA-59D8.

3. A pharmaceutical composition comprising the hybrid immunoglobulin molecule of claims 1 or 2, and a pharmaceutically acceptable carrier.

4. A method of lysing a thrombus in a patient comprising: administering to said patient, an effective amount of the pharmaceutical composition of claim 3.

5. A method of detecting a thrombus in an animal comprising:

(a) administering to said animal the molecule of claim 1 wherein said molecule is radiolabeled and (b) detecting the presence of said thrombus.

* * * * *